United States Patent
Ogawa et al.

(10) Patent No.: US 7,952,352 B2
(45) Date of Patent: May 31, 2011

(54) METHOD OF LOCALLY MEASURING MOBILITY OF PROTIC SOLVENT IN SAMPLE, INSTRUMENT OF LOCALLY MEASURING MOBILITY OF PROTIC SOLVENT IN SAMPLE, MEASURING INSTRUMENT LOCALLY MEASURING BEHAVIOR OF PROTIC SOLVENT IN SAMPLE BASED ON MAGNETIC

(75) Inventors: Kuniyasu Ogawa, Kanagawa (JP);
Tomoyuki Haishi, Ibaraki (JP); Kohei Ito, Fukuoka (JP)

(73) Assignee: Keio University, Minato-ku, Tokyo (JP)

( * ) Notice: Subject to any disclaimer, the term of this patent is extended or adjusted under 35 U.S.C. 154(b) by 869 days.

(21) Appl. No.: 11/911,176

(22) PCT Filed: Apr. 11, 2006

(86) PCT No.: PCT/JP2006/307667
§ 371 (c)(1),
(2), (4) Date: Oct. 10, 2007

(87) PCT Pub. No.: WO2006/109803
PCT Pub. Date: Oct. 19, 2006

(65) Prior Publication Data
US 2010/0201357 A1    Aug. 12, 2010

(30) Foreign Application Priority Data

Apr. 11, 2005  (JP) .................................. 2005-113977
May 18, 2005  (JP) .................................. 2005-144917

(51) Int. Cl.
*G01V 3/00* (2006.01)

(52) U.S. Cl. ..................................... 324/307; 324/309

(58) Field of Classification Search .......... 324/300–322;
600/407–445
See application file for complete search history.

(56) References Cited

U.S. PATENT DOCUMENTS 4,652,827 A    3/1987  Eguchi et al.
5,168,224 A *  12/1992  Maruizumi et al. .......... 324/300

(Continued)

FOREIGN PATENT DOCUMENTS

JP            60-190846          9/1985

(Continued)

OTHER PUBLICATIONS

International Search Report for PCT/JP2006/307667 dated Jul. 18, 2006.

(Continued)

*Primary Examiner* — Brij B Shrivastav
(74) *Attorney, Agent, or Firm* — Rankin Hill & Clark LLP

(57) ABSTRACT

An instrument locally measuring mobility of a protic solvent in a sample 115 based on the gradient magnetic field NMR method has a sample stage 116 on which the sample 115 is placed, a magnet 113 applying a static magnetic field to the sample 115, a G coil 151 and a G coil 153 applying a gradient magnetic field to the sample 115, a small-sized RF coil 114 smaller in size than the G coil 151 applying an oscillating magnetic field for excitation and acquiring an NMR signal corresponded to the oscillating magnetic field for excitation and the gradient magnetic field; a pulse control unit 108 allowing application of the gradient magnetic field and oscillating magnetic field for excitation to be executed according to a predetermined pulse sequence; and an operation unit 130 calculating the mobility at the specific position of the G coil 151, based on information of the NMR signals acquired corresponding to different gradient magnetic fields.

50 Claims, 55 Drawing Sheets

U.S. PATENT DOCUMENTS

| | | | |
|---|---|---|---|
| 5,212,447 A | | 5/1993 | Paltiel |
| 5,572,124 A | * | 11/1996 | Bito et al. .................... 324/307 |
| 5,602,477 A | * | 2/1997 | McCarthy et al. ............ 324/315 |
| 5,629,624 A | * | 5/1997 | Carlson et al. ................ 324/309 |
| 6,100,687 A | * | 8/2000 | Weitekamp et al. .......... 324/300 |
| 7,053,611 B2 | * | 5/2006 | Freedman ..................... 324/303 |
| 2005/0196660 A1 | | 9/2005 | Tsushima et al. |

FOREIGN PATENT DOCUMENTS

| | | |
|---|---|---|
| JP | 07-067849 | 3/1995 |
| JP | 07-151715 | 6/1995 |
| JP | 07-184875 | 7/1995 |
| JP | 2004-061327 | 2/2004 |
| JP | 2004-170297 | 6/2004 |
| JP | 2005-069895 | 3/2005 |

OTHER PUBLICATIONS

Kobunshi-Gakkai et al, Chapter 3 of Kobunshi to Mizu: Jul. 10, 1995.

Stejskal et al, Spin Diffusion Measurements: Spin Echoes in the Presence of a Time-Dependent Field Gradient, Journal of Chemical Physics, vol. 42, No. 1, pp. 288-292.

Kose, NMR Imaging, 2004, pp. 176.

Horikawa et al, Diffusion Weighted Imaging by MR Method, Med. Imag. Tech., Mar. 1993, vol. 11, No. 1, pp. 288-292.

ITO et al, Investigation of Water Molecule Concentration Distribution and Transport Coefficient in Solid Polymer Electrolyte Membrane by Magnetic Resonance Imaging, vol. 68, No. 666, pp. 253-259.

* cited by examiner (a) t=0

(b) t<τ

(c) τ<t (d) t=2τ

(a)

(b)

| | COIL | SELF-DIFFUSION COEFFICIENT [M²/S] |
|---|---|---|
| CASE 1 | SMALL-SIZED SURFACE COIL (SINGLE) | $1.89 \times 10^{-9}$ (SAMPLE TEMPERATURE 14.2°C) |
| CASE 2 | SMALL-SIZED SURFACE COIL (FIRST CHANNEL) | $2.25 \times 10^{-9}$ (SAMPLE TEMPERATURE 17.5°C) |
| | SMALL-SIZED SURFACE COIL (SECOND CHANNEL) | $1.94 \times 10^{-9}$ (SAMPLE TEMPERATURE 17.5°C) |

Analized signal intensity map using Spin Echo
based on Hz and sin(FlipAngle)^3 and detection map
Frip angle=90 degree at xp=0, yp=0, ZP=D/5 using Single Ring Coil

METHOD OF LOCALLY MEASURING MOBILITY OF PROTIC SOLVENT IN SAMPLE, INSTRUMENT OF LOCALLY MEASURING MOBILITY OF PROTIC SOLVENT IN SAMPLE, MEASURING INSTRUMENT LOCALLY MEASURING BEHAVIOR OF PROTIC SOLVENT IN SAMPLE BASED ON MAGNETIC

TECHNICAL FIELD

The present invention relates to a method of locally measuring mobility of a protic solvent in a sample, an instrument of locally measuring mobility of a protic solvent in a sample, a measuring instrument locally measuring behavior of a protic solvent in a sample based on the magnetic resonance method, a method of measurement, and a program.

BACKGROUND ART

In some sort of functional materials, movement of solvent molecules in the materials may govern performances of the materials. In design and development of this sort of materials, local measurement of mobility of the solvent molecules is understood as an important technical issue. This sort of functional material can be exemplified by solid polymer electrolyte film used for fuel cells.

In fuel cells using the solid polymer electrolyte film, power generation characteristics and efficiency strongly depend on ion conductivity of the polymer film. To keep the power generation characteristics at a high level, it is necessary to keep the ion conductivity of the polymer film at a high level. The ion conductivity of the film is induced by movement of hydrogen ion in the film, so that mobility of the hydrogen ion governs the ion conductivity of the polymer film. The hydrogen ion does not move alone in the film, but moves in the film together with water molecules disposed therearound, while canceling the electric charge by the polar water molecules, so as to protect and allow the hydrogen ion to stably exist in the film. The water molecule moves together with hydrogen ion is called "electro-osmotic water (water taranport by electro-osmotic drag)", and plays an important role in keeping the ion conductivity of the polymer film at a high level.

In relation to this transportation mechanism in the polymer film, it is known that the ion conductivity in the polymer film is determined by the amount of water molecules contained in the film (water content of the film) and readiness of movement of water molecules (mobility of water molecules) in the film. More specifically, the amount of water M moving in the solid polymer electrolyte film is expressed, using water content m in the film and mobility v of water molecules, as $$M = mv$$

A technique of locally measuring m has already been proposed by the present inventors (Japanese Patent Application No. 2004-265535).

On the other hand, a technique of measuring "readiness of movement of water molecules (mobility of water molecules) in the film" has not been proposed, with a partial exception, despite its importance to the ion conductivity of the polymer material. In particular, measurement of "mobility of water molecules" is essential in order solve a problem that the amount of power generation sharply decreases in the process of power generation by fuel cells. At present, decrease in the amount power generation is supposedly ascribable to lowering in the ion conductivity or deterioration of catalyst in the polymer film, although definitive evidence remains unknown, demanding a technique of monitoring properties of the film during power generation. In this process, only insufficient information is available simply by a technique of measuring the water content of the film, wherein "causes for degradation of the ion conductivity" can be elucidated by measuring the "mobility of water molecules in the film" at the same time. A guideline for the countermeasure can be obtained only after the elucidating the causes for the degradation.

Other than those described in the above exemplified by the solid polymer electrolyte film used for fuel cells, there are large needs for techniques of measuring mobility of molecules of solvent such as water in solid matrix and gel, wherein these technique of measurement may be key technology for the material development.

There has been developed several techniques of measuring mobility of solvent molecules in solid.

Techniques of measuring "mobility of water molecules" in polymer film includes (i) a technique of measuring "mobility through a film applied with liquid under pressure, based on the amount of permeation" (Non-Patent Document 1). This method is, however, disadvantageous in that "the mobility through the polymer film is not measurable under varied conditions of moistening", because the both surfaces of the film is immersed in water. For the process of power generation in fuel cells, it is necessary to understand not only the situation where the polymer film is immersed in water, but also "mobility of water through the polymer film under different conditions of moistening" which may vary depending on conditions of moistening, but the method cannot alter the conditions of moistening. Moreover, the method is not considered as enabling quick local measurement.

There are also known conventional methods of measuring "mobility of water molecules", such as a method of (ii) "measuring mobility of water molecules in terms of self-diffusion coefficient" based on the nuclear magnetic resonance (NMR) method; and a method of (iii) "measuring mobility of water molecules as being expressed by an image of distribution of self-diffusion coefficient" based on the magnetic resonance imaging (MRI) method. The method (ii) in the above is a publicly-known method described in Non-Patent Document 2, by which the entire portion of a sample is measured, so as to calculate a mean mobility of water molecules.

The method of (iii) "measuring mobility of water molecules as being expressed by an image of distribution of self-diffusion coefficient" in the above is a technique based on combination of MRI and the above-described (ii) so as to provide imaging of the distribution, and is publicly known, similarly to the technique (ii) in the above, as being called "diffusion imaging" (Non-Patent Document 3), or "MR image emphasizing diffusion of water molecules" (Non-Patent Document 4).

[Non-Patent Document 1] "Ko-bunshi to Mizu (Polyer and Water)", edited by The Society of Polymer Science, Japan, Chapter 3

[Non-Patent Document 2] E. O. Stejskal and J. E. Tanner, "Spin diffusion measurements: Spin Echoes in the Presence of a Time-Dependent Field Gradient", Journal of chemical physics, vol. 42, No. 1, 1965, pp. 288-292

[Non-Patent Document 3] NMR Imaging, Katsumi KOSE, Kyoritsu Shuppan Co., Ltd., (2004), p. 176

[Non-Patent Document 4] The 13th JAMIT Seminar (October, 1992, Tokyo), Med. Imag. Tech., Vol. 11, No. 1, 1993, p. 12-21

DISCLOSURE OF THE INVENTION

Of these methods of measurement, (i) is suffering from a drawback in that the method is premised on evaluation of property of polymer film alone, and cannot monitor the film under power generation. Moreover, only a mean value for the entire film is available, while leaving local measurement unavailable.

Even if it should otherwise possible by the method (ii) to measure the film under power generation, the method is still incapable of providing quick measurement enough as fast as measuring the mobility of water molecules in synchronization with conditions of power generation, so that the method is not adoptable as a method of elucidating causes for degradation of power generation performance, and of monitoring for optimum control. These techniques are incapable of quickly measuring locally-changing properties of the film (water content and mobility).

There are therefore needs for techniques allowing measurement of local mobility of protic solvent at a specific position of a substance, within a relatively short time.

In addition, for the purpose of better understanding of lowering in the ion conductivity in the film causative of lowering in the amount of power generation of fuel cells, it is necessary to measure the "content of water molecules" and "mobility of water molecules" in the film at the same position, also raising a need for a technique allowing measurement of "amount of water molecules" and "mobility of water molecules" at the same position.

The present invention is conceived after considering the above-described situation, and is to provide a technique of measuring local mobility of protic solvent at a specific position of a substance, within a relatively short time.

The present invention is to provide also a measuring instrument, method of measurement, and a program, allowing measurement of "the amount of protic solvent" and "mobility of protic solvent" at the same position, and thereby providing better understanding of local behavior or protic solvent in sample.

According to the present invention, there is provided an instrument of locally measuring mobility of a protic solvent in a sample, based on the field-gradient magnetic resonance method, which includes:

a static magnetic field application unit applying a static magnetic field to the sample;

a gradient magnetic field application unit applying a gradient magnetic field to the sample;

a small-sized RF coil smaller in size than the sample, applying an oscillating magnetic field for excitation to the sample, and acquiring a magnetic resonance signal corresponded to the oscillating magnetic field for excitation and the gradient magnetic field;

a control unit applying the gradient magnetic field and the oscillating magnetic field for excitation according to a predetermined pulse sequence; and an operation unit calculating the mobility at a specific position in the sample, based on information of the magnetic resonance signals obtained corresponding to different gradient magnetic fields.

According to the present invention, there is also provided a method of locally measuring mobility of a specific position of a sample based on the field-gradient magnetic resonance method, which includes:

a first step applying an oscillating magnetic field for excitation to the sample according to a predetermined pulse sequence;

a second step acquiring a magnetic resonance signal corresponded to the pulse sequence in the first step;

a third step applying an oscillating magnetic field for excitation and gradient magnetic field to the sample according to a predetermined pulse sequence;

a fourth step acquiring a magnetic resonance signal corresponded to the pulse sequence in the third step; and a fifth step calculating mobility of a specific position of the sample, based on information on the magnetic resonance signal obtained in the second step, and information on the magnetic resonance signal obtained in the fourth step, wherein, in the first step and the third step, a local magnetic field is applied to a specific position of the sample, using a small-sized RF coil smaller in size than the sample, and in the second step and the fourth step, the magnetic resonance signal is acquired from the specific position of the sample, using the small-sized RF coil smaller than the sample.

In the present invention, using a small-sized RF coil, (i) an oscillating magnetic field for excitation and gradient magnetic field is locally applied, and (ii) a magnetic resonance signal (for example, an NMR signal) emitted from the portion applied with an oscillating magnetic field for excitation and a gradient magnetic field is acquired, to thereby measure the mobility at a specific position of the sample, based on the magnetic resonance signals obtained corresponding to different gradient magnetic fields. Because the spin-echo method and the gradient field magnetic resonance signal method are adopted while limiting the portion to be measured using the small-sized RF coil, local mobility of the protic solvent in a predetermined region can be measured within a short time.

The "mobility" measured by the present invention is a physical value expressing readiness of movement of protic solvent in sample. This sort of physical value may be exemplified by parameters such as self-diffusion coefficient, and mobility (moving speed). According to the present invention, any one of these parameters can be obtained.

The "magnetic resonance" in the context of the present invention includes both of nuclear magnetic resonance (NMR) and electron spin resonance (ESR). Of these, by adopting the method of measurement based on nuclear magnetic resonance, behavior of protic solvent at a specific position in a sample can stably be measured, as described later in preferred embodiments.

The present invention may be configured so that the sample contains a matrix composed of a solid or a gel; and the operation unit calculates the mobility of the protic solvent in the matrix. This sort of sample may be exemplified by a moisture-containing film, such as solid electrolyte film typically used for fuel cells. By measuring the mobility in this sort of film, performance of the film can appropriately be understood. In particular, for the case where the method is adopted to measurement of solid electrolyte film of fuel cells, mobility of protic solvent molecules in the solid electrolyte film can be measured under the condition of power generation. In the present invention, another possible configuration is such that the sample is a liquid containing a protic solvent, and the operation unit calculates the mobility of protic solvent in the liquid.

The protic solvent in the context of this patent specification refers to a solvent capable of producing protons by self-dissociation. The protic solvent can be exemplified by:
water;
alcohols such as methanol and ethanol;
carboxylic acid such as acetic acid;
phenol; and
liquid ammonia.
Of these, water and alcohols allow more stable measurement of mobility in the present invention.

In the present invention, the term "different gradient magnetic fields" also includes the case where one of which has no magnetic gradient, in other words, the measurement was carried out without applying the gradient magnetic field.

In the present invention, the "pulse sequence" is a sequence specifying a timing diagram according to which timing and intervals of application of the oscillating magnetic field for excitation and the gradient magnetic field are set. The timing diagram also includes a table of procedures used for time-series execution of necessary operations.

The gradient magnetic field application unit in the present invention may be embodied in various ways. For example, it may be configured as a gradient magnetic field coil disposed apart from the small-sized RF coil, or may be configured as a planar coil provided in the same plane with the small-sized RF coil. It may be configured also as a pair of gradient magnetic field coils disposed while placing the small-sized RF coil in between. It may be configured still also by combining these configurations.

In the present invention, the pair of gradient magnetic field coils may have a near-semicircular planar geometry, and are opposingly disposed so as to face the individual chords of semicircle towards the small-sized RF coil. This configuration allows high-precision local measurement while achieving space saving. The near-semicircular in the context of this patent specification means that each of the pair of planar coils have a chord-like linear region, and that opposed disposition thereof allows application of a gradient magnetic field, inclined in the direction normal to the linear regions, to the sample. The semi-circular planar geometry of the coil may be larger or smaller than the semicircle, so far as they can apply such gradient magnetic field.

In the present invention, the instrument may be configured as having a plurality of the small-sized RF coils, wherein the plurality of small-sized RF coils may apply the oscillating magnetic field for excitation to a plurality of positions of the sample, and may acquire NMR signals corresponded to the oscillating magnetic field for excitation and the gradient magnetic field, and the operation unit may calculate the mobility at the plurality of position of the sample. This configuration allows a multi-point simultaneous measurement only with a simple configuration. Arrangement of the plurality of small-sized RF coils may be arbitrary, allowing an arrangement in an array depending on the geometry of an object to be measured.

In the present invention, the small-sized RF coil may be configured as applying the oscillating magnetic field for excitation according to a pulse sequence composed of:

(a) a 90° pulse; and
(b) a 180° pulse applied time τ after the pulse of (a)

By this configuration, the mobility can more precisely be determined.

In addition to the above-described pulse sequence, it is also allowable to execute another sequence added with a step applying a 180° pulse time τ earlier than the 90° pulse. By comparing intensity of an NMR signal obtained with the aid of the 90° pulse (a) and intensity of an NMR signal obtained with the aid of the 180° pulse (b), whether the intensity of the oscillating magnetic field for excitation emitted from the RF coil is exactly corresponded to 90°, 180° or not. To keep intensities of two these pulses at a relation of 1:2, and to excite the magnetization vectors respectively at angles of 90° and 180° are important factors for improving the probability and reproducibility of the measured values. As a consequence, even if the relation between two these pulses becomes inappropriate due to abnormalities in the instrument or unskilled adjustment, abnormalities are detectable before the measurement, and the measured value can be made more probable.

The present invention adopts a configuration of locally applying the spin echo method and the gradient magnetic field NMR method to a specific position of a sample, so that local mobility of protic solvent at the specific position of the sample can be measured within a short time.

The present invention having been described in the above is to measure local mobility of protic solvent in sample, and is adoptable to various technical field having such needs. For example, it is adoptable to a technique of measuring, in a real-time manner, local mobility of protic solvent in a solid electrolyte film in operational control of hydrogen-supply-type fuel cells, and to a technique of controlling the amount of water supply into the fuel, or controlling operational conditions of fuel cells, based on thus-measured mobility of protic solvent.

In addition, according to the present invention, there is provided an instrument of measuring behavior of a protic solvent at a specific position of a sample based on the magnetic resonance method, which includes:

a static magnetic field application unit applying a static magnetic field to the sample;

a gradient magnetic field application unit applying a gradient magnetic field to the sample;

a small-sized RF coil smaller in size than the sample, applying an oscillating magnetic field for excitation to the sample, and acquiring a magnetic resonance signal generated at the specific position of the sample;

a measurement mode selecting unit selecting anyone of a plurality of measurement modes including a first measurement mode allowing measurement of the amount of protic solvent at the specific position of the sample, and a second measurement mode allowing measurement of mobility of protic solvent at the specific position of the sample;

a control unit controlling operation of the small-sized RF coil and the gradient magnetic field application unit, according to the measurement mode selected by the measurement mode selecting unit;

a first calculation unit calculating the amount of protic solvent at the specific position of the sample, according to the magnetic resonance signal acquired in the first measurement mode; and a second calculation unit calculating the mobility of protic solvent at the specific position of the sample, according to the magnetic resonance signal acquired in the second measurement mode;

the control unit being configured:

so as to apply, while being in the first measurement mode, an oscillating magnetic field for excitation through the small-sized RF coil, to the specific position of the sample, and to acquire, through the small-sized RF coil, the magnetic resonance signal generated at the specific position corresponded to the oscillating magnetic field for excitation, and so as to apply, while being in the second measurement mode, an oscillating magnetic field for excitation through the small-sized RF coil, to the specific position of the sample, and also a gradient magnetic field by the gradient magnetic field application unit, and to acquire, through the small-sized RF coil, the magnetic resonance signal generated corresponding to these magnetic fields.

According to the present invention, there is also provided a method of measuring the amount of protic solvent at a specific position of a sample, and the mobility of protic solvent at the specific position, based on the magnetic resonance method, using a measuring instrument having a static magnetic field application unit applying a static magnetic field to the sample; a gradient magnetic field application unit applying a gradient magnetic field to the sample; and a small-sized RF coil smaller in size than the sample, applying an oscillating magnetic field for excitation to the sample, and acquiring a magnetic resonance signal corresponded to the oscillating magnetic field for excitation and the gradient magnetic field, which includes:

measuring the amount of protic solvent, by selecting a first measurement mode allowing measurement of the amount of protic solvent, and by applying the oscillating magnetic field for excitation; and measuring the mobility of protic solvent, by selecting a second measurement mode allowing measurement of mobility of protic solvent, and by applying the gradient magnetic field and the oscillating magnetic field for excitation according a predetermined pulse sequence, the measuring the protic solvent further includes:

sequentially applying, a plural number of times, an oscillating magnetic field for excitation to a specific position of the sample placed in the static magnetic field, using the small-sized RF coil, and acquiring a plurality of magnetic resonance signals corresponded to the oscillating magnetic field for excitation; and determining the amount of protic solvent at the specific position of the sample, based on intensity of the magnetic resonance signal;

the measuring the mobility further includes:

a first step applying an oscillating magnetic field for excitation to a specific position of the sample placed in a static magnetic field, using the small-sized RF coil, according to a predetermined pulse sequence;

a second step acquiring the magnetic resonance signal corresponded to the pulse sequence in the first step, using the small-sized RF coil;

a third step applying an oscillating magnetic field for excitation and a gradient magnetic field to the specific position of the sample, according to a predetermined pulse sequence;

a fourth step acquiring the magnetic resonance signal corresponded to the pulse sequence in the third step, using the small-sized RF coil; and a fifth step calculating the mobility of protic solvent at the specific position of the sample, based on the magnetic resonance signal obtained in the second step, and the magnetic resonance signal obtained in the fourth step.

According to the present invention, there is also provided a program executing, by controlling a measuring instrument having a static magnetic field application unit applying a static magnetic field to the sample; a gradient magnetic field application unit applying a gradient magnetic field to the sample; and a small-sized RF coil smaller in size than the sample, applying an oscillating magnetic field for excitation to the sample, and acquiring a magnetic resonance signal corresponded to the oscillating magnetic field for excitation and the gradient magnetic field, measuring the amount of protic solvent, by selecting a first measurement mode allowing measurement of the amount of protic solvent of the sample, and by applying the oscillating magnetic field for excitation; and measuring the mobility of protic solvent, by selecting a second measurement mode allowing measurement of mobility of protic solvent of the sample, and by applying the gradient magnetic field and the oscillating magnetic field for excitation according a predetermined pulse sequence, the measuring the protic solvent further includes:

sequentially applying, a plural number of times, an oscillating magnetic field for excitation to a specific position of the sample placed in the static magnetic field, using the small-sized RF coil, and acquiring a plurality of magnetic resonance signals corresponded to the oscillating magnetic field for excitation; and determining the amount of protic solvent at the specific position of the sample, based on intensity of the magnetic resonance signal;

the measuring the mobility of protic solvent further a first step applying an oscillating magnetic field for excitation to a specific position of the sample placed in a static magnetic field, using the small-sized RF coil, according to a predetermined pulse sequence;

a second step acquiring the magnetic resonance signal corresponded to the pulse sequence in the first step, using the small-sized RF coil;

a third step applying an oscillating magnetic field for excitation and a gradient magnetic field to the specific position of the sample, according to a predetermined pulse sequence;

a fourth step acquiring the magnetic resonance signal corresponded to the pulse sequence in the third step, using the small-sized RF coil; and a fifth step calculating the mobility of protic solvent at the specific position of the sample, based on the magnetic resonance signal obtained in the second step, and the magnetic resonance signal obtained in the fourth step.

According to the above-described present invention, in the measurement mode allowing measurement of the amount of protic solvent, the amount of protic solvent at a specific position can be measured by limiting a target portion to be measured, using the small-sized RF coil smaller in size than the sample. Also in the measurement mode allowing measurement of mobility, the mobility at the specific position can be measured by limiting a target portion to be measured, using the gradient magnetic field application unit and the small-sized RF coil.

As a consequence, the amount of protic solvent and the mobility of protic solvent can be measured at the same position of the sample, and thereby local behavior of protic solvent in the sample can exactly be understood.

The "behavior of protic solvent" measurable herein by the present invention may be exemplified by the amount of protic solvent, mobility of protic solvent, and amount of movement of protic solvent.

The "mobility" measurable herein by the present invention means a physical value expressing readiness of movement of protic solvent in sample. This sort of physical value may be exemplified by parameters such as self-diffusion coefficient, and mobility (moving speed).

As described previously, the protic solvent in the context of this patent specification refers to a solvent capable of producing protons by self-dissociation, wherein use of water or alcohols as the protic solvent allows more stable measurement of the amount of protic solvent and the mobility of protic solvent in the present invention.

The static magnetic field in the present invention is not necessarily completely stable, but may be stable with time only to a degree allowing stable acquisition of the magnetic resonance signal, allowing some degree of fluctuation within such range.

Application of magnetic field in the first measurement mode is not limited to application of the oscillating magnetic field for excitation using the small-sized RF coil. For example, a minute level of gradient magnetic field having a gradient of only as small as zero may be applied.

For an exemplary case where the amount of protic solvent is measured by the Carr-Purcell-Meiboom-Gill method (abbreviated as CPMG method, hereinafter), "FID contamination (Interference with echo signal and FID)" (unnecessary magnetic resonance signal received after application of a 180° pulse, when the oscillating magnetic field for excitation is applied using a 90° pulse and the 180° pulse) may be observed, if the sample was not applied with the oscillating magnetic field for excitation in a uniform manner at an ideally appropriate intensity. To eliminate the nonconformity, one effective operation may be such as applying a short gradient magnetic field before and after the 180° pulse so as to intentionally disturb the phase of magnetization vector of the unnecessary signal, to thereby "erase (spoil) the contamination". This operation is effective particularly for the case of using a sample containing a lot of water, a good emitter of magnetic resonance signals, or the small-sized RF coil.

For the case where the small-sized RF coil is used, intensity of the oscillating magnetic field for excitation emitted from the coil will vary depending on the distance from the small-sized RF coil, without uniformly exciting the sample over the entire portion thereof. For this reason, the unnecessary magnetic resonance signal is observed after the 180° pulse, more intensely than in the case where a solenoid coil capable of uniform excitation is used. Operation of applying a short gradient magnetic field before and after the 180° pulse (spoiling) is, therefore, effective as a method of moderating the nonconformity.

In the second measurement mode, the predetermined pulse sequence, based on which the gradient magnetic field and the oscillating magnetic field for excitation are applied, is a sequence specifying a timing diagram according to which timing and intervals of application of the oscillating magnetic field for excitation and the gradient magnetic field are set.

The measuring instrument of the present invention herein may have a third calculation unit calculating the amount of movement of protic solvent, based on the amount of protic solvent calculated by the first calculation unit, and the mobility of protic solvent calculated by the second calculation unit. Provision of the third calculation unit makes it possible to understand local amount of movement of protic solvent.

The measuring instrument of the present invention may have a support supporting the small-sized RF coil and the gradient magnetic field application unit.

By supporting the small-sized RF coil and the gradient magnetic field application unit on the same support, measurement of the amount of protic solvent of the sample is accessible if the support is brought close to the sample. The measuring instrument, therefore, becomes more convenient to use.

In the present invention, the static magnetic field application unit may be attached to the support.

By attaching, not only the small-sized RF coil and the gradient magnetic field application unit, but also the static magnetic field application unit to the support, the measuring instrument becomes more convenient to use.

In the present invention, the support may have a stick-like form, and may have the small-sized RF coil and the gradient magnetic field application unit attached to the end portion thereof.

The stick-like support herein is not limited to those having a straightly extending geometry, but may be those having a kinked geometry such as L-shape or U-shape.

By shaping the support into stick form, the operator can carry out the measurement simply by holding the support and bringing the end portion of the support close to the specific position of the sample.

In the present invention, the small-sized RF coil may be projected towards the sample side, out from the gradient magnetic field application unit.

In the present invention, the gradient magnetic field application unit may be configured as being adjustable in the relative position with respect to said small-sized RF coil. For example, the measuring instrument may be configured as having a support having the small-sized RF coil and the gradient magnetic field application unit attached thereto, wherein the support may have a main unit having the gradient magnetic field application unit attached to the end portion thereof, and a moving component movable back and forth in a hole formed in the end portion of the main unit, wherein the moving component may have, on the end portion thereof located on the sample side, the small-sized RF coil.

In the present invention, the measuring instrument may have a plurality of the small-sized RF coils, wherein the gradient magnetic field application unit may have a plurality of gradient magnetic field coils, and the gradient magnetic field coils and the small-sized RF coils may alternately be disposed.

By alternately disposing a plurality of small-sized RF coils and a plurality of gradient magnetic field coils, it becomes possible to measure distribution of, for example, the amount of protic solvent in the sample.

By virtue of the alternate disposition of a plurality of small-sized RF coils and gradient magnetic field coils, now the gradient magnetic field coil disposed between a pair of small-sized RF coils can apply the gradient magnetic field to the a pair of small-sized RF coil.

The measuring instrument of the present invention may still further be such as having a unit having at least one of the small-sized RF coils and one of the gradient magnetic field coils, wherein a plurality of the units may be disposed to thereby alternately dispose the gradient magnetic field coils and the small-sized RF coils.

In the measuring instrument of the present invention, the first calculation unit may further have an estimation unit calculating an estimated value of the amount of protic solvent based on intensity of the magnetic resonance signal; and a correction unit calculating the amount of protic solvent, by correcting the estimated value of the amount of protic solvent in a manner adapted to the size of the small-sized RF coil. In this case, the measuring instrument preferably has a storage unit having, stored therein, correction parameters or correction equations used for correcting the estimated value of the amount of protic solvent calculated by the estimation unit, in a manner adapted to the size of the small-sized RF coil, and the correction unit preferably reads the correction parameters or correction equations out from the storage unit, and corrects the estimated value of the amount of protic solvent, to thereby calculate the amount of protic solvent.

Moreover, the second calculation unit may have an estimation unit calculating an estimated value of mobility, based on the magnetic resonance signal obtained by applying the oscillating magnetic field for excitation and the gradient magnetic field; and a correction unit calculating the mobility, by correcting the estimated value of mobility in a manner adapted to the size of the small-sized RF coil. In this case, the measuring instrument preferably has a storage unit having, stored therein, correction parameters or correction equations used for correcting the estimated value of mobility calculated by the estimation unit, in a manner adapted to the size of the small-sized RF coil, and the correction unit preferably reads the correction parameters or correction equations out from the storage unit, and corrects the estimated value of mobility, to thereby calculate the mobility.

In the process of acquisition of the magnetic resonance signals using the small-sized RF coil, interference between unnecessary magnetic resonance signal and an echo signal to be measured supposedly lower probability of the measurement, and thereby variation in the measurement increases. It is therefore considered that the observed results of the mobility and the amount of protic solvent increase or decrease, depending on size or geometry of the small-sized RF coil, such as ratio of the outer diameter and the inner diameter of the small-sized RF coil.

In contrast to this, according to the above-described configuration, the estimated value of mobility and the estimated value of the amount of protic solvent are corrected in a manner adapted to the size of the small-sized RF coil, so that the mobility and the amount of protic solvent can exactly be understood.

The measuring instrument may further have an RF excitation pulse generating unit generating an RF excitation pulse raising the oscillating magnetic field for excitation around the small-sized RF coil; a magnetic resonance signal detecting unit detecting the magnetic resonance signal acquired by the small-sized RF coil, and sending out the magnetic resonance signal to the first calculation unit or the second calculation unit; and a switching circuit provided at a branching portion where the small-sized RF coil, the RF excitation pulse generating unit and the magnetic resonance signal detecting unit are connected, allowing switching between the state having the small-sized RF coil and the RF excitation pulse generating unit connected with each other, and the state having the small-sized RF coil and the magnetic resonance signal detecting unit connected with each other.

By virtue of this configuration, loss of RF pulse for excitation applied from the small-sized RF coil to the sample may be increases.

In the present invention, the small-sized RF coil is preferably a planar coil, and preferably has inner diameter/outer diameter of the small-sized RF coil of 0.65 or larger, and 1 or smaller.

According to the present invention described in the above, the "amount of protic solvent" and the "mobility of protic solvent" can be measured at the same position of the sample, so that the local behavior of protic solvent in the sample can exactly be understood. For example, in operational control of hydrogen-supply-type fuel cells, the present invention is preferably applicable to a technique of measuring the local mobility of protic solvent and the amount of protic solvent in the solid electrolyte film, and to a technique of controlling the amount of water supply into the fuel, or controlling operational conditions of fuel cells, based on thus-measured mobility of protic solvent and the amount of protic solvent.

BRIEF DESCRIPTION OF THE DRAWINGS

The above and other objects, features and advantages will be more apparent from the following description of certain preferred embodiments taken in conjunction with the accompanying drawings.

BEST MODES FOR CARRYING OUT THE INVENTION

Figure 1:
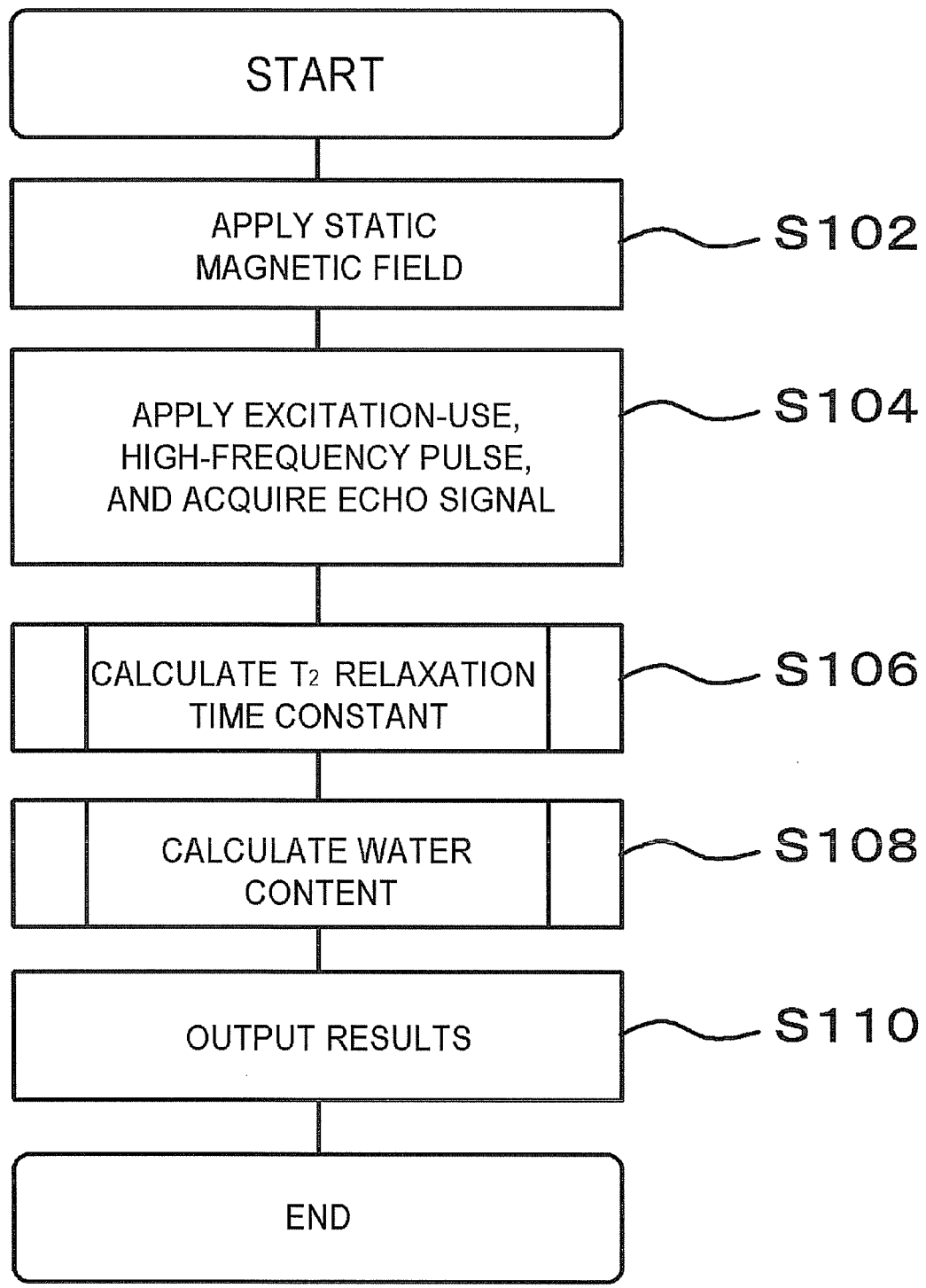
FIG. 1 is a flow chart showing an outline of the method of local measurement of water content.

Next, details of the present invention will be explained in conjunction with embodiments. In all drawings referred in the embodiments, any similar constituents will be given with similar reference numerals, and the explanation therefor will not be repeated.

(Principle of Measurement)

First of all, a principle of measurement of water content (protic solvent content) in the individual embodiments described later will be explained, referring to specific examples.

First, calculation of water content will be explained.

(A) Calculation of Water Content

FIG. 1 is a flow chart showing an outline of calculation of water content.

First of all, a sample is placed in a space having magnets arranged therein, and a static magnetic field is applied to the sample (S102).

while keeping this state, the sample is applied with an oscillating magnetic field for excitation, and a correspondent NMR signal (echo signal) is acquired (S104). The oscillating magnetic field for excitation is RF pulses irradiated to a target nucleus to be measured in the sample, and the NMR signal is a signal emitted from the target nucleus to be measured in the sample, based on nuclear magnetic resonance phenomenon caused by the oscillating magnetic field for excitation.

Next, $T_2$ relaxation time constant is calculated from the echo signal (S106).

Based on the $T_2$ relaxation time constant, local water content in the sample is measured (S108). More specifically, data indicating correlation between the water content in the sample and the $T_2$ relaxation time constant is acquired, and based on the data and the above-described $T_2$ relaxation time constant, local water content at a specific position in the sample is determined. Thereafter, the results are output (S110).

Step 104 to step 108 will be detailed below.

(i) Step 104 (Application of RF Pulse for Excitation and Acquisition of NMR Signals)

Step 104 will be detailed below. In step 104, the sample is applied with an RF pulse for excitation, wherein the RF pulse for excitation is preferably a pulse sequence composed of a plurality of pulses, and the a correspondent echo signal group is preferably acquired. By this configuration, $T_2$ relaxation time constant can more precisely be determined. The pulse sequence is preferably composed of (a) and (b) below:

(a) a 90° pulse; and
(b) n 180° pulses applied time τ after the pulse of (a) at intervals of time 2τ.

In this embodiment, $T_2$(transverse) relaxation time constant is calculated based on the CPMG method.

A hydrogen nucleus placed in a static magnetic field has a net magnetization vector in the direction along the static magnetic field (referred to as the Z-direction for the convenience sake). When an RF wave of a specific frequency (referred to as resonance frequency) is externally irradiated in the direction of the X-axis, normal to the Z-axis, the magnetization vector inclines in the positive direction of the Y-axis, and allows observation of a nuclear magnetic resonance signal (referred to as NMR signal).

First, the magnetization vector is inclined by a 90° pulse to the positive direction of the Y-axis, then τ time later, a 180° pulse for excitation is externally irradiated in "the direction of Y-axis", to thereby invert the magnetization vector "assuming the Y-axis as the axis of symmetry". As a consequence, 2τ time later, the magnetization vector converges on the Y-axis on the "positive side" thereof, wherein an echo signal having a large amplitude is observed. Further 3τ time after, the magnetization vector is externally irradiated by a 180° pulse for excitation in the "direction of the Y-axis", to thereby allow the vector to converge again on the Y-axis on the "positive side" thereof, wherein an echo signal having a large amplitude is observer 4τ time later. The irradiation of a 180° pulse is similarly continued at 2τ intervals. By extracting peak intensities of even-numbered echo signals at 2τ, 4τ, 6τ and so on, and by fitting them with an exponential function, $T_2$ (transverse) relaxation time constant by the CPMG method may be calculated.

Figure 2:
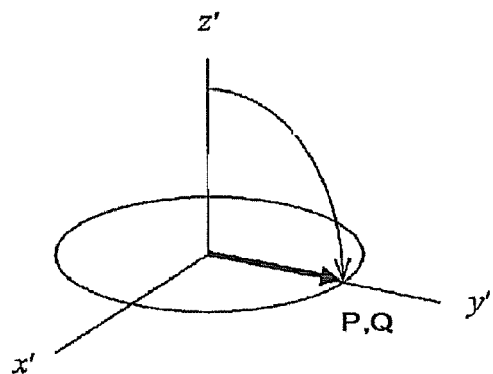
FIG. 2 is a drawing explaining a compensation function of the spin echo method.
Figure 2:
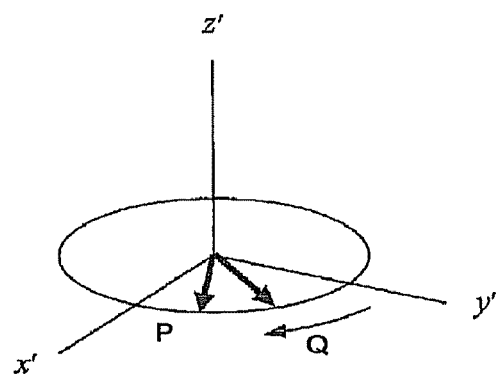
Figure 2:
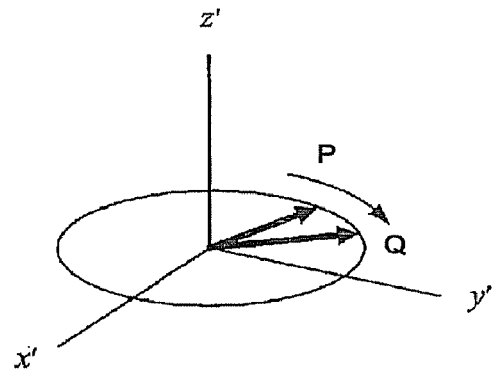
Figure 2:
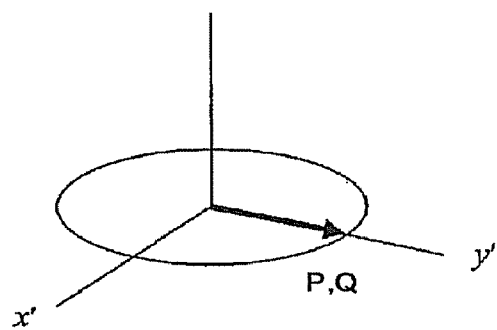

Because the magnetization vector is inverted assuming "the Y-axis as the axis of symmetry" in this embodiment as described in the above, a compensation function as described in the next may express. FIG. 2 is a drawing explaining the compensation function obtainable by the CPMG method in this embodiment. The coordinate system shown in the drawing is a rotatory coordinate system. Considering now, in the sample, P and Q as nuclear magnetization in regions as small enough as non-uniformity in static magnetic field is negligible. Magnetic field at P is assumed as being stronger than magnetic field at Q. In this case, as shown in FIG. 2(a), when a 90° pulse is applied in the direction of the x'-axis, nuclear magnetization P, Q start precession at the same position (the y'-axis) in the rotatory coordinate system, and phase of P advances ahead of phase of Q with the elapse of time (FIG. 2(b)). If a 180° pulse is applied in the direction of the y'-axis time τ after the 90° pulse, the nuclear magnetization P, Q rotate by 180° around the y'-axis, and are positioned symmetrically about the y'-axis with respect to the position before the pulse application (FIG. 2(c)). In this arrangement, nuclear magnetization P having been more advanced in the phase is now delayed behind Q, so that at the point of time after the elapse of time τ, both nuclear magnetization reach the y'-axis at the same time (FIG. 2(d)). Because this relation establishes for nuclear magnetization at all regions in the sample, all nuclear magnetization concentrate on the y'-axis at this point of time, thereby producing a large NMR signal.

As described in the above, in this embodiment, a 90° pulse is first applied in the direction of the x'-axis, and then a 180° pulse is applied in the direction of the y'-axis, so that nuclear magnetization P, Q invert within the x'y'-plane as shown in FIG. 2(c). By virtue of this inversion of nuclear magnetization, the compensation function may desirably be expressed. For example, even if the positions of P, Q should shift upward or downward in the x'y'-plane, due to non-uniformity in the magnetic field, or non-uniformity in the intensity of pulse for excitation emitted from the RF coil, the shift can be compensated by inversion of the nuclear magnetization in the x'y'-plane.

(ii) Step 106 (Measurement of $T_2$ Relaxation Time Constant)

Figure 3:
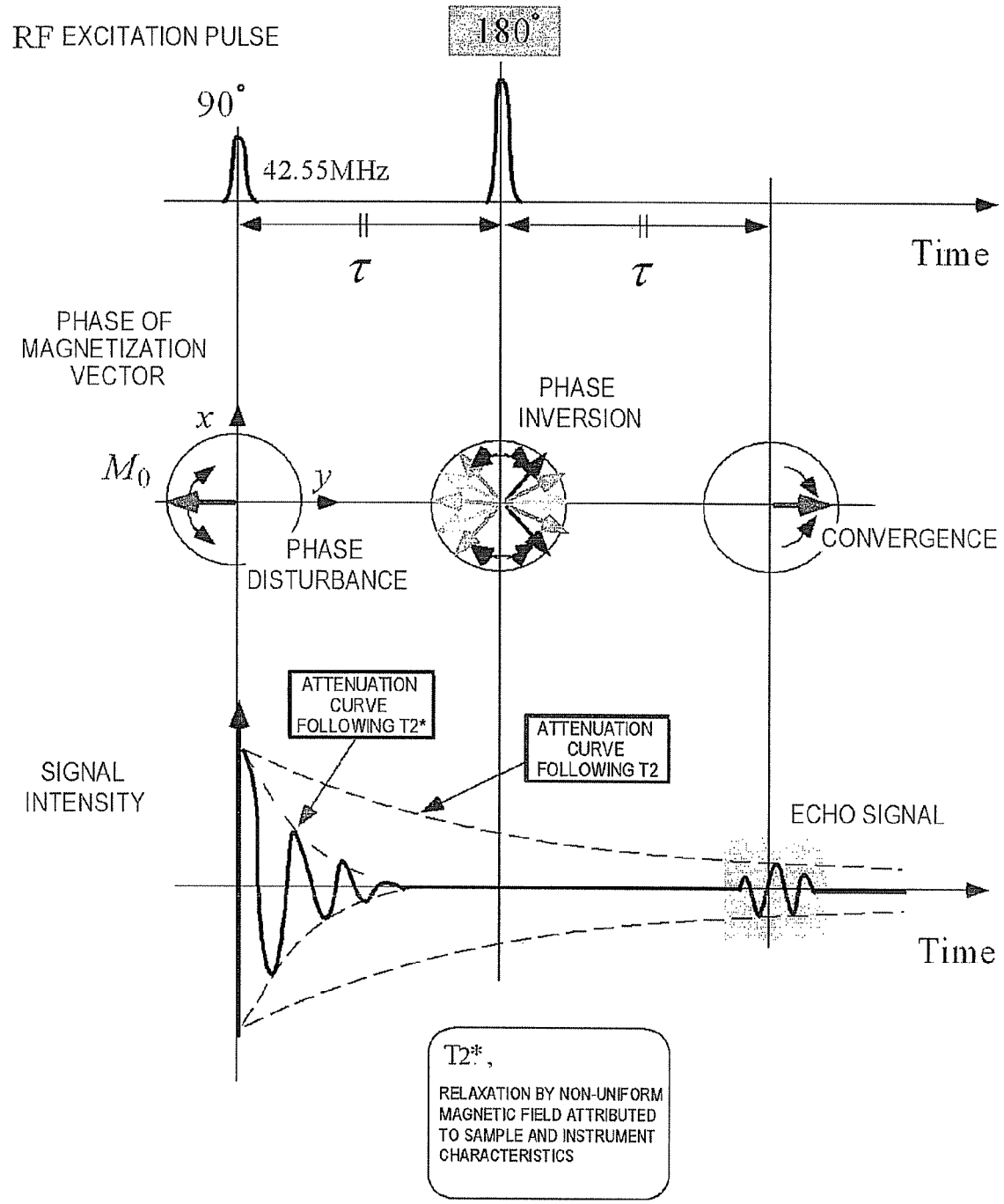
FIG. 3 is a drawing explaining a principle of measurement of $T_2$ relaxation time constant by the spin echo method.

The $T_2$ relaxation time constant can appropriately be measured, based on the spin echo method (FIG. 3).

Resonantly excited magnetization vector $M_{-y}$ relaxes with time. Time-dependent changes in the magnetic resonance signal actually observed in this process relax conform to some other time constant $T_2^*$ which cannot be expressed only by spin-lattice relaxation time constant $T_1$ and spin-spin relaxation time constant $T_2$. The situation in this process is shown in the bottom of FIG. 3, as time-dependent changes in the signal intensity, as being started immediately after the 90° pulse for excitation. The reason why the actually observed attenuation curve attenuates more rapidly than the attenuation curve based on the $T_2$ relaxation resides in that a uniform magnetic field is not ensured over the entire range of the sample, due to non-uniformity in the external static magnetic field generated by the static magnetic field magnet, and non-uniformity in the magnetic field in the sample ascribable to the magnetic properties and geometry.

"Spin echo" is one known method of correcting the shifting of phase due to non-uniformity in the magnetic field as a result of characteristics of the sample or instrument. This is a technique of applying, time τ after a 90° pulse for excitation, a 180° pulse for excitation having doubled intensity, so as to make the magnetization vector M inverted in disturbance of phase, in the process of causing disturbance in phase in the xy-plane, and to make the phase converged 2 τ time after, to thereby obtain an echo signal fitted to the $T_2$ attenuation curve.

Intensity $S_{SE}$ of the echo signal based on the spin echo, if TR≫TE, is given by the equation (A) below:

(Mathematical Formula 1)

$$S_{SE} = A \cdot \rho(x, y, z) \cdot \left\{1 - \exp\left(-\frac{TR}{T_1}\right)\right\} \cdot \exp\left(-\frac{TE}{T_2}\right) \quad \text{Equation (A)}$$

where, ρ represents density distribution of a target nucleus as a function of position (x, y, z), TR represents repetition time (100 ms to 10 s or around) of 90° pulse for excitation, TE represents echo time (2t, 1 ms to 100 ms or around), and A represents a constant expressing detection sensitivity of the RF coil and characteristics of instruments such as amplifier.

The $T_2$ relaxation time constant can be determined using echo signal groups which fall on the $T_2$ attenuation curve and the equation (A) in the above.

(iii) Step 108 (Measurement of Water Content)

In step 108, the water content is calculated using the relaxation time constant. The water content in the sample and the $T_2$ relaxation time constant are in a positive correlation. As the water content increases, the $T_2$ relaxation time constant increases. This correlation varies depending on types and geometries of the sample, so that it is preferable to preliminarily prepare an analytical curve using samples having known moisture concentration, similar to the target sample to be measured. In other words, it is preferable to preliminarily determine the analytical curve. More specifically, it is preferable to measure relations between the water content and the $T_2$ relaxation time constant using a plurality of standard samples having known water contents, and to preliminarily determine an analytical curve expressing the relations. Referring to thus-prepared analytical curve, the water content in the sample can be calculated based on measured values of the $T_2$ relaxation time constant.

Calculation of the mobility will be explained below.

(B) Calculation of Mobility

Based on the nuclear magnetic resonance (NMR) method, (a) local measurement using a small-sized surface coil; and (b) measurement of self-diffusion coefficient of water molecules based on the gradient magnetic field NMR method, are carried out, to thereby locally measure "mobility of protic solvent molecules" expressing properties of the polymer film within a short period of time. The "gradient magnetic field NMR method" may also be referred to as the PGSE method, flow encode pulse, motion-detective gradient field or the like, all of which being techniques of actualizing motion of the molecules making use of the gradient magnetic field, wherein in the embodiment described hereinafter these are represented by the PGSE method. The methods (a) and (b) in the above will be detailed in the next.

(a) Local Measurement Using Small-Sized SuRF Ace Coil

The nuclear magnetic resonance (NMR) method can measure atomic density and the spin-spin relaxation time constant, by detecting motion of nuclear magnetization as an NMR signal as a result of spin resonance phenomenon of atomic nuclei placed in a magnetic field, and can measure the "self-diffusion coefficient of the target molecule by applying the gradient magnetic field". In a 1-Tesla magnetic field, the spin resonance frequency is approximately 43 MHz (in this embodiment, this frequency band is occasionally referred to as "radio frequency"), wherein an LC oscillation circuit is used for selectively detecting the frequency band with high sensitivity.

Figure 14:
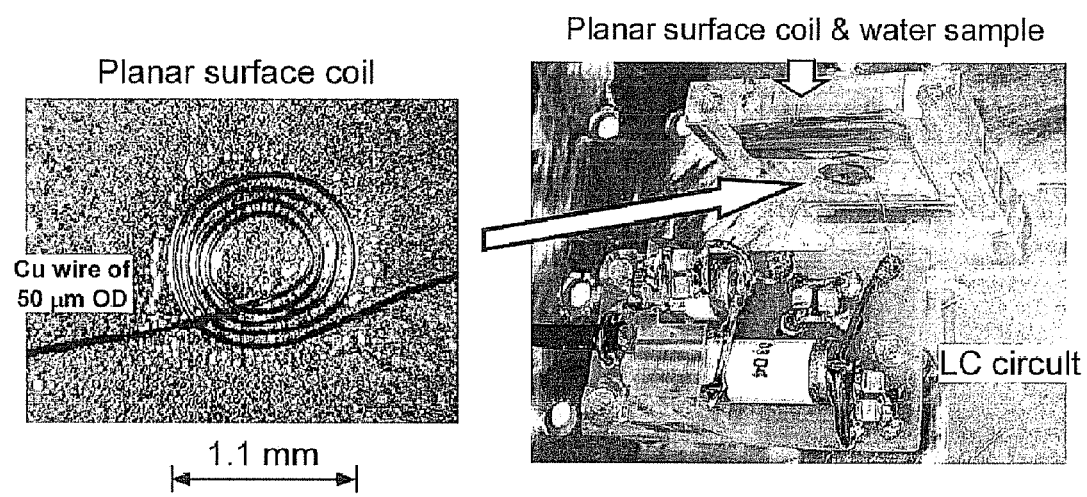
FIG. 14 is a drawing showing an exemplary small-sized RF coil of the mobility measuring instrument according to this embodiment.

FIG. 14 is a drawing showing an exemplary configuration of a coil unit (FIG. 15) in an LC oscillation circuit described later in a first embodiment. As shown in FIG. 14, by composing the coil unit (inductance unit) of the oscillation circuit with a small-sized surface coil, and further by adopting a planar "spiral" coil as shown on the left of FIG. 14, the region to be measured can be limited so as to allow local measurement. The region to be measured using this sort of spiral coil is approximately as wide as the diameter of the coil, and as deep as the radius of the coil. Unlike the general solenoid coils, this coil having a flat geometry can acquire the NMR signal, simply by bonding it on the flat sample as shown by the photograph on the right of FIG. 14.

(b) Measurement of Self-Diffusion Coefficient of Water Molecules Based on the PGSE (Pulsed-Gradient Spin-Echo) Method The PSGE method is adopted herein as a method of measuring the self-diffusion coefficient.

When a specific nuclear spin in the liquid molecule was excited by magnetic resonance, and then a pair of gradient magnetic field pulses (pulsive gradient magnetic field) are applied after an interval of several tens milliseconds, the individual atomic nuclei in this process move by Brownian motion or diffusion, so that the phase of nuclear spin does not converge, and thereby the NMR signal intensity decreases. In this process, the self-diffusion coefficient of a specific molecular species can be calculated, by correlating step-wisely-varied gradient magnetic field pulses with decrease in the NMR signal intensity. This is a principle of measurement of self-diffusion coefficient based on the PGSE method.

Exemplary procedures of measurement by the PGSE method will be shown.

(a1) a pair of positive/negative pulses of current of approximately 1 to 10 A, for example, is applied to a "gradient magnetic field coil" disposed around a sample, for a certain period of time, approximately 1 to 10 ms or around.

(b1) By the procedure (a1), a pair of positive/negative magnetic field distributions, spatially having a certain gradient in any one of x, y and z directions, only for a predetermined duration of time, are formed. For an exemplary distribution in the x-direction, the magnetic field H is written $$H=H_0+G(x-x_0) \quad (I)$$

where, G represents gradient of the magnetic field expressed in T/m. The positive/negative pair herein means gradients of $+G$ and $-G$. $H_0$ represents intensity of uniform magnetic field stabilized on the time basis.

(c1) The NMR signal is acquired under the pair of positive/negative gradient fields described in procedure (b1), and the self-diffusion coefficient D is calculated based on the signal intensity.

Figure 4:
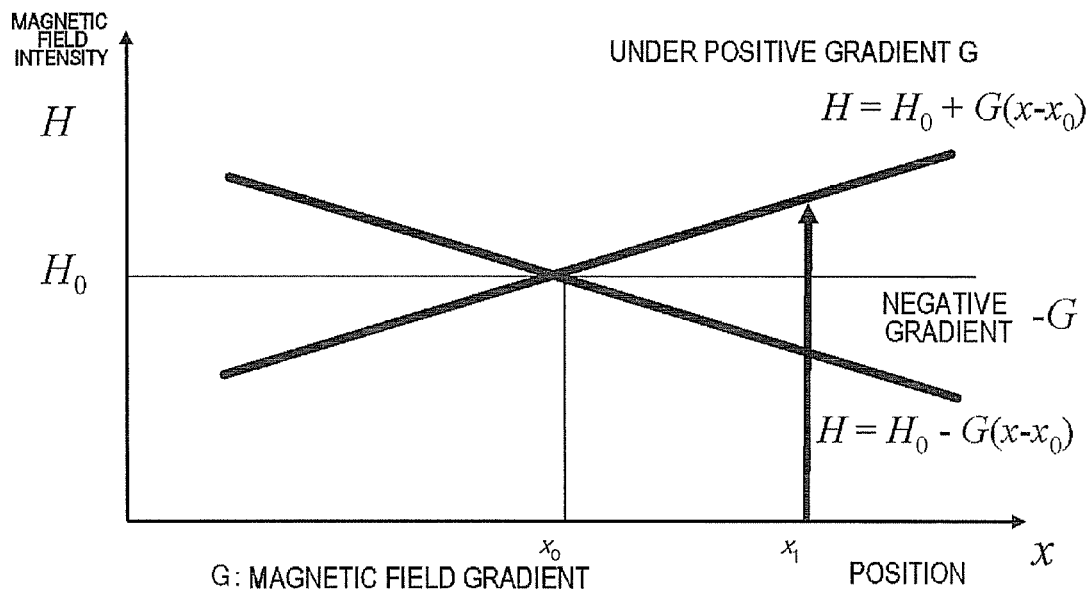
FIG. 4 is a drawing explaining distribution of a gradient magnetic field.

FIG. 4 is a drawing explaining the gradient magnetic field distribution in procedure (b1) in the above. Referring to a magnetic field distribution in the x-direction, FIG. 4 shows a gradient magnetic field distribution increasing in the x-direction at a "positive constant gradient G" expressed by the equation (1) in the above. In comparison, FIG. 4 also shows a gradient magnetic field distribution degreasing in the x-direction at a "negative constant gradient $-G$". The magnetic field H herein is given $$H=H_0-G(x-x_0)$$

Figure 5:
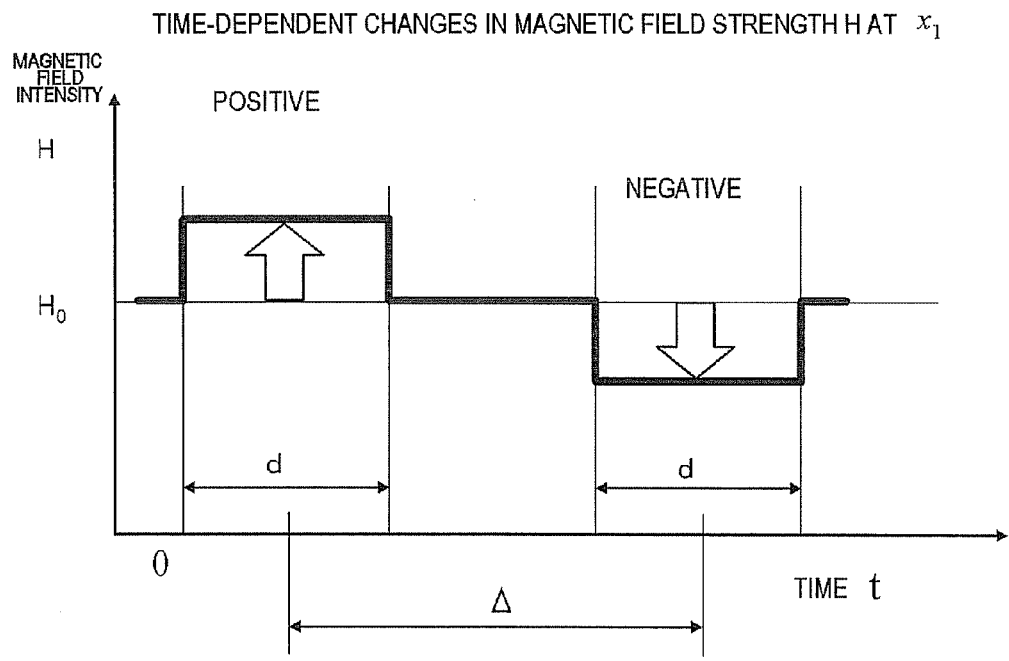
FIG. 5 is a drawing explaining a pair of positive/negative pulse gradient magnetic fields.

FIG. 5 is a drawing explaining a pair of positive/negative gradient magnetic field pulses produced by the procedure (a1) in the above. As shown in FIG. 5, the gradient magnetic field is kept for a certain duration of time d, and then changes from positive gradient $+G$ to negative gradient $-G$. FIG. 5 shows a mode of change of the magnetic field strength in a time-dependent manner, referring to a magnetic field strength at $x=x_1$. According to the PGSE method, the self-diffusion coefficient D can be calculated based on time d during which the gradient magnetic field G is kept, and time intervals (pulse intervals) $\Delta$ of the pair of positive/negative gradient magnetic fields.

Figure 6:
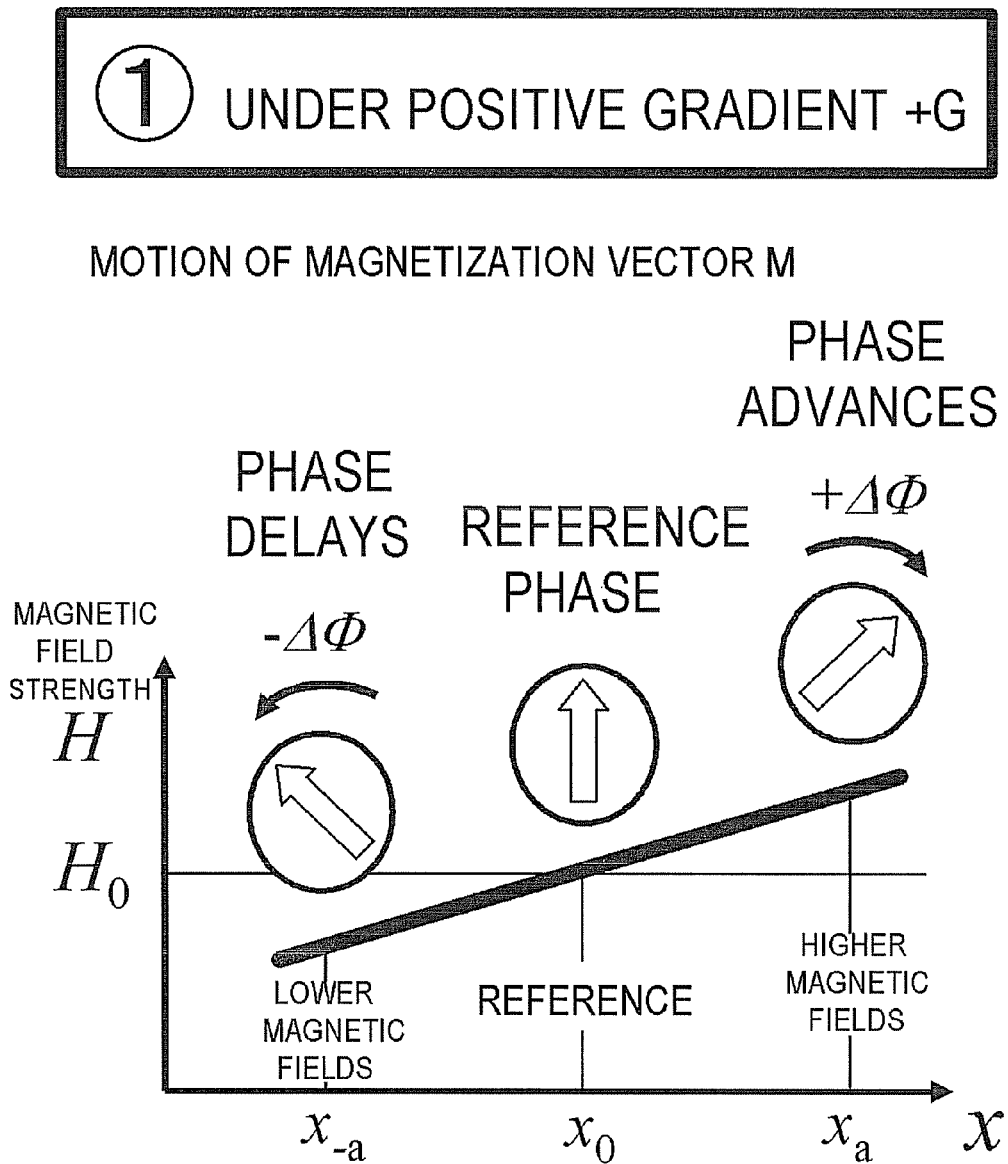
FIG. 6 is a drawing showing time-dependent changes in magnetization vector M.
Figure 7:
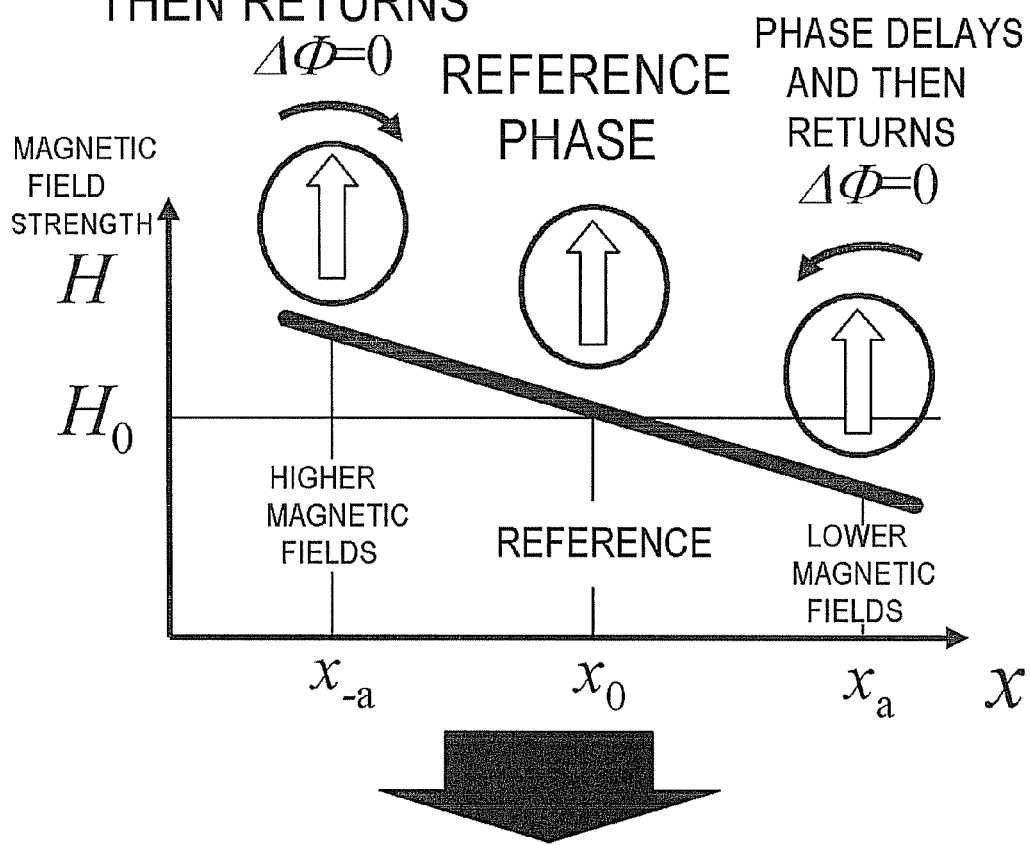
FIG. 7 is a drawing showing time-dependent changes in magnetization vector M.

Next, time-dependent changes in the "phase of magnetization vector M (also simply referred to as "magnetization M", hereinafter) applied with the PGSE method, when the position of magnetization M produced by a certain molecular group is fixed (immobilized), will be explained. FIG. 6 and FIG. 7 are drawings explaining the time-dependent changes of the magnetization vector M. FIG. 6 and FIG. 7 correspond to the cases where, in FIG. 5, the positive gradient $+G$ and the negative gradient $-G$ are respectively applied.

For the first case where, in FIG. 5, the positive gradient $+G$ is applied, rotation frequency $\omega$ of the magnetization M is determined in proportion to the magnetic field strength H at the individual positions x, as shown in FIG. 6. During a certain period of time d over which the gradient magnetic field is applied, the phase advances by dΦ (Δφ in the drawing) at positions in larger magnetic fields, whereas the phase delays by dΦ at positions in lower magnetic fields.

Still more specifically, the magnetization M applied with a magnetic field H higher than the static magnetic field $H_0$ makes the phase advanced by $d\Phi_+$. This is expressed by the equation below:

$$d\Phi_+ = \gamma \times (H - H_0) \times d [rad]$$
$$= \gamma \times G \times (x_a - x_0) \times d [rad]$$

If dΦ is positive, the phase advances.

On the other hand, when the negative gradient –G was applied in FIG. 5, the magnetization M is applied with a magnetic field H lower than the static magnetic field $H_0$, and the phase thereof delays by $d\Phi_-$. This is expressed by the equation below:

$$d\Phi_- = \gamma \times (H - H_0) \times d [rad]$$
$$= \gamma \times (-G) \times (x_{-a} - x_0) \times d [rad]$$

Because dΦ is negative, the phase delays.

When the negative gradient –G is applied in FIG. 5, as shown in FIG. 7, the magnetization M rotates at a rotation frequency ω in proportion with the magnetic field strength, wherein the gradient is in the direction opposite to the gradient +G, so that the phase starts to delay where it was previously advanced, and starts to advance where it was previously delayed.

Accordingly, the phase becomes all the same after the elapse of certain period of time d, giving absolutely same results with the case under the absence of the "pulse gradient magnetic field".

Figure 8:
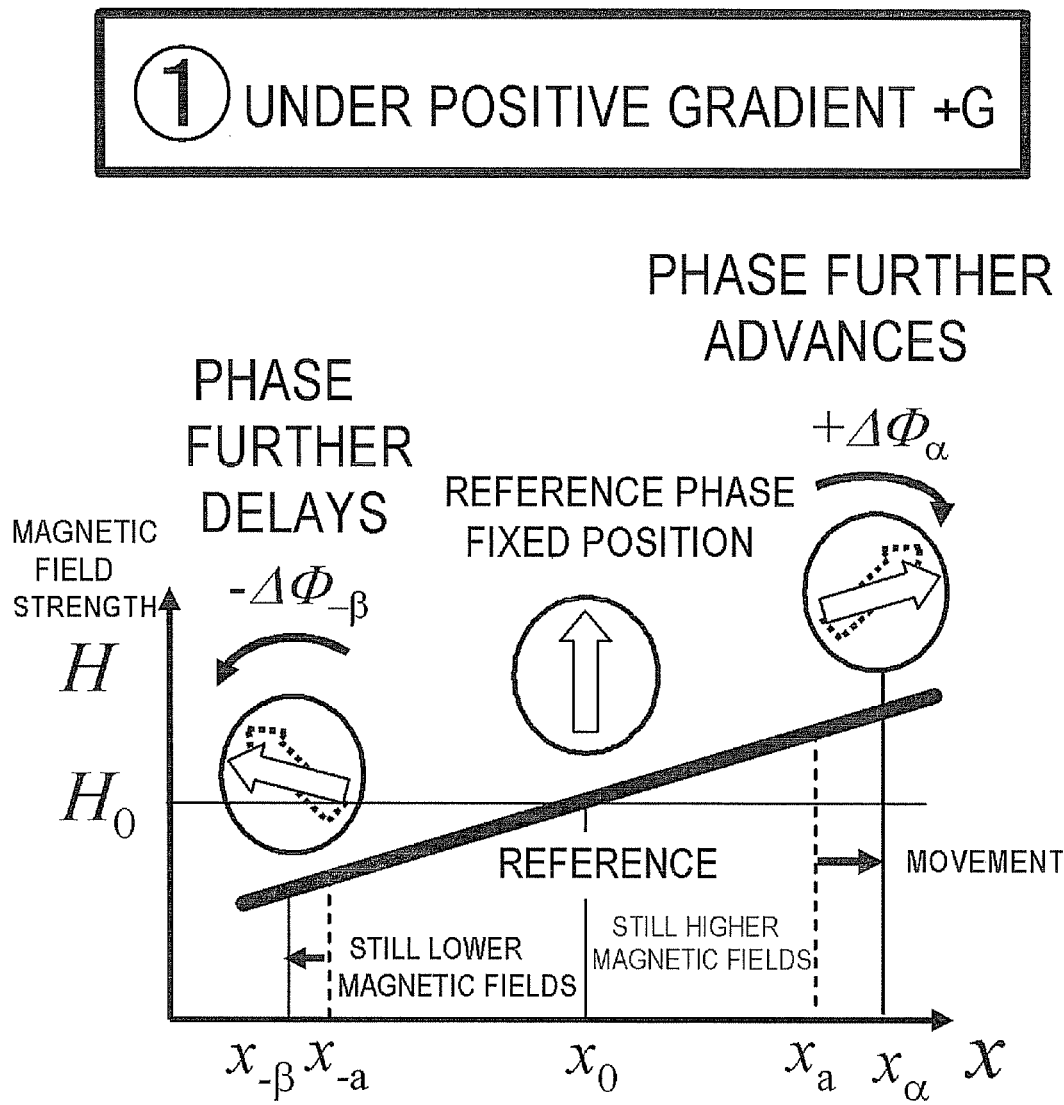
FIG. 8 is a drawing showing time-dependent changes in magnetization vector M.
Figure 9:
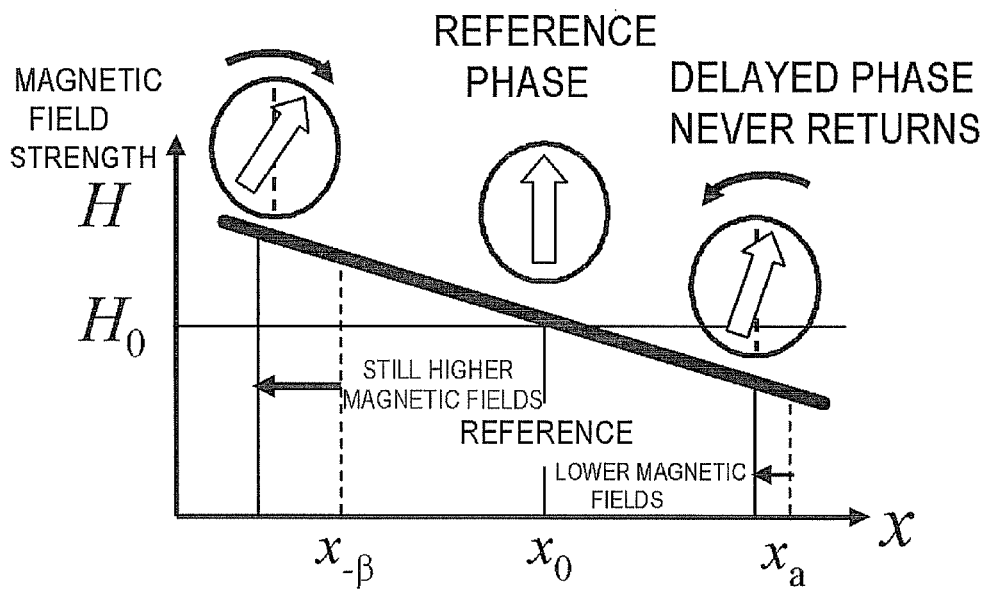
FIG. 9 is a drawing showing time-dependent changes in magnetization vector M.

Next paragraphs will describe the case where the protic solvent molecules in the sample are under thermal vibration just like normal molecules, ceaselessly causing random moving in their position. FIG. 8 and FIG. 9 are drawings showing time-dependent changes in the magnetization vector M. FIG. 8 and FIG. 9 correspond respectively to the cases where the positive gradient +G and the negative gradient –G were applied in FIG. 5.

Considering now the magnetization M produced by a group of randomly moving molecules. The magnetization M applied with a magnetic field H larger than the static magnetic field $H_0$ is advanced in the phase by $d\Phi_+$ (random). This is expressed by the equation below:

$$d\Phi_+ (random) = \gamma \times (H - H_0) \times d [rad]$$
$$= \gamma \times G \times \{x(t = 0 \text{ to } d) - x_0\} \times d [rad]$$

Because dΦ is positive, the phase advances. In this equation, t represents duration of time over which the gradient magnetic field is applied.

On the other hand, when the negative gradient –G is applied in FIG. 5, a magnetic field H smaller than the static magnetic field $H_0$ is applied, and the magnetization M causes a delay of $d\Phi_-$. This is expressed by the equation below:

$$d\Phi_- (random) = \gamma \times (H - H_0) \times d [rad]$$
$$= \gamma \times (-G) \times \{x(t = \Delta \text{ to } (\Delta + d)) - x_0\} \times d [rad]$$

Because dΦ is negative, the phase delays.

Because x (t=0 to d) and x (t=Δ to (Δ+d)) are not equal, also $d\Phi_+$ (random) and $d\Phi_-$ (random) do not become equal. For this reason, under random Brownian motion of the molecules due to thermal vibration, the phase of magnetization M in the PGSE method is not cancelled, so that intensity of the NMR signal as a synthetic vector thereof decreases.

Making use of such decrease in the NMR signal, the self-diffusion coefficient D of protons in the sample can be determined, by detecting the lowering in the NMR signal observed under the gradient magnetic field, as compared with the NMR signal observed without applying the gradient magnetic field.

Figure 10:
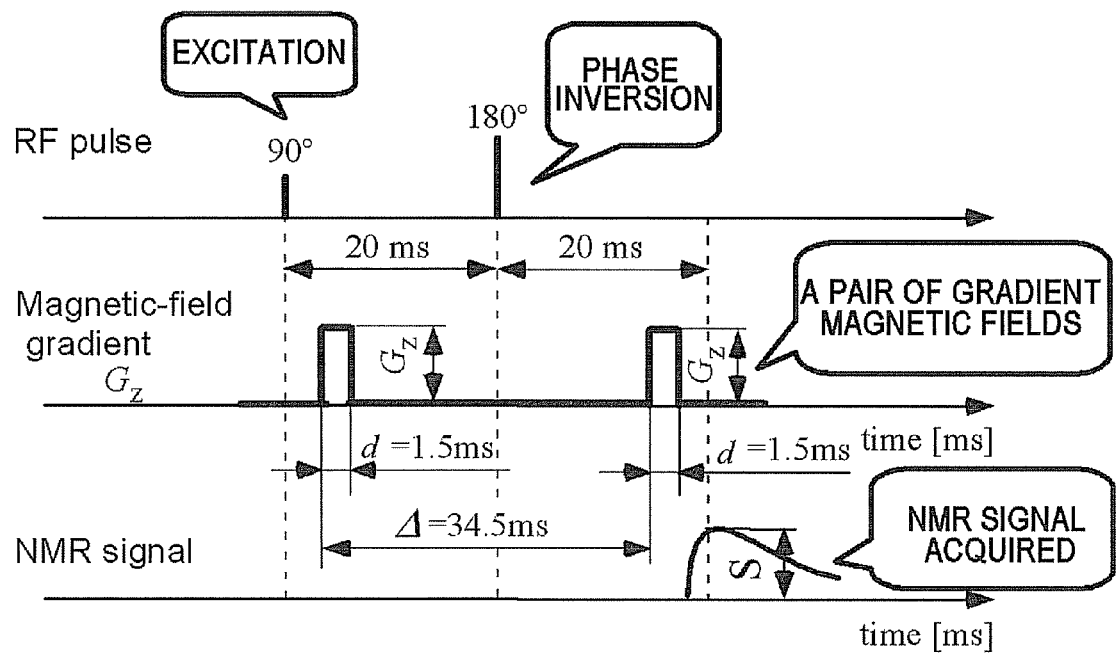
FIG. 10 is a drawing showing an exemplary pulse sequence in measurement of self-diffusion coefficient.

FIG. 10 is a drawing showing an exemplary pulsed-gradient, spin-echo sequence used for measuring the self-diffusion coefficient D. In the sequence shown in FIG. 10, in addition to the general spin-echo sequence, a pair of gradient magnetic field pulses Gz having the same application time and intensity are applied in the z direction, assuming a 180° pulse for excitation as the axis of symmetry, and thereby a spin-echo signal is typically obtained as the NMR signal. Peak intensity S of the NMR signal is depends on intensity Gz [gauss/m] of the pulse gradient magnetic field to be applied, application time d, and pulse interval Δ, and is correlated with the self-diffusion coefficient Dz [m²/s] by the relational expression below:

$$\ln(S/S_0) = -\gamma^2 D z \Delta^2 d G z^2 \quad (II)$$

In the equation (II), $S_0$ expresses intensity of the general NMR signal obtained under Gz=0. d, Δ and Gz represent pulse width of the gradient magnetic field pulse, time interval of a pair of gradient magnetic field pulses, and magnetic field gradient (z direction) of the gradient magnetic field pulses, respectively. γ represents gyromagnetic ratio, which is a nucleus-specific value. $S_0$ represents peak intensity of the NMR signal obtained under Gz=0, that is, under the absence of the gradient magnetic field, and γ represents a gyromagnetic ratio of 42.577×10² [1/gauss·s] of hydrogen nucleus¹H to be measured.

FIG. 10 exemplifies a sequence for the case of d=1.5 ms and Δ=34.5 ms. By applying the magnetic field to the sample typically according to such sequence, the self-diffusion coefficient Dz can be calculated in a stable manner, based on the peak intensity S of NMR signal.

Figure 11:
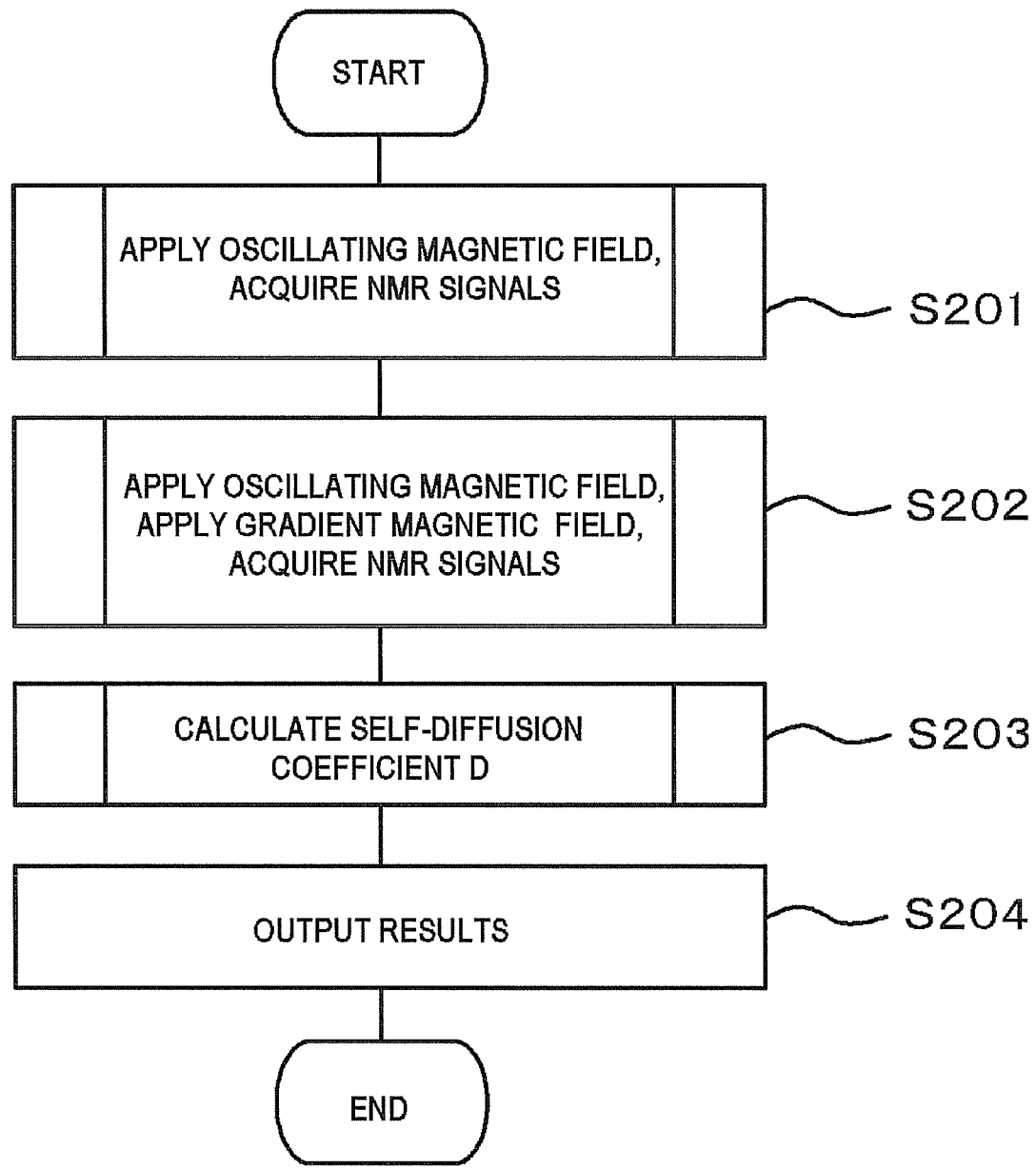
FIG. 11 is a flow chart showing an outline of the method of local measurement of mobility.

FIG. 11 is a flow chart shown as a conclusion of the above-described procedures of measurement. The flow shown in FIG. 11 allows local measurement of mobility at the specific position of the sample based on the PGSE method, and includes the steps below:

First, the sample is placed in the static magnetic field produced by typically using magnets, and the static magnetic field is applied to the sample. While keeping this state, the sample is applied with the oscillating magnetic field for excitation, and a corresponding NMR signal is acquired (S201). The gradient magnetic field is not applied. Step 201 further includes the following steps:

a first step applying the oscillating magnetic field for excitation to the sample according to a predetermined pulse sequence; and a second step acquiring a magnetic resonance signal corresponded to the pulse sequence in the first step.

Next, Step 202 is executed by applying the gradient magnetic field to the same region of the sample. In step 202, a third step and a fourth step described below are executed once, or plural number of times:

a third step applying an oscillating magnetic field for excitation and gradient magnetic field to said sample according to a predetermined pulse sequence; and a fourth step acquiring a magnetic resonance signal corresponded to the pulse sequence in the third step.

In the first step and the third step, a local magnetic field is applied to the specific position of the sample, using the small-sized RF coil smaller in size than the sample (S202). In the second step and the fourth step, the NMR signal is acquired from the specific position of the sample, using the small-sized RF coil smaller in size than the sample.

It is also allowable to apply, in the first step, the gradient magnetic field to the sample according to a predetermined pulse sequence, and to apply, in the third step, the gradient magnetic field differed in the energy from that in the first step, according to a predetermined pulse sequence.

Although an example without applying the gradient magnetic field in the first step was shown in FIG. 11, it is also allowable to apply, in the first step, a predetermined gradient magnetic field differed in the energy from that in the third step. In this case, the energy of the gradient magnetic field in the first step is preferably adjusted typically to a value close to zero. By adjusting the energy of gradient magnetic field at a value close to zero, (1) the gradient adjusted close to zero maximizes intensity of the NMR signal, raises a signal/noise ratio, and can thereby minimize influences of the noise; and (2) the gradient adjusted, however, not to zero can prevent the NMR signal from being attenuated due to interference with an NMR signal emitted from the region applied with an incomplete 180° pulse, when the small-sized surface coil has a non-uniform excitation region, and thereby in part of the region the 180° pulse may be given as pulses of smaller energy.

By virtue of these effects, more exact self-diffusion coefficient D can be measured.

Next, the self-diffusion coefficient D is calculated using a plurality of NMR signals obtained under stepwisely-varied pulse gradient magnetic fields (S203). In step 203, based on information of NMR signal obtained in the second step and information of NMR signal obtained in the fourth step, the self-diffusion coefficient D at the specific position of the sample is calculated.

It is also allowable, after the procedure of step 203, to calculate a parameter indicating other mobility of the protic solvent in the sample, based on the self-diffusion coefficient D calculated in step 203. Thereafter, the result is output (S204).

Details of the individual steps will be explained below.

(i) Step 201 and Step 202 (Application of Oscillating Magnetic Field for Excitation, Application of Gradient Magnetic Field, and Acquisition of NMR Signal)

In step 201 and step 202, oscillating magnetic field for excitation and the gradient magnetic field are applied to the sample, according to a predetermined sequence. More specifically, as described previously, the energy of the gradient magnetic field is adjusted to zero or to a value close to zero in step 201, and a predetermined gradient magnetic field is applied in step 202.

The oscillating magnetic field for excitation is a pulse sequence composed of a plurality of pulses, and the gradient magnetic field is a pair of pulse sequences corresponded to the oscillating magnetic field for excitation. The pulse sequence is preferably composed of (a2) to (d2) below:

(a2) a 90° pulse of the oscillating magnetic field for excitation;

(b2) a gradient magnetic field pulse starts after the elapse of pulse time of (a2), and applied for a certain duration of time d;

(c2) a 180° pulse of the oscillating magnetic field for excitation applied after the elapse of pulse time $\tau$ of (a2) ; and (d2) a gradient magnetic field pulse starts after the elapse of pulse time of (c2), and applied for a certain duration of time d.

The NMR signal corresponded to the pulse sequence is then measured. The peak intensity S of the NMR signal is measured by the spin-echo method as shown in FIG. 3.

As has been described referring to FIG. 8 and FIG. 9, in this embodiment, the self-diffusion coefficient D of protons in the sample is calculated by stepwisely applying the gradient magnetic fields, and by detecting the degree of lowering in the NMR signal corresponding to increase in the magnetic field gradient. However in the practical measurement, non-uniformity in the magnetic field may occur depending on characteristics of the sample and instrument, and thereby the self-diffusion coefficient D may be obtained only in an incorrect manner.

Therefore in this embodiment, the measurement errors ascribable to the non-uniformity in the magnetic field are effectively reduced, by applying the oscillating magnetic field for excitation by the spin-echo method, according to the pulse sequences (a2) and (c2) described in the above. This point will be explained below.

A hydrogen nucleus placed in a static magnetic field has a net magnetization vector in the direction along the static magnetic field (referred to as the z-direction for convenience sake), wherein the magnetization vector inclines in the positive direction of the Y-axis when an RF wave of a specific frequency (referred to as resonance frequency) is externally irradiated in the direction of the X-axis, normal to the Z-axis, the magnetization vector, and allows observation of a nuclear magnetic resonance signal (referred to as NMR signal), thereby a nuclear magnetic resonance signal (referred to as NMR signal) can be observed. In this process, a pulse for excitation applied in the direction of X-axis to consequently acquire the NMR signal of maximum intensity is called 90° pulse. After the magnetization vector is inclined by the 90° pulse to the positive direction of the Y-axis, a 180° pulse for excitation is externally applied time $\tau$ after "in the direction of the Y-axis", to thereby invert the magnetization vector "assuming the Y-axis as the axis of symmetry". As a consequence, the magnetization vector converges time $2\tau$ after, on the Y-axis on the "positive side" thereof, and thereby an echo signal having a large amplitude is observed. The self-diffusion coefficient D can be calculated by measuring the peak intensity S of this NMR signal, and by determining correlation with the gradient magnetic field described later.

Because the magnetization vector is inverted assuming "the Y-axis as the axis of symmetry" as described in the above, a compensation function similar to that obtained by the CPMG method, as shown in FIG. 2 can express. As a consequence, by adopting the pulse sequence composed of (a2) to (d2), measurement errors ascribable to the non-uniformity in the magnetic field can effectively be reduced.

(ii) Step 203 (Measurement of Self-Diffusion Coefficient D)

In step 203, the self-diffusion coefficient D is determined based on the peak intensity of the NMR signal. The self-diffusion coefficient D of proton is expressed by the equation (II) as described in the above, using the peak intensity S of the NMR signal obtained by the PGSE method. The self-diffusion coefficient D of protons in the sample can be determined, based on the peak intensity $S_0$ observed without applying the gradient magnetic field G and the peak intensity S of the NMR signal obtained under the presence of gradient magnetic field G. For example, by carrying out measuremeny at the same position of the sample while varying magntude of the gradient magnetic field G, and by plotting relations between $\ln(S/S_0)$ and $-\gamma^2 D\Delta^2 dG^2$, the self-diffusion coefficient D can be determined based on the slope of the plotting.

Figure 65:
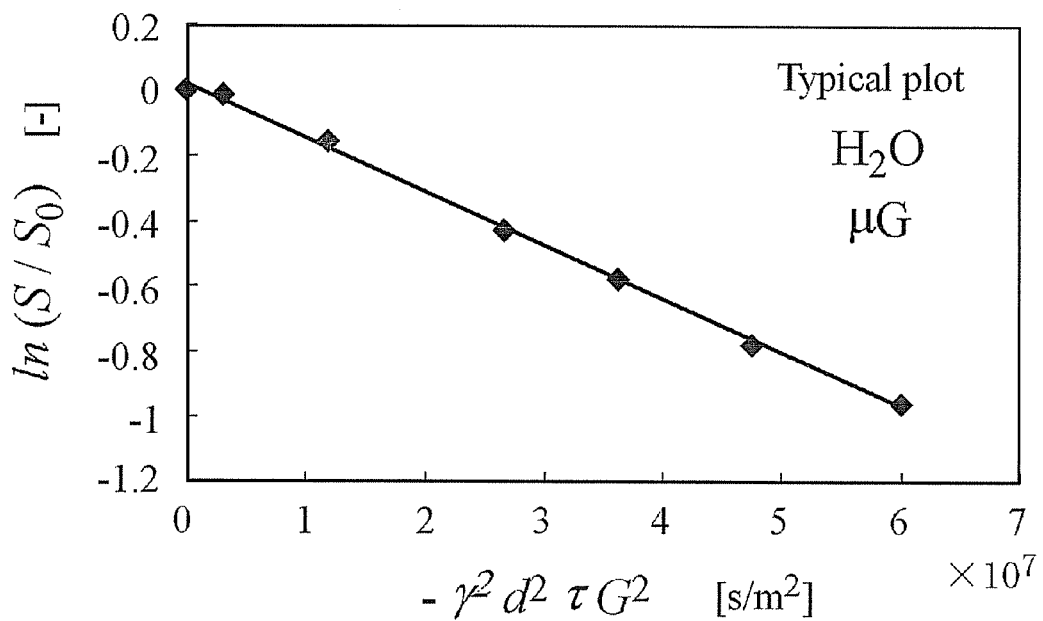
FIG. 65 is a drawing showing an exemplary measurement of self-diffusion coefficient.

FIG. 65 is a drawing showing an exemplary measurement of self-diffusion coefficient D. The amount of lowering in intensity of the NMR signal was obtained herein, by measuring the peak intensity of the NMR signal of distilled water, while varying energy of the gradient magnetic field. The measurement temperature was set to 25° C. The self-diffusion coefficient D can be determined based on the slope of a straight line expressed by $\ln(S/S_0)=-\gamma^2 D\Delta^2 dG^2$, which is the equation (II).

Methods of measuring local mobility based on the above-described principle, and exemplary instruments capable of realizing the methods will be explained below in the first embodiment to the fourth embodiment.

Also methods of measuring local water content and local mobility (self-diffusion coefficient is measured as the mobility in this embodiment) based on the above-described principle, methods of measuring the amount of movement based on the water content and the mobility of water molecules, and exemplary instruments realizing these methods will be explained in the fifth embodiment to the tenth embodiment.

First Embodiment

Figure 12:
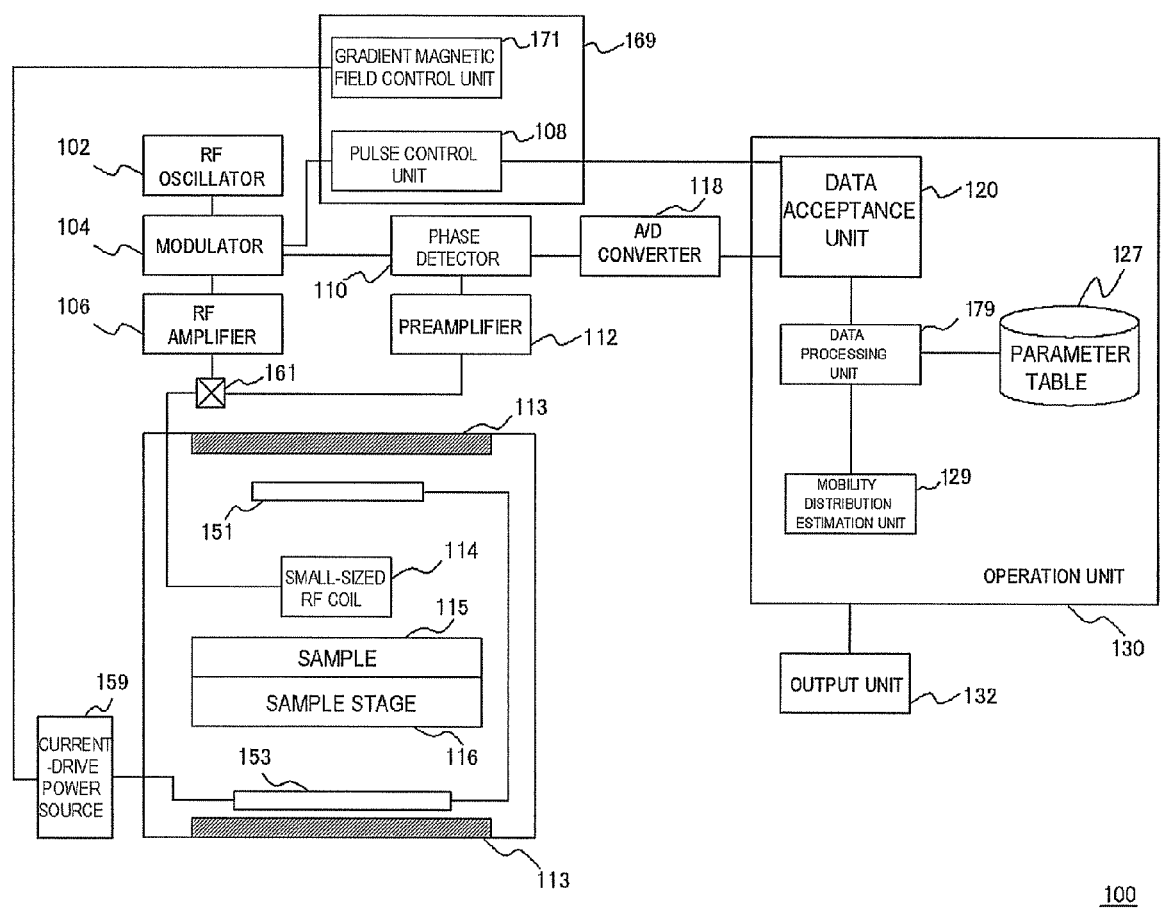
FIG. 12 is a block diagram showing a configuration of a measuring instrument according to a first embodiment of the present invention.
Figure 13:
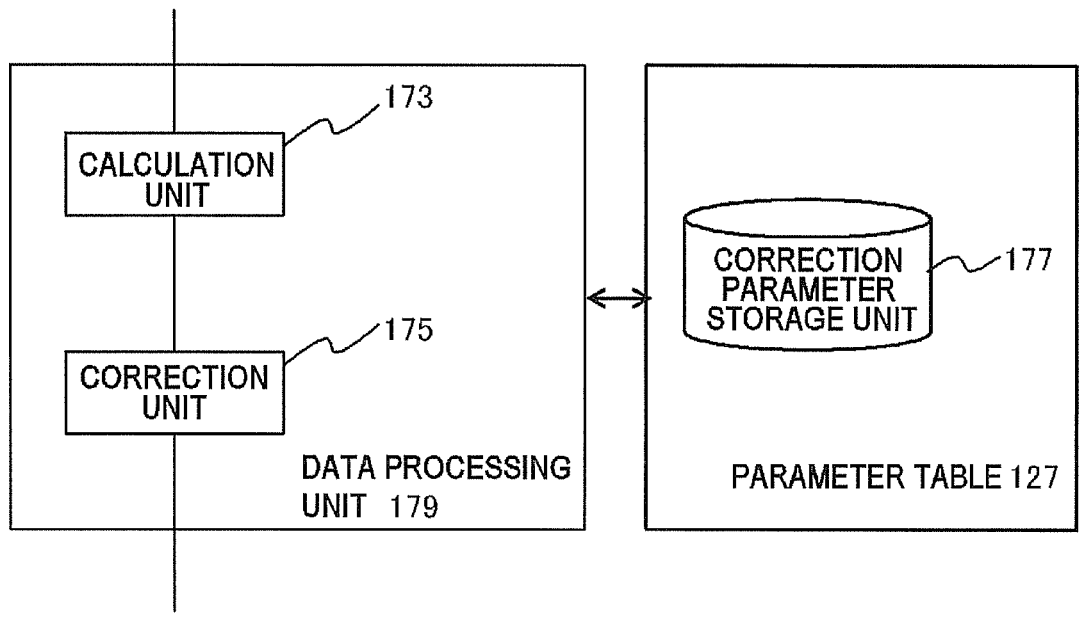
FIG. 13 is a drawing showing a schematic configuration of a data processing unit of the mobility measuring instrument according to this embodiment.

FIG. 12 is a drawing showing a schematic configuration of a mobility measuring instrument 100 according to this embodiment. FIG. 13 is a drawing showing further details of a data processing unit 179 and a parameter table 127 of the instrument shown in FIG. 12.

The instrument is aimed at locally measuring mobility of a protic solvent in a sample (sample 115) based on the gradient magnetic field NMR method, and includes:

a sample stage 116 on which the sample 115 is placed;

a static magnetic field application unit (magnet 113) applying a static magnetic field to the sample 115;

gradient magnetic field application units (G coil 151, G coil 153) applying a gradient magnetic field to the sample 115;

a small-sized RF coil 114 smaller in size than the sample 115, applying an oscillating magnetic field for excitation to the sample 115, and acquiring a magnetic resonance signal corresponded to the oscillating magnetic field for excitation and the gradient magnetic field;

a control unit (pulse control unit 108) applying the gradient magnetic field and the oscillating magnetic field for excitation according to a predetermined pulse sequence; and an operation unit 130 calculating mobility at a specific position of the G coil 151, based on the NMR signal acquired corresponding to different gradient magnetic fields.

The G coil 151 and the G coil 153 are gradient magnetic field coils disposed apart from the small-sized RF coil 114. Both of the G coil 151 and the G coil 153 are planar coils, and are disposed vertically while placing the small-sized RF coil 114 in between.

The mobility measuring instrument 100 has a storage unit (parameter table 127) storing, for every species of the sample 115, information expressing correlation between the mobility of protic solvent in the sample 115 and the self-diffusion coefficient. The operation unit 130 is configured so as to acquire information corresponded to the sample to be measured from the parameter table 127, and to calculate the mobility based on the information.

FIG. 13 is a drawing showing a detailed structure of the data processing unit 179 of the operation unit 130. The data processing unit 179 is composed of a calculation unit 173 and a correction unit 175. The calculation unit 173 obtains a calculated value of mobility based on intensity of the NMR signals acquired corresponding to different gradient magnetic fields. The correction unit 175 acquires calculated value of mobility acquired by the calculation unit 173, and corrects, as occasion demands, the calculated value adapted to the size of the small-sized RF coil 114. A method of correction will be described later.

The small-sized RF coil 114 applies the oscillating magnetic field for excitation, using a pulse sequence composed of a (a) 90° pulse, and a (b) 180° pulse applied time τ after the pulse of (a). The pulse sequence may further contain a 180° pulse applied time τ earlier than the 90° pulse. The sequence may be configured also as having the (a) 90° pulse in a first phase, and the (b) 180° pulse in a second phase 90° shifted from the first phase.

The sample stage 116 is a stage on which the sample 115 is placed, and may be of a predetermined geometry and material.

The sample 115 is configured as having a protic solvent held in the target sample to be measured. The sample composing the sample 115 may have various forms such as film, solid such as bulk substances, liquid, and gels typically composed of jelly-like substances such as agar gel. When the film-like substance is used, results of measurement of local mobility of protic solvent can be obtained in a stable manner. In particular, when a film characteristically holding water therein is used as the sample, the results of measurement may be obtained in a more stable manner.

The magnet 113 applies the static magnetic field over the entire portion of the sample 115. While being applied with the static magnetic field, the sample is further applied with the oscillating magnetic field for excitation and the gradient magnetic field pulse, and thereby the self-diffusion coefficient D is measured.

The small-sized RF coil 114 applies the oscillating magnetic field for excitation to a specific position of the sample 115, and acquires an NMR signal corresponded to the oscillating magnetic field for excitation. The NMR signal is specifically an RF pulse allowing the oscillating magnetic field for excitation to induce nuclear magnetic resonance.

The small-sized RF coil 114 is preferably not larger than a half size of the entire sample, and more preferably not larger than 1/10. By such adjustment in size, the local mobility of protic solvent in the sample may exactly be measured within a short time. The size of the sample herein may be defined by a projected area of the sample being placed, wherein adjustment of the occupational area of the small-sized RF coil 114 preferably to not larger than 1/2, and more preferably to not larger than 1/10, of the projected area allows exact measurement within a short time. The size of the small-sized RF coil 114 is preferably adjusted, for example, to not larger than 10 mm in diameter.

The small-sized RF coil 114 used herein may preferably be such as that previously shown in FIG. 14. By using the planar coil as shown in the drawing, the measurement area may be limited.

For the case where a small-sized surface coil is used as the small-sized RF coil 114, ratio of the inner diameter and the outer diameter of the small-sized RF coil 114 (inner diameter/ outer diameter) is preferably close to 1, and more specifically 0.5 or larger and 1 or smaller, and in particular 0.65 or larger and 1 or smaller.

The inner diameter/outer diameter of 1 herein means that the small-sized RF coil is a single-turn coil, assuming the diameter of the wire of the small-sized RF coil as zero.

By adjusting the ratio of the outer diameter and the inner diameter of the small-sized RF coil to 0.5 or larger, the range measurable by the small-sized RF coil can be adjusted to a range conformable to the visible outline of the small-sized RF coil.

Figure 66:
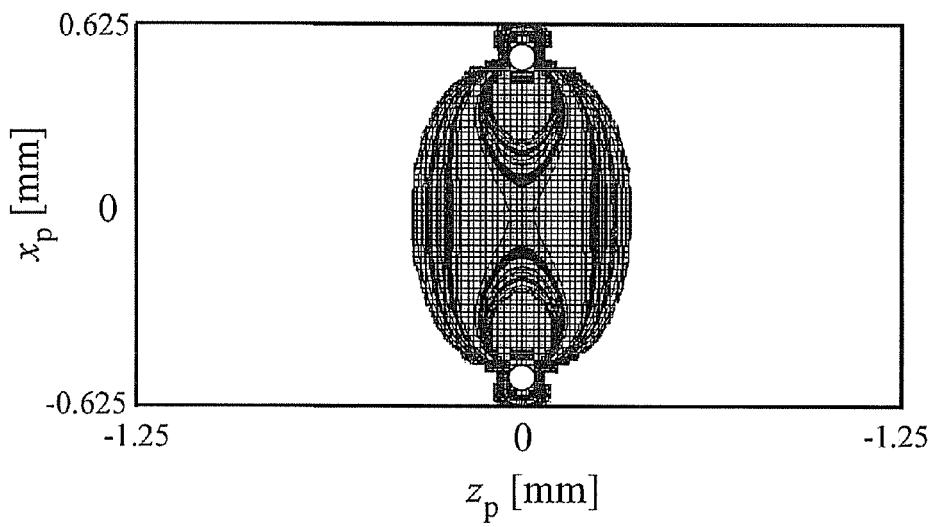
FIG. 66 is a drawing showing a distribution of intensity of received echo signals when a single-turn, small-sized RF coil (outer diameter=1 mm, inner diameter=1 mm, inner diameter/outer diameter=1) was used.

FIG. 66 shows an intensity distribution of received echo signals obtained by using a single-turn small-sized RF coil (outer diameter=1 mm, inner diameter=1 mm, inner diameter/outer diameter=1), on the center axis of the small-sized RF coil. In FIG. 66, open circles indicate positions of the coil.

Figure 67:
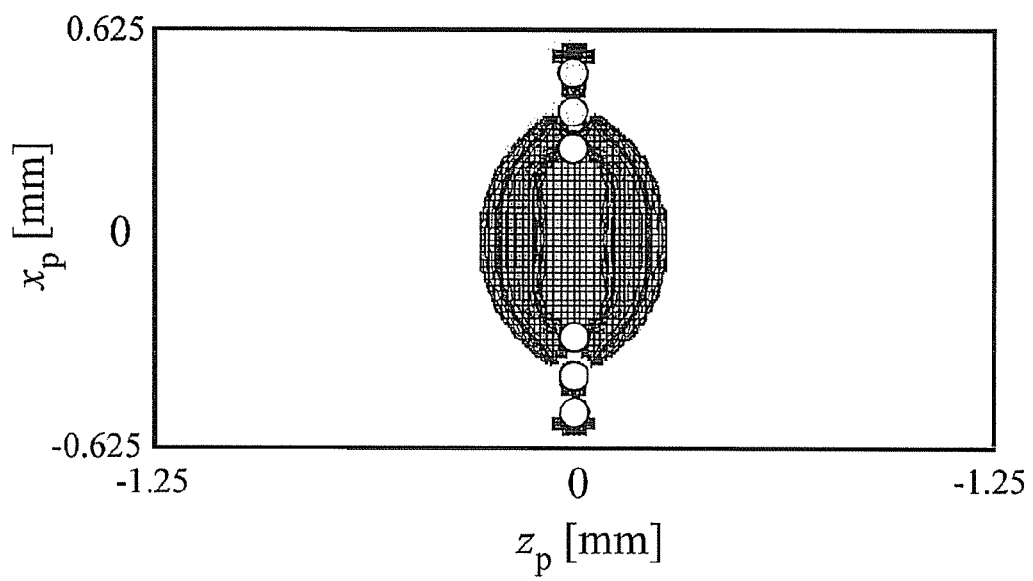
FIG. 67 is a drawing showing a distribution of intensity of received echo signals when a 3-turn, small-sized RF coil (outer diameter=1 mm, inner diameter=0.5 mm, inner diameter/outer diameter=0.5) was used.

FIG. 67 shows an intensity distribution of received echo signals obtained by using a 3-turn, small-sized RF coil (outer diameter=1 mm, inner diameter=0.5 mm, inner diameter/outer diameter=0.5), on the center axis of the small-sized RF coil. In FIG. 67, open circles indicate positions of the coil.

In FIG. 66 and FIG. 67, the direction of the z-axis means the thickness-wise direction of the sample, and the direction of the x-axis lies along the surface of the sample.

It is known from FIG. 66 and FIG. 67 that the range measurable by the single-turn small-sized RF coil having a ratio of inner diameter/outer diameter of 1 falls in the range conformable to the visible outline of the small-sized RF coil. In contrast, the range measurable by the 3-turn, small-sized RF coil having a ratio of inner diameter/outer diameter of 0.5 is narrower than the measurable range expected from the visible outline of the small-sized RF coil.

The distributions of received echo signals shown in FIG. 66 and FIG. 67 were calculated based on assumptions below:
  diameter of wire of the coil is assumed as zero (infinitesimal wire diameter);
  skin effect during electric conduction is assumed as zero (the diameter of wire assumed as zero means that also an effect of current flow along the surface is negligible);
  the 3-turn coil is configured by disposing three rings of different diameters in a concentric manner (not in spiral);
  the coil is composed of a lead wire only, ignoring the sheath (dielectric constant and permittivity adopted herein are those of the vacuum); and
  the lead portion (wiring portions other than the coil) is ignored.

When the number of turns of the small-sized RF coil is reduced so as to make the inner diameter/outer diameter closer to 1, the measurable range may be conformable to the visible outline of the small-sized RF coil, whereas sensitivity in detection of NMR signal may be lowered.

On the other hand, when a thick lead wire is used, and the number of turns of the small-sized RF is increased, the sensitivity in detection of NMR signal may be increased, whereas the measurable range may be less conformable to the visible outline of the small-sized RF coil, because the inner diameter/outer diameter is reduced. Reduction in the measurable area may also lower the NMR signal intensity, and may degrade the signal/noise ratio.

it is therefore preferable to use a thin-as-possible wire, while keeping the electric conductivity at a high level, and to increase the number of turn so as to make the inner diameter/outer diameter closer to 1.

Advantages and disadvantages of manufacturing the small-sized RF coil using thick lead wire, and advantages and disadvantages of manufacturing the small-sized RF coil using thin lead wire will be described below:

(a) Advantages and Disadvantages of Manufacturing the Small-Sized RF Coil Using Thick Lead Wire
  Electric conductivity of the lead wire increases, and the signal/noise ratio improves;
  Easy manufacturing. As the lead wire becomes thicker, the product will be less likely to be unacceptable, because the lead wire per se is kept conductive even when micro-pits or irregularity in the contour should occur in the process of manufacturing thereof by plating or etching; and
  As the lead wire becomes thicker, the small-sized coil having a larger number of turns is increased in the diameter, or decreased in the inner diameter. The number of turns will be limited if the diameter is fixed.

(b) Advantages and Disadvantages of Manufacturing the Small-Sized RF Coil Using Thin Lead Wire
  Electric conductivity of the lead wire decreases, and the signal/noise ratio degrades;
  Difficult manufacturing. As the lead wire becomes thinner, the product is more likely to cause disconnection even by micro-pits possibly produced in the process of manufacturing thereof by plating or etching. Only a slight irregularity on the contour of the lead wire may result in fusion between the adjacent lead wire, spoiling the role as a coil. Ratio of unacceptable products may increase; and
  As the lead wire becomes thinner, the diameter of the small-sized coil may be kept small even with a large number of turns. Also the ratio of the inner diameter and the outer diameter thereof may be adjusted closer to 1. The number of turns may be increased even under a fixed diameter.

As the small-sized RF coil 114, not only planar spiral coils, but also those having various shapes may be adoptable. For example, the planar figure-8 coil, for example, is adoptable. The figure-8 coil contains two spiral coils of right-handed and left-handed ones, wherein by using either one of the spiral coils, both magnetic fields, one directed to the principal magnetic field of the magnet, and the other directed to the opposite direction, can be detected. The spiral coil has a sensitivity in the direction of axis of the wound coil, whereas the figure-8 coil has a sensitivity in the same plane with the wound coil.

Only a single, or two or more small-sized RF coils 114 may be used. Use of a plurality of coils allows measurement of distribution of mobility of protic solvent in the sample 115. In this case, two-dimensional distribution of mobility over the surface of sample can be determined by two-dimensional arrangement of the coils along the surface of the sample. Three-dimensional distribution of mobility in the sample can be determined by three-dimensional arrangement of the coils in the sample 115.

The oscillating magnetic field for excitation applied by the small-sized RF coil 114 configured as a planar spiral coil is necessarily normal to the static magnetic field applied by the magnet 113.

Referring now back to FIG. 12, the oscillating magnetic field (oscillating magnetic field for excitation) applied by the small-sized RF coil 114 is generated by cooperation of an RF oscillator 102, a modulator 104, an RF amplifier 106, the pulse control unit 108, a switching unit 161 and the small-sized RF coil 114. More specifically, the oscillating magnetic field for excitation oscillated by the RF oscillator 102 is modulated by the modulator 104 based on control by the pulse control unit 108, and given in a pulse form. Thus-produced RF pulses are amplified by the RF amplifier 106, and sent to the small-sized RF coil 114. The small-sized RF coil 114 applies the RF pulses to the specific position of the sample placed on the sample stage 116. The NMR signals of the applied RF pulses are detected by the small-sized RF coil 114. The NMR signals are amplified by the preamplifier 112, and then sent to the phase detector 110. The phase detector 110 detects the NMR signals, and sends them to the A/D converter 118. The A/D converter 118 subjects the NMR signals to A/D conversion, and sends them to the operation unit 130.

Figure 15:
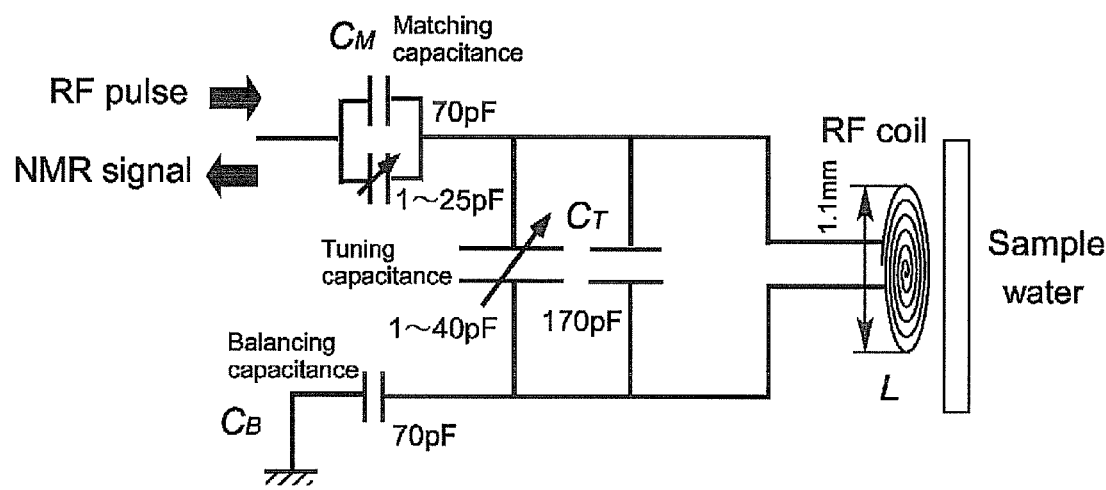
FIG. 15 is a drawing showing an exemplary LC circuit, applying the oscillating magnetic field for excitation and detecting the NMR signal, of the mobility measuring instrument according to this embodiment.

Application of the oscillating magnetic field for excitation and detection of NMR signals have been described, wherein these operations may be realized using an LC circuit containing the small-sized coil. FIG. 15 is a drawing showing an example of this sort of LC circuit. A coil unit (inductance unit) of the oscillation circuit is configured by a 1.1-mm-diameter, small-sized RF coil. In the nuclear magnetic resonance (NMR) method, atomic density and the spin relaxation time constant can be measured, by detecting motion of nuclear magnetization as an NMR signal as a result of spin resonance phenomenon of atomic nuclei placed in a magnetic field. In a 1-Tesla magnetic field, the spin resonance frequency is approximately 43 MHz, wherein the LC oscillation circuit such as shown in FIG. 15 is used for selectively detecting the frequency band with high sensitivity.

The oscillating magnetic field for excitation applied by the small-sized RF coil 114 to the sample 115 may typically be a pulse sequence composed of:

(a) a 90° pulse; and (b) a 180° pulse applied time $\tau$ after the pulse of (a).

Correlation between peak intensity of the NMR signals based on the spin-spin and the self-diffusion coefficient D of protic solvent in the sample may be obtained, also by using a pulse sequence having the 90° pulse in a first phase, and the 180° pulse in a second phase 90° shifted from the first phase.

Use of the small-sized RF coil 114 may raise difficulty in adjusting intensity of the excitation pulses of (a) and (b) in the above. For example in the target region to be measured, that is, in the region surrounded by the small-sized RF coil 114, the central portion and the peripheral portion thereof may cause difference in the degree of excitation, thereby making it difficult to excite the entire portion with a uniform angle of excitation, that is, with a constant ratio of intensity of the magnetic field excited based on (a) and (b). Variation in the ratio of angle of excitation based on (a) and (b) disables acquisition of appropriate spin-echo signals, and makes the measurement of mobility difficult.

Therefore in this case, the pulse control unit 108 is configured to execute another sequence having, in addition to the above-described pulse sequence, a step of applying a 180° pulse time $\tau$ earlier than the 90° pulse (a). By comparing behaviors of attenuation curves of the 180° pulse (b) corresponded to two these sequences, whether the excitation pulse intensities of the 90° pulse (a) and the 180° pulse (b) are exact or not may be discriminated. As a consequence, even if the excitation pulse density should shift due to abnormality in the instrument and the like, the abnormality can be detected before the measurement, making the measured values more exact.

The switching unit 161 is provided at a branching portion where the small-sized RF coil 114, the RF signal generating unit and the NMR signal detecting unit are connected.

The RF signal generating unit is composed of the RF oscillator 102, the modulator 104 and the RF amplifier 106, and generates RF signals allowing the small-sized RF coil 114 to generate the oscillating magnetic field for excitation. The NMR signal detecting unit is composed of the preamplifier 112, the phase detector 110 and the A/D converter 118, and detects the NMR signals acquired by the small-sized RF coil 114, and sends the NMR signals to the operation unit 130.

The switching unit 161 has a function of allowing switching between:

a first state having the small-sized RF coil 114 and the RF signal generating unit (RF amplifier 106) connected with each other; and a second state having the small-sized RF coil 114 and the NMR signal detecting unit (phase detector 110) connected with each other.

The switching unit 161 plays a role of a send/receive change-over switch. This role is aimed at disconnecting the preamplifier 112 in the receiving system, when the pulse for excitation amplified by an RF power amplifier is transmitted to the small-sized RF coil 114, so as to protect it from a large voltage, and also at interrupting noise leaked from the RF amplifier 106, which is emitted by its large transistors for amplification, when the NMR signals are received after excitation, to thereby prevent the noise from being transmitted to the preamplifier 112 in the receiving system. Because the measurement using the small-sized RF coil 114 handles very weak signals, the switching unit 161 is necessary for the reasons described below. On the other hand, for large-scale measuring systems using no small-sized RF coil 114, "crossed-diodes" will be sufficient for coping with the problem. The crossed-diodes is a diode turns ON upon being applied with a voltage of a predetermined level or above, and turns OFF when the voltage is smaller than the predetermined level.

Reasons why the "send/receive change-over switch", or the switching unit 161, is necessary particularly when the small-sized RF coil 114 is used, are as follow:

(i) The sample volume detectable by the small-sized coil of this measuring system is smaller than that detectably by large coils. The detectable sample volume is approximately as large as (inner surface area of coil×depth of radius of coil). For the purpose of measuring such very weak NMR signals, which attenuate proportionally to the volume, with low noise and high sensitivity, it is necessary to interrupt the noise leaked from the RF amplifier 106 in the sending system, which is emitted by its large transistors for amplification. On the other hand in the receiving system, it is necessary to use high-sensitivity preamplifier 112. When the high-sensitivity preamplifier 112 is used, it is necessary to disconnect the preamplifier 112, so as to protect it from high-voltage pulses for excitation supplied to the small-sized coil in the sending process.

(ii) When the nuclear magnetization in the sample volume is excited, the nuclear magnetization must be excited with an appropriate power of excitation pulses, more specifically while keeping intensities of the 90° pulse and the 180° pulse at 1:2. If an appropriate adjustment of the excitation pulse power results in failure, the pulse series targeted at in the spin-echo method cannot be obtained, an appropriate spin-echo signals cannot be acquired as a consequence, and thereby reliability of the measurement of mobility may degrade. This sort of non-conformity appears more distinctive, when the small-sized coil is changed over between sending and receiving, using the conventional crossed-diodes. Loss at the crossed-diodes may be negligible for the case of using large coils handling very large excitation pulse intensity, but the loss at the crossed-diodes cannot be negligible for the case where the small-sized coil is used, because the excitation pulse intensity handled by the small-sized coil is smaller than that handled by the large coils. For this reason, in view of ensuring an appropriate excitation pulse intensity, the "send/receive change-over switch" causing minimum loss is necessary.

By providing the switching unit 161 to the branching portion, loss of the oscillating magnetic field for excitation signal applied by the small-sized RF coil 114 to the sample 115 may be reduced, and as a consequence, the angle of pulses of the 90° pulse and the 180° pulse may exactly be controlled. Exact control of the angle of pulses is an important technical issue in the spin-echo method, in view of exactly achieving the compensation effect. In this embodiment, this issue is solved by providing the switching unit 161.

Because the RF detection coil used for local measurement has been becoming smaller, noise reduction in the NMR receiving is understood as an important factor for ensuring reliability of the measurement. Noises possibly contaminating the preamplifier 112 in the process of receiving of the NMR signals are mainly ascribable to the sending system of the RF wave, including "leakage of RF wave" from the RF amplifier 106 amplifying the excitation pulses, and "noises emitted by large-power amplifiers". When the NMR signals are received, it is necessary to exactly interrupt the excitation wave leaked from the transmission side by the switching unit 161, so as to allow receiving of the NMR signals with low noises. In the present invention, also this issue is solved by providing the switching unit 161.

Figure 16:
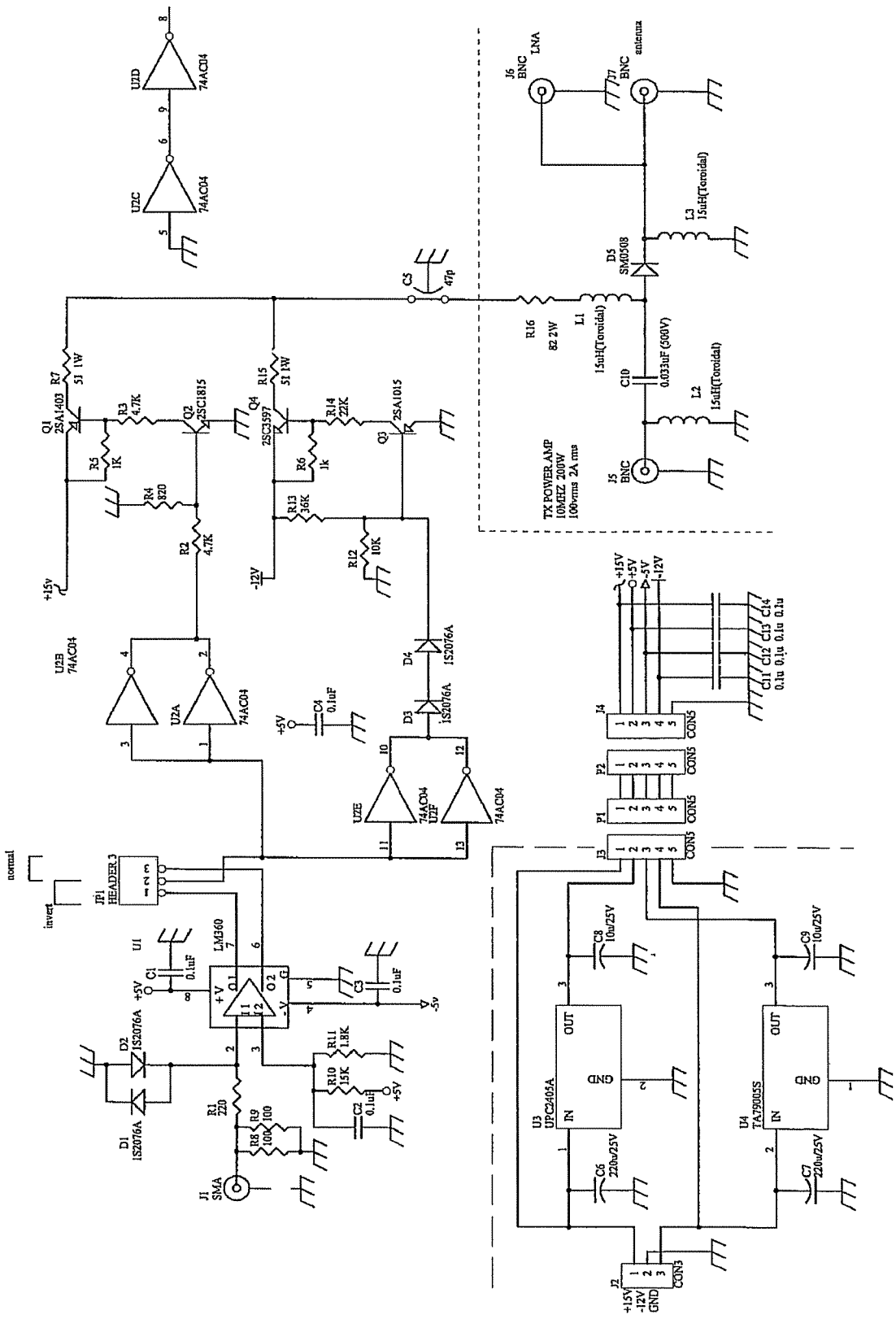
FIG. 16 is a drawing showing a configuration of a switching unit of the mobility measuring instrument according to this embodiment.

The switching unit 161 may adopt various configurations. FIG. 16 is a circuit diagram showing an exemplary configuration of the switching unit 161.

The switching unit 161 may adopt PIN diodes.

The G coil 151 and the G coil 153 are disposed so that they can apply the gradient magnetic field to the sample 115. The G coil 151 and the G coil 153 may adopt those having various geometries, wherein planar coils are adopted in this embodiment. The G coil 151 and the coil 153 are disposed above and below the plane containing the small-sized RF coil 114, while placing the small-sized RF coil 114 in between. In this example, the sample 115 has a plate-like geometry, and the individual G coils are disposed one by one on the individual surface sides of the sample 115, as being parallel with the surfaces of the sample 115.

Figure 17:
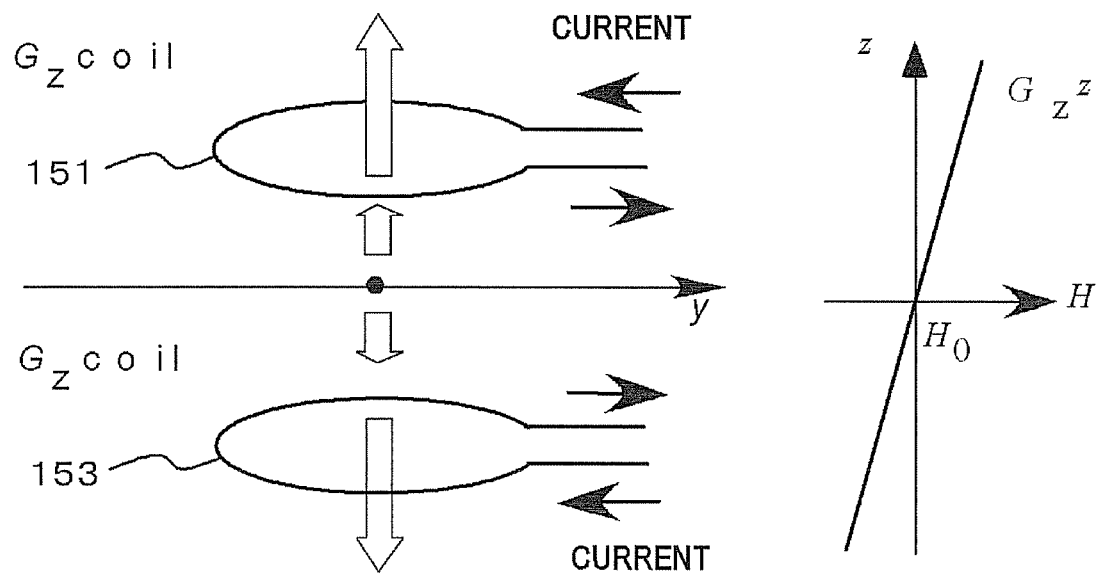
FIG. 17 is a drawing explaining arrangement of a G coil 151 and a G coil 153 in the mobility measuring instrument according to this embodiment.

FIG. 17 is a drawing showing an arrangement of the G coil 151 and the G coil 153. In FIG. 17, the sample 115 is disposed in parallel with the x-y plane. The individual G coils are planar coils, and are disposed in parallel with each other while placing the x-y plane in between, so as to apply the gradient magnetic field Gz inclined in the z-direction.

Application of the RF pulses from the RF oscillator 102 via the modulator 104 to the small-sized RF coil 114, and supply of pulse current via a current-supply power source 159 to the G coil 151 and the G coil 153 are controlled by the a control unit 169.

Figure 18:
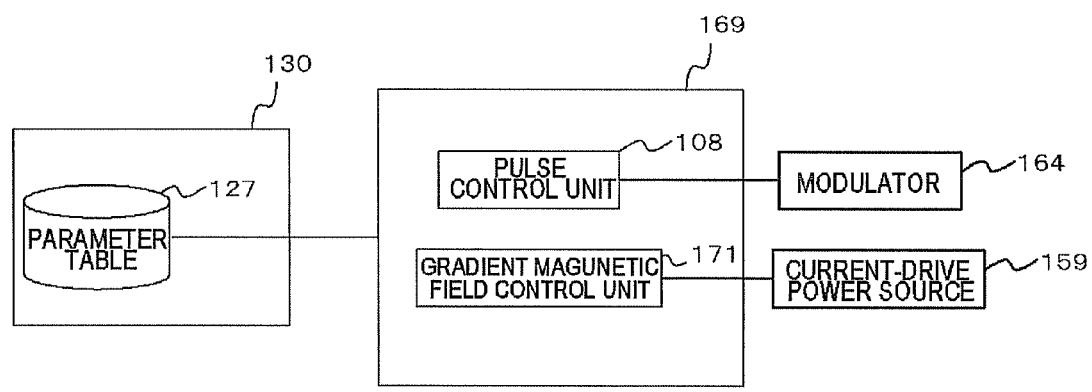
FIG. 18 is a drawing showing a configuration of the peripherals of the control unit of the instrument shown in FIG. 12.

FIG. 18 is a drawing showing an exemplary configuration of the control unit. The control unit 169 is composed of a pulse control unit 108 controlling operations of the RF amplifier 106, and a gradient magnetic field control unit 171 controlling operations of the current-drive power source 159. The parameter table 127 stores sequence data determining sequences of the RF pulses causing nuclear magnetic resonance, and of the pulse current causing the gradient magnetic field. The control unit 169 acquires the sequence data from the parameter table 127, and based on which supplies the pulse current to a predetermined coil.

Instrumental configuration around the sample have been explained in the above. Next paragraphs will explain process blocks of the NMR signals.

As shown in FIG. 12, the operation unit 130 has a data processing unit 179. The data processing unit 179 calculates the self-diffusion coefficient D using the equation (II) in the above, based on intensity of the NMR signals, and based on thus-calculated, self-diffusion coefficient D, the mobility of protic solvent at a specific position of the sample is calculated.

Inside the operation unit 130, first, the NMR signals are acquired by the data acceptance unit 120, and then the self-diffusion coefficient D is calculated by the data processing unit 179. The method of calculating the self-diffusion coefficient D will be described later.

The mobility of protic solvent calculated by the data processing unit 179, which is the self-diffusion coefficient D in this embodiment, is presented by the output unit 132 to the user. Various embodiments including presentation on a display device, output to a printer, and output to a file, are allowable as the mode of presentation, without special limitations.

In this embodiment, a plurality of small-sized RF coils 114 may be disposed in the sample, on the surface of the sample, or in the vicinity of the sample. This configuration allows application of the oscillating magnetic field for excitation and acquisition of the correspondent NMR signals, with respect to a plurality of positions of the sample. A mobility distribution estimation unit 129 calculates distribution of the mobility of protic solvent in the sample, based on the mobility at a plurality of positions of the sample. The output unit 132 outputs the distribution of mobility.

As shown in FIG. 13, the data processing unit 179 has a calculation unit 173 calculating the self-diffusion coefficient of protic solvent, and a correction unit 175 correcting the value calculated by the calculation unit 173, in a manner adapted to the size of the small-sized RF coil 114. The parameter table 127 has a correction parameter storage unit 177 having, stored therein, correction parameters or correction equations relevant to correction by the correction unit 175.

In the calculation unit 173, the self-diffusion coefficient of protic solvent is calculated based on the NMR signals detected by the small-sized RF coil 114, wherein due to smallness of the small-sized RF coil 114 applying the excitation magnetic field, the measured values in this embodiment may shift from those obtained in the measurement using large solenoid coils.

In this case, values of the self-diffusion coefficient may be corrected, as occasion demands, by the correction unit 175. The correction parameter storage unit 177 has, stored therein, correction parameters and methods of correction adapted to the size of the small-sized RF coil 114, the correction unit 175 acquires these information from the correction parameter storage unit 177, and carries out the correction.

As shown in Examples described later, according to the present invention, the measured values equivalent to those obtained when large coils are used, may be obtained by using the small-sized RF coil 114. Because reduction in size of the RF coil is more likely to cause difference in the degree of excitation of the sample, and thereby factors of inducing errors in the measured values, such as non-uniformity in the magnetic field and lowering in the S/N, may generally occur. In contrast, by considering arrangement of the small-sized RF coil, geometry and arrangement of the G coils, and further by adopting a configuration having the switching unit provided therein, such factors may be excluded, and thereby influences of the size of the RF coil possibly exerted on the measured values may be reduced.

However, when the small-sized RF coil 114 is extremely minimized, influences of the size of RF coil exerted on the measured value may arise. Investigations into the influences by the present inventors made clear that the measured values obtained by using the small-sized RF coil may be converted into exact values by using a predetermined constant. The conversion includes embodiments of multiplying a predetermined constant, or of adding a predetermined constant, either of which may be selected depending, for example, on the properties of the sample. Exact measured values free from influences of the size may be obtained by preliminarily determining such constant, by preliminary experiment using the target sample to be measured.

Reasons why the extremely minimized small-sized RF coil 114 may affect the measured values are as follow.

For the case of large cylindrical coils, insertion of the sample into the coil allows the sample to be uniformly irradiated over the entire range thereof with the oscillating magnetic field for excitation, and thereby the magnetization may be excited in a uniform, or almost uniform manner. The large cylindrical coils are originally designed and manufactured so as to allow uniform irradiation. By using the large cynlindrical coils, a constant self-diffusion coefficient may be obtained, irrespective of their diameter, geometry, number of turns and so forth.

On the other hand, the small-sized RF coil 114 cannot uniformly excite the sample over the entire range thereof, because the coil is smaller than the sample. The position close to the center of the coil is irradiated by the oscillating magnetic field most strongly, but the excitation pulse intensity induced by to the oscillating magnetic field becomes weaker at the position more distant therefrom.

The NMR signals emitted by such non-uniform excitation contain magnetization having various angles of excitation mixed therein, and therefore the phase of magnetization may not uniformly align. As a consequence, the NMR signals received by the coil as a total of these non-uniformity may be different from that obtained under uniform excitation. Exemplary states different from those under uniform excitation include that the echo-peak does not appear as a laterally symmetrical smooth mountain shape, and that the position of maximum intensity shifts on the time axis.

If the self-diffusion coefficient under application of the gradient magnetic field is calculated based on the "NMR signals emitted by thus non-uniform excitation pulses", the results may be different from those obtained by the large coils. Moreover, use of the small-sized RF coil may fluctuate the self-diffusion coefficient, typically depending on the geometry, number of turns and so forth of the small-sized RF coil.

Second Embodiment

Figure 19:
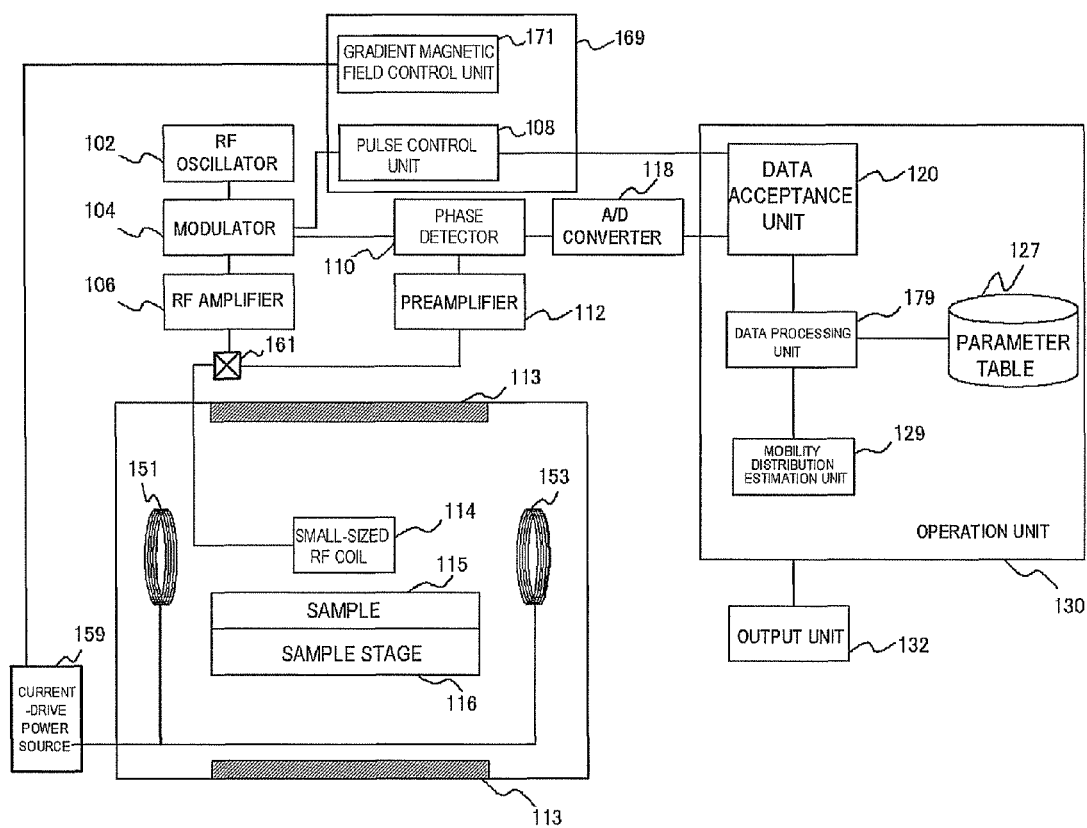
FIG. 19 is a drawing showing a schematic configuration of the mobility measuring instrument according to a second embodiment.

FIG. 19 is a drawing showing a configuration of the mobility measuring instrument of this embodiment. Basic configuration of the instrument shown in FIG. 19 is similar to that of the instrument shown in the first embodiment (FIG. 12), except for arrangement of the G coils for applying the gradient magnetic field.

The G coil 151 and the G coil 153 are provided at positions where the small-sized RF coil 114 is kept therebetween in the in-plane direction of a plane containing the small-sized RF coil 114.

Third Embodiment

Figure 20:
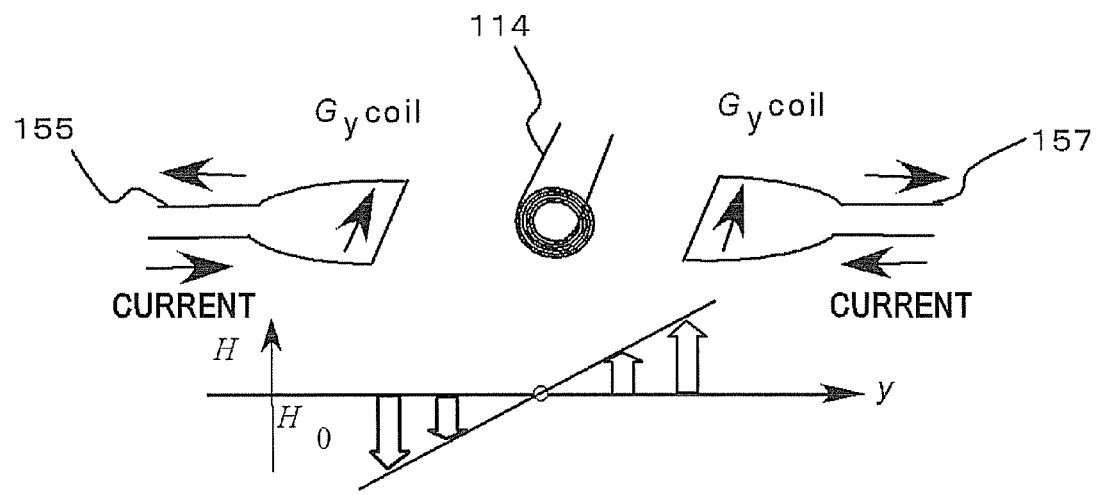
FIG. 20 is a drawing explaining an arrangement of a pair of G coils in the mobility measuring instrument according to a third embodiment.
Figure 21:
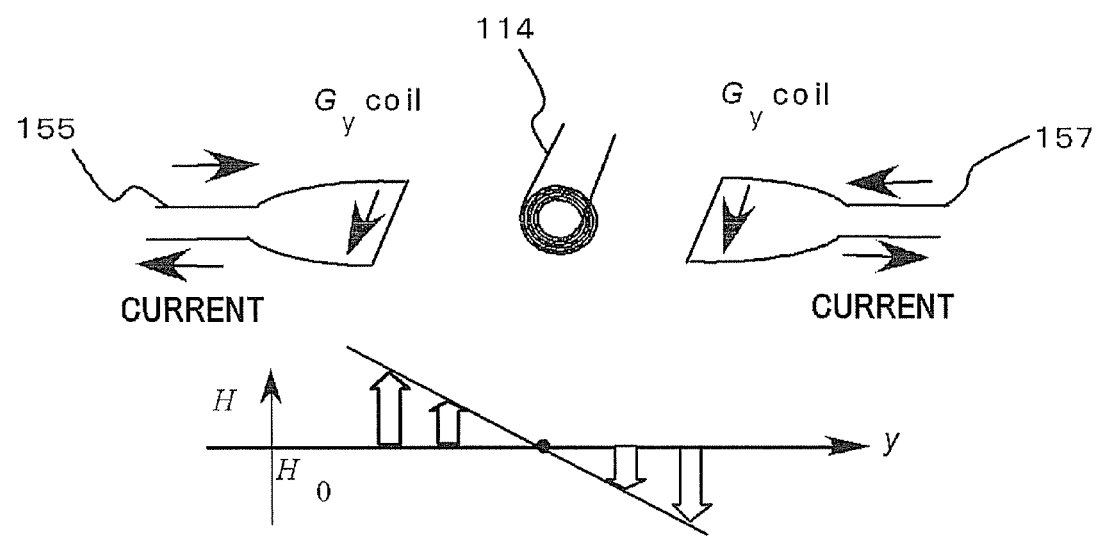
FIG. 21 is a drawing explaining an arrangement of a pair of G coils in the mobility measuring instrument according to a third embodiment.

FIG. 20 and FIG. 21 are drawings showing another example of the G coils. Basic configuration of the instrument, except the G coils, is similar to those shown in FIG. 12 and FIG. 19.

Both of the G coil 155 and the G coil 157 are planar coils, and are disposed in the same plane with the small-sized RF coil 114. The individual G coils have a semicircular geometry, and are opposingly disposed so as to face the individual chords of semicircle towards the small-sized RF coil 114.

The sample 115 has a plate- or a sheet-like geometry, wherein the G coil 155, the G coil 157 and the small-sized RF coil 114 are respectively disposed on a plane parallel to the plane containing the sample 115.

In FIG. 20, the sample 115 is disposed in parallel with the x-y plane. A pair of G coils composed of the G coil 155 and the G coil 157 are disposed on the same side of the main surface of the sample 115, and apply the gradient magnetic field Gz inclined in the z-direction. By supplying current to each of these G coils in a predetermined direction, the gradient magnetic field is formed as shown in FIG. 20.

In FIG. 20 and FIG. 21, the current is supplied in the direction indicated by the arrows. FIG. 20 and FIG. 21 show inverted directions of current, and thereby the direction of gradient of the gradient magnetic field is also inverted.

The configuration in the above, having the G coil 155 and the G coil 157 disposed on the same side of the sample 115, raises advantages described below:

First, alignment of the G coils and the sample 115 may be easier than in the configuration of the first embodiment having two upper and lower G coils opposed while placing the sample 115 in between. Therefore, the gradient magnetic field may be formed under good controllability.

Second, the gradient magnetic field application unit can be downsized, making it possible to realize more local measurement, and more precise measurement of distribution of mobility.

Figure 22:
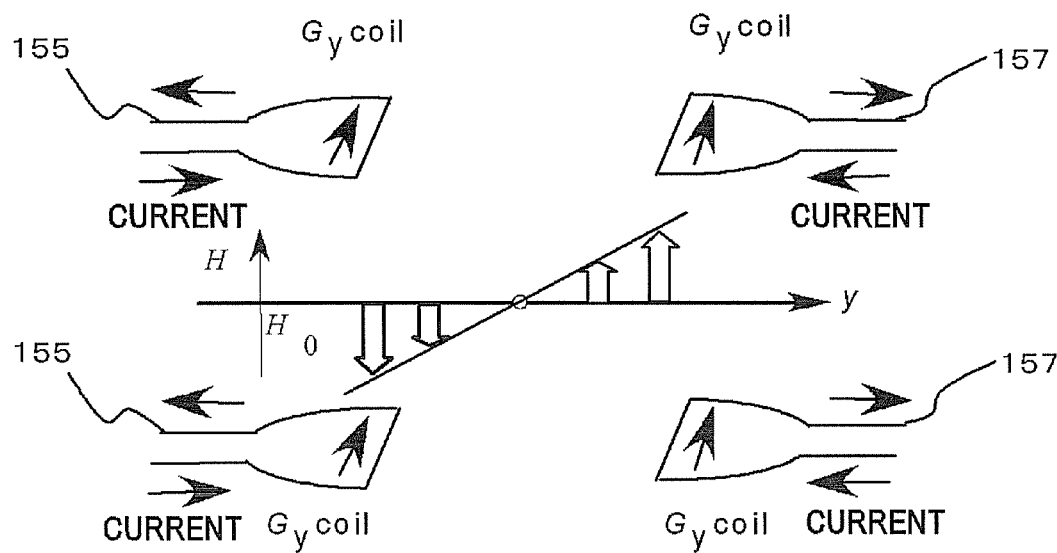
FIG. 22 is a drawing explaining an arrangement of G coils in the mobility measuring instrument according to a third embodiment.

Although the cases using the semicircular G coils have been described, the modes of arrangement are not limited to those described in the above, allowing adoption of various modes of arrangement. For example, a pair of G coils were disposed on one side of the sample 115 in FIG. 20 and FIG. 21, it is also allowable to respectively dispose a pair of G coil respectively on both sides of the sample 115, using four G coils in total, so as to apply the gradient magnetic field to the sample 115. FIG. 22 shows this sort of configuration. By adopting the configuration shown in FIG. 22, the gradient magnetic field may be formed in the sample 115 in a more stable manner.

Fourth Embodiment

This embodiment relates to the geometry, number of use, and arrangement of the coils, for applying the gradient magnetic field, of the mobility measuring instrument. In this embodiment, a plurality of small-sized RF coils 114 are provided, wherein the instrument is configured so that the plurality of small-sized RF coils 114 apply the oscillating magnetic field for excitation to a plurality of positions of the sample 115, and acquire the NMR signals corresponded to the oscillating magnetic field for excitation and the gradient magnetic field, and so that the operation unit 130 calculates the mobility at the plurality of positions of the sample 115.

Figure 23:
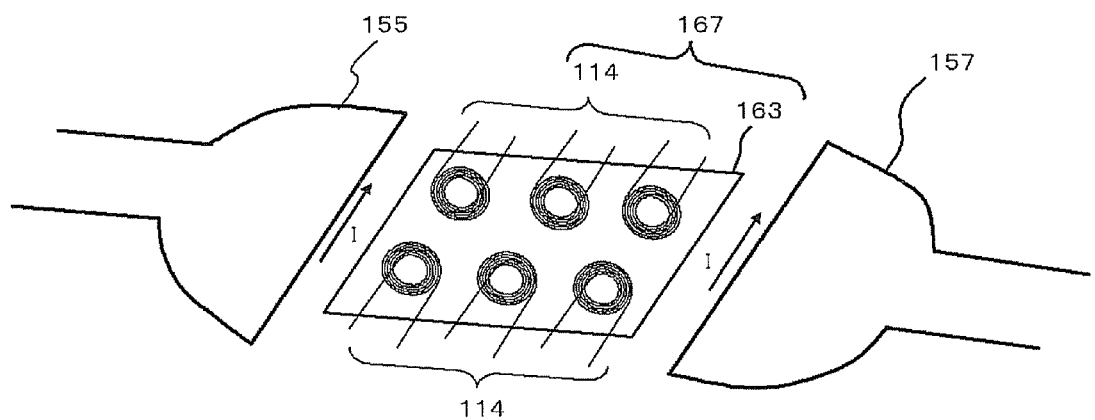
FIG. 23 is a drawing showing an exemplary configuration of a sensor unit in a fourth embodiment.

FIG. 23 is a drawing showing another exemplary configuration of the sensor unit of the instrument shown in FIG. 19. In this example, a plurality of small-sized RF coils 114 are arrayed between the G coil 155 and the G coil 157 having the geometry previously described referring to FIG. 20. Each small-sized RF coil 114 is immobilized on a substrate composed of an insulating material, so as to form a sensor sheet 167.

Figure 24:
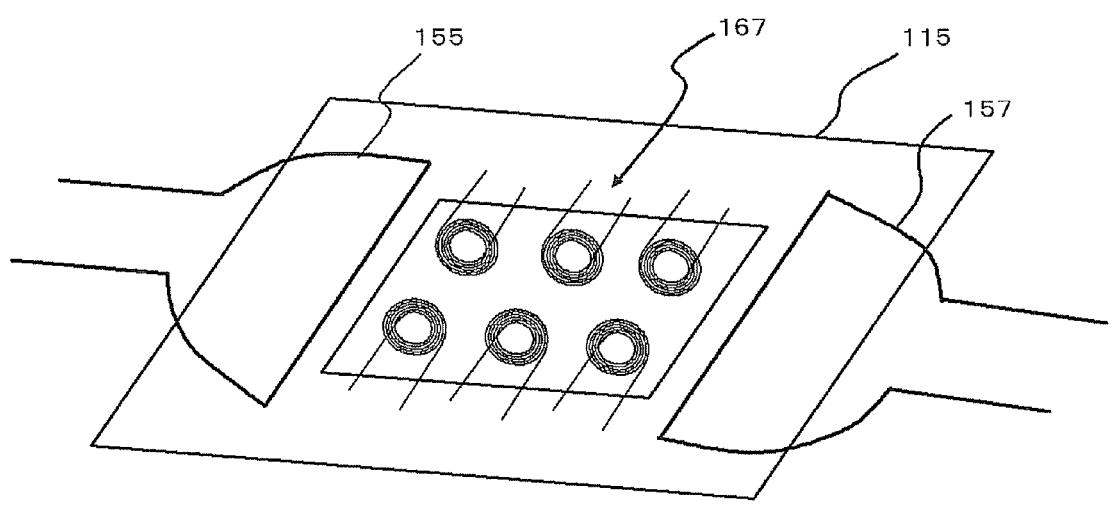
FIG. 24 is a drawing showing a state of arrangement of a sensor unit shown in FIG. 23 above one surface of the sample.

FIG. 24 is a drawing showing a state of arrangement of the sensor sheet 167 shown in FIG. 23 on one surface of the sample 115. In the actual measurement, the sensor sheet 167 and the sample 115 are arranged according to a positional relation shown in the drawing. The sensor sheet 167 and the sample 115 may be in contact with, or distant from each other.

According to the configuration described in the above, application of the magnetic field and acquisition of the NMR signals with respect to the individual small-sized RF coils 114 may be executed by a single processing means, so that multi-point measurement may be realized at the same time only with a simple configuration of the instrument.

Figure 25:
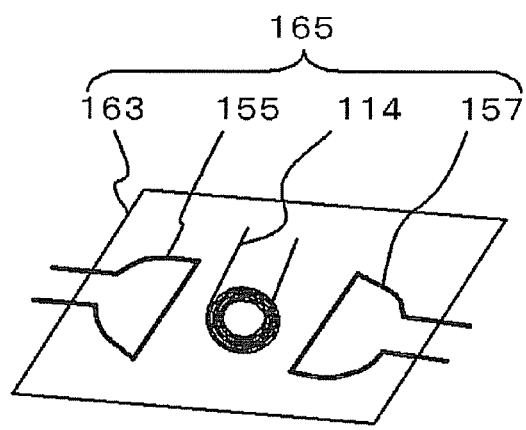
FIG. 25 is a drawing showing a modified example of FIG. 23.
Figure 25:
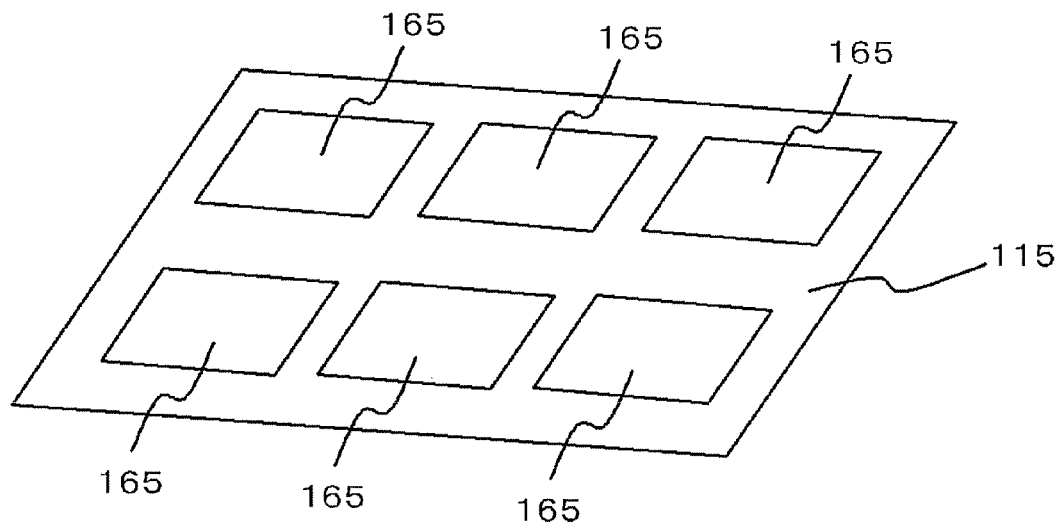

FIG. 25 is a drawing showing another example of the sensor unit. In this example, a plurality of sensor sheets 165 are bonded to the surface of the sample 115. Each sensor sheet 165 is configured as shown in FIG. 25(a), having a substrate 163, and the G coil 155, the G coil 157 and the small-sized RF coil 114 arranged on the substrate 163. The small-sized RF coil 114 is disposed between the G coil 155 and the G coil 157.

Paragraphs below will explain operations and effects obtainable by the first to fourth embodiments having been described in the above.

First, by using the small-sized RF coil bonded to a polymer film, the self-diffusion coefficient is measurable as mobility of water molecules in the film in an local region as small as the diameter or around of the coil.

Second, measurement time of mobility of water molecules can be shortened within several seconds, for example within 5 seconds. In these examples, the mobility is measured using spiral small-sized RF coil (s) based on the PGSE method, so that the mobility in a local region as small as the diameter or around of the coil can be measured within a time as short as 5 seconds or around with high sensitivity. Although the small-sized RF coil having a diameter of 2 mm was shown in these examples, the mobility of protic solvent can be measured in a micro-region of the polymer film if the diameter is further shrunk.

Third, for the case where the polymer film is used for batteries such as solid-polymer-electrolyte fuel cells, the mobility of the water molecules in the polymer film can be measured even during power generation.

Fourth, making use of spin-spin relaxation time constant depending on the water content retained by the polymer film allows the measurement with unprecedented sensitivity.

Fifth, also the water content can be measured at the same time. By using the same measuring instrument, the both can be measured simply by changing the pulse sequence (computer control program). Measurement of both of the water content and the water mobility will be detailed later in fifth embodiment to tenth embodiment.

Sixth, making use of that the water content and the mobility of water molecules in the film can be measured within a short time, it is made possible to monitor the water content and mobility of the film, and to control the amount of steam or water for moistening the film so as to keep an appropriate water content.

Seventh, by reducing the size of the small-sized surface RF coil as being smaller than the thickness of the polymer film, the mobility of water only in the surficial portions is measurable, allowing local measurement also in the thickness-wise direction.

Eighth, by bonding the RF coils smaller than the thickness of the polymer film on both sides, that are on the fuel side and on the oxidant side, of the polymer film, the water content and mobility can be monitored on both sides of the film, allowing provision of data for elucidating causes for lowered output of power generation.

Fifth Embodiment to Tenth Embodiment

Next, instruments measuring local water content and local mobility will be explained in the following embodiments. In actual measurement of local water content and local mobility, echo waveforms different from the usual may obtained for some reason, and may fail in calculating the water content and the self-diffusion coefficient which should fall in appropriate ranges.

Possible reasons therefor may be as follow:

Influences of time-dependent fluctuation and spatial non-uniformity of the static magnetic field may exist.

The oscillating magnetic field for excitation applied from the small-sized RF coil becomes non-uniform in the sample.

The echo waveform may be disturbed due to FID contamination caused by non-ideal 180° pulse for excitation.

Influences of noises coming from the RF power amplifier, the preamplifier, the current-drive power source and so forth.

External noise may contaminate the small-sized RF coil and the transmission system, and is consequently contained in the echo signals.

When the water content or the mobility is determined, it has therefore been necessary for the user of the measuring instrument to check the calculated water content and mobility, and to delete erroneous data, for correct understanding of the water content and the mobility.

In contrast, the present embodiments determine the amount of movement based on the water content and mobility calculated by the measuring instrument, so that the measuring instrument is expected to internally delete erroneous data of the water content and mobility. The measuring instrument disclosed in the following embodiments are configured as being solved in the problem of deletion of erroneous data. More specifically, in order to delete erroneous data caused by the above-described reasons, the instruments of these embodiment are configured so as to calculate the water content and mobility small in variation and excellent in probability, by providing various check functions before the water content and the mobility are calculated from the NMR signals.

Fifth Embodiment

Figure 26:
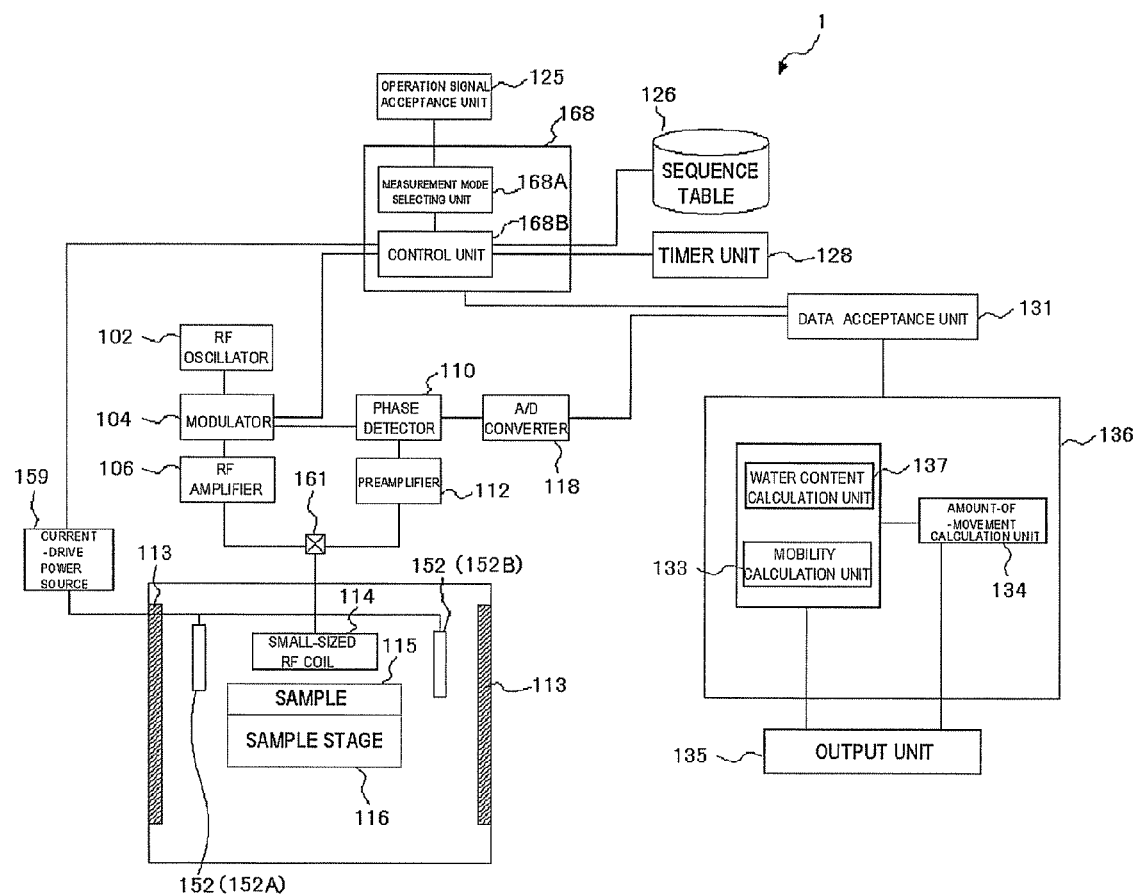
FIG. 26 is a drawing showing a configuration of the measuring instrument according to a fifth embodiment.

FIG. 26 is a drawing showing a schematic configuration of a measuring instrument 1 according to this embodiment.

The measuring instrument 1 is an instrument capable of measuring mobility of protic solvent (water, in this embodiment) (self-diffusion coefficient, in this embodiment), water content and amount of movement of water molecules at a specific position of the sample (sample 115) using the NMR method, and has:

a sample stage 116 on which the sample 115 is placed;

a static magnetic field application unit (magnet 113) applying a static magnetic field to the sample 115;

a gradient magnetic field application unit (G coil 152 (G coil 152A, G coil 152B)) applying a gradient magnetic field to the sample 115;

a small-sized RF coil 114 smaller in size than the sample 115, applying an oscillating magnetic field for excitation to the sample 115, and acquiring a magnetic resonance signal corresponded to the oscillating magnetic field for excitation and the gradient magnetic field;

a measurement mode change-over control unit 168 allowing change-over between a first measurement mode allowing measurement of water content by applying the oscillating magnetic field for excitation, and a second measurement mode allowing measurement of self-diffusion coefficient by applying gradient magnetic field and the oscillating magnetic field for excitation; and an operation unit 136 having a first calculation unit (water content calculation unit) 132 calculating the water content at the specific position of the sample 115, a second calculation unit (mobility calculation unit) 133 calculating the self-diffusion coefficient at the specific position of the sample 115, and a third calculation unit (amount-of-movement calculation unit) 134 calculating the amount of movement at the specific position of the sample 115.

First, the sample 115 and an instrumental configuration around the sample 115 will be explained.

Similarly to as in the above-described embodiments, the magnet 113 applies the static magnetic field over the entire portion of the sample 115. In this embodiment, the oscillating magnetic field for excitation is applied to the sample 115, while being applied with the static magnetic field, thereby the water content is measured.

The sample 115 is also applied with the oscillating magnetic field for excitation and the gradient magnetic field pulses, while being applied with the static magnetic field, thereby the self-diffusion coefficient is measured.

The small-sized RF coil 114 applies the oscillating magnetic field for excitation to the specific portion of the sample, similarly to as described in the foregoing embodiments. The NMR signals corresponded to the oscillating magnetic field for excitation, and the NMR signals corresponded to the gradient magnetic field are acquired.

Figure 27:
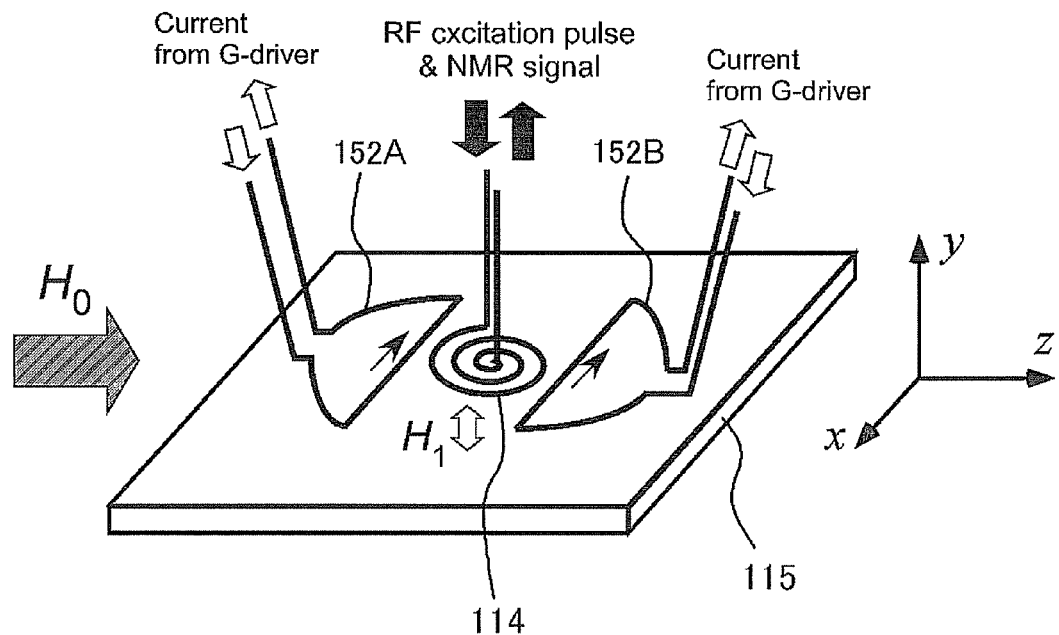
FIG. 27 is a schematic drawing showing an arrangement of the G coil and the small-sized RF coil in the measuring instrument of the fifth embodiment.
Figure 28:
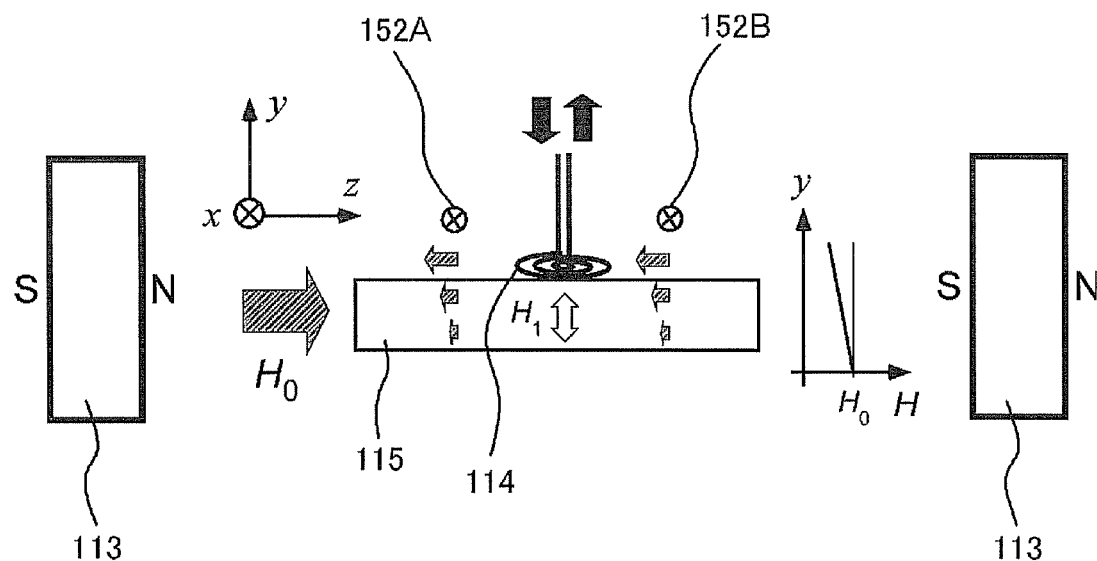
FIG. 28 is a schematic drawing showing an arrangement of the G coil, the small-sized RF coil and a magnet in the measuring instrument of the fifth embodiment.

The oscillating magnetic field for excitation $H_1$ applied by the small-sized RF coil 114, configured as a planar spiral coil, need be normal to the static magnetic field $H_0$ applied by the magnet 113 (see FIGS. 27, 28).

The static magnetic field, illustrated in the drawing as being applied in the direction of the z-axis, may be applied in the direction of the x-axis. If the oscillating magnetic field for excitation $H_1$ is applied in the direction of the y-axis, the static magnetic field $H_0$ may be in the direction normal to the y-axis (in the direction along the xz-plane). In short, it is good enough that the oscillating magnetic field for excitation $H_1$ and the static magnetic field $H_0$ are applied as being nearly normal to each other.

The oscillating magnetic field (oscillating magnetic field for excitation) applied by the small-sized RF coil 114 is produced, similarly to as in the forgoing embodiments, by cooperation of the RF oscillator 102, the modulator 104, the RF amplifier 106, the pulse control unit 108, the switching unit 161 and the small-sized RF coil 114. In this embodiment, the A/D converter 118 subjects the NMR signals to A/D conversion, and sends them to the operation unit 136.

The oscillating magnetic field for excitation applied by the small-sized RF coil 114 to the sample 115 may be a pulse sequence typically composed of:
(a) a 90° pulse; and
(b) a 180° pulse applied time τ after the pulse of (a).

Correlation between peak intensity of the NMR signals based on the spin-spin and the self-diffusion coefficient D of protic solvent in the sample 115, and between $T_2$ relaxation time constant and the water content in the sample 115 may be obtained, also by using a pulse sequence having the 90° pulse in a first phase, and the 180° pulse in a second phase 90° shifted from the first phase.

As previously described in the first embodiment, use of the small-sized RF coil 114 may raise difficulty in adjusting intensity of the excitation pulses of (a) and (b) in the above. Variation in the ratio of angle of excitation based on (a) and (b) disables exact measurement of water content and the self-diffusion coefficient.

Therefore in this case, similarly to as in the first embodiment, the pulse control unit 108 is configured to execute another sequence having, in addition to the above-described pulse sequence, a step of applying a 180° pulse time τ earlier than the 90° pulse (a). By comparing behaviors of the NMR signals (echo signals) obtained by two these sequences (for example, whether degrees of phase inversion and signal intensity of phase waveform obtained by the phase detector are equivalent or not), whether the excitation pulse intensities of the 90° pulse (a) and the 180° pulse (b) are exact or not may be discriminated.

The switching unit 161 is provided at a branching portion where the small-sized RF coil 114, the RF excitation pulse generating unit and the NMR signal detecting unit are connected.

Similarly to the RF signal generation unit in the first embodiment, the RF excitation pulse generating unit is composed of the RF oscillator 102, the modulator 104 and the RF amplifier 106, and generates RF excitation pulses allowing the small-sized RF coil 114 to generate the oscillating magnetic field for excitation. The NMR signal detecting unit is composed of the preamplifier 112, the phase detector 110 and the A/D converter 118, similarly to as in the first embodiment, and detects the NMR signals acquired by the small-sized RF coil 114, and sends the NMR signals to the operation unit 130.

The switching unit 161 has a function of allowing switching between:
a first state having the small-sized RF coil 114 and the RF excitation pulse generating unit (RF amplifier 106) connected with each other; and
a second state having the small-sized RF coil 114 and the NMR signal detecting unit (phase detector 110) connected with each other, similarly to as described in the first embodiment.

The function of the switching unit 161 herein is same as that described in the first embodiment.

As shown in FIGS. 27, 28, the G coil 152A and the G coil 152B are arranged so that they can apply the gradient magnetic field to the sample 115. The G coil 152A and the G coil 152B may adopt those having various geometries, wherein planar coils are adopted in this embodiment. The G coil 152A and the G coil 152B have a semicircular geometry, and are opposingly disposed so as to face the individual chords with each other, while placing the small-sized RF coil 114 in between.

The G coil 152A and the G coil 152B are disposed in parallel with the surface (x-z plane) of the sample 115.

The G coil 152A and the G coil 152B are disposed above the small-sized RF coil 114. By virtue of this configuration, the gradient magnetic field may be formed on the center axis of the small-sized RF coil 114, as having the gradient of the magnetic field in the direction of y-axis.

A sh s provided respectively between the small-sized RF coil 114 and the G coil 152A, and between the small-sized RF coil 114 and the G coil 152B. These shutoff shields prevent noise from the G coil 152A and the G coil 152B from adversely affecting the small-sized RF coil 114. The shutoff utoff shield, not shown, i shields have a thickness capable of preventing the noise from passing therethrough, but allowing the magnetic field to pass therethrough.

When the water content and the self-diffusion coefficient are measured, the small-sized RF coil 114 is projected towards the sample 115 side, out from the G coil 152A and the G coil 152B, to thereby allow only the small-sized RF coil 114 to contact with the sample 115.

As shown in FIG. 26, application of the RF pulses from the RF oscillator 102 via the modulator 104 to the small-sized RF coil 114, and supply of the pulse current via the current-drive power source 159 to the G coil 152A and to the G coil 152B are controlled by the measurement mode change-over control unit 168. The measurement mode change-over control unit 168 contains a measurement mode selecting unit 168A and a control unit 168B.

The measurement mode selecting unit 168A receives a request entered by the operator, and selects a measurement mode corresponded to the received request. In this embodiment, either one of a first measurement mode for measuring the water content at a specific position of the sample 115, and a second measurement mode allowing measurement of mobility (self-diffusion coefficient) of water molecules at the specific position of the sample 115 is selected.

Figure 29:
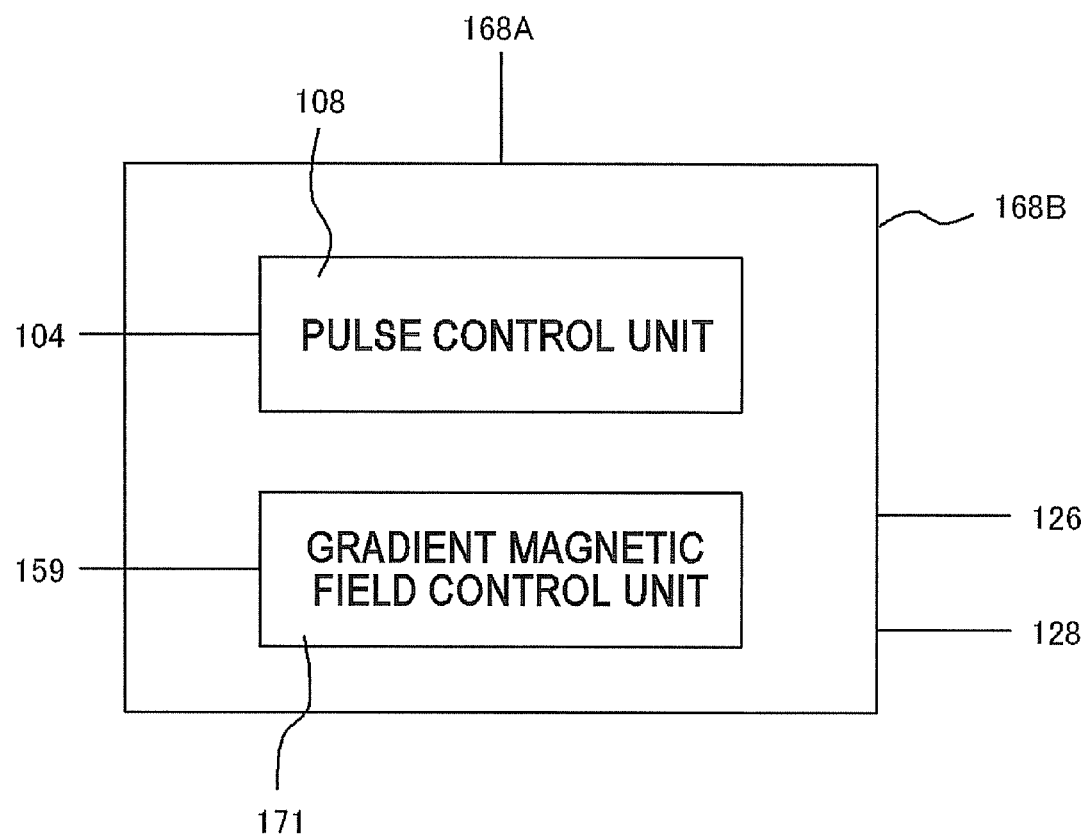
FIG. 29 is a block diagram showing a configuration of the control unit of the measuring instrument of the fifth embodiment.

FIG. 29 is a drawing showing an exemplary configuration of the control unit 168B. The control unit 168B has a pulse control unit 108 controlling operations of the modulator 104, and a gradient magnetic field control unit 171 controlling operations of the current-drive power source 159.

The control unit 168B is connected with a sequence table 126, wherein the sequence table 126 stores sequence data of RF pulses used when the water content is measured, and a sequence data determining a sequence of pulse current producing the RF pulses and gradient magnetic field when the self-diffusion coefficient is measured. More specifically, a first timing diagram having, set therein, time at which the RF pulses are generated and the intervals thereof when the water content is measured, and a second timing diagram having, set therein, time at which the RF pulses and the pulse current for generating the gradient magnetic field and the intervals thereof when the self-diffusion coefficient is measured, are stored.

In the sequence table 126, intensity of the RF pulses applied based on the first timing diagram is stored. Also intensity of the RF pulses and the pulse current for generating the gradient magnetic field applied based on the second timing diagram are stored in the sequence table 126.

To the control unit 168B, a timer unit 128 is connected.

Thus-configured control unit 168B generates the RF pulses and the pulse current for producing the gradient magnetic field, based on the sequence data acquired from the sequence table 126, and on the time measured by the timer unit 128.

For example, when the operator enters a request demanding execution of both of measurement of water content and measurement of self-diffusion coefficient, an operation signal acceptance unit 125 connected to the measurement mode change-over control unit 168 accepts the request. The operation signal acceptance unit 125 sends the request to the measurement mode change-over control unit 168. The measurement mode selecting unit 168A selects the measurement mode allowing measurement of water content, and sends information specifying the selected mode to the control unit 168B and to the data acceptance unit 131. The data acceptance unit 131 sends the measurement mode specifying information to the operation unit 136. The operation unit 136 executes a correspondent operation processing, based on the measurement mode specifying information.

If the measurement mode specifying information indicates the first measurement mode allowing measurement of water content, the measured data is sent to the water content calculation unit 137, and if the measurement mode specifying information indicates the second measurement mode allowing measurement of self-diffusion coefficient, the measured data is sent to the mobility calculation unit 133, thereby predetermined processing are executed in the individual calculation units.

The control unit 168B which received the measurement mode specifying information demanding measurement of water content reads the sequence data for the measurement of water content out from the sequence table 126. The pulse control unit 108 of the control unit 168B then controls operations of the modulator 104, and applies the oscillating magnetic field for excitation to the sample 115 according to a predetermined pulse sequence.

Next, the measurement mode selecting unit 168A selects the measurement mode allowing measurement of self-diffusion coefficient, and then sends the measurement mode specifying information corresponded to the selection to the control unit 168B and to the data acceptance unit 131. The data acceptance unit 131 sends the measurement mode specifying information indicating the measurement mode selected by the measurement mode selecting unit 168A to the operation unit 136, and the mobility calculation unit 133 of the operation unit 136 receives the measurement mode specifying information indicating the measurement mode selected by the measurement mode selecting unit 168A.

The control unit 168B reads the sequence data for the measurement of self-diffusion coefficient out from the sequence table 126. The pulse control unit 108 of the control unit 168B controls operation of the modulator 104, and the gradient magnetic field control unit 171 controls operations of the current-drive power source 159.

The oscillating magnetic field for excitation is applied to the sample 115 according to a predetermined pulse sequence, and the oscillating magnetic field for excitation and the gradient magnetic field are further applied according to a predetermined pulse sequence.

Order of the measurement of water content and the measurement of self-diffusion coefficient is not specifically limited, wherein the measurement of self-diffusion coefficient may precede the measurement of water content.

When the operator entered a request demanding the measurement of water content only, or the measurement of self-diffusion coefficient only, measurement mode selecting unit 168A of the measurement mode change-over control unit 168 may select the first measurement mode allowing measurement of water content, or the second measurement mode allowing measurement of self-diffusion coefficient, based on the request.

The current-drive power source 159 shown in FIG. 26 is aimed at providing current to the G coil 152A and the G coil 152B. For the current-drive power source 159, a transformer or the like is used, rather than using switching power sources.

When the current-drive power source 159 is not operated, the control is made so as to avoid micro-oscillation of the transistors induced by noise.

It is also allowable to adopt a configuration that the lead wires connected to the G coil 152A and to the G coil 152B are disconnectable, when the current-drive power source 159 is not operated.

By using thus-configured current-drive power source 159, influences of noise from the current-drive power source 159 to the NMR signals may be avoidable.

The instrumental configuration around the sample has been explained. Next paragraphs will explain process blocks of the NMR signals.

As shown in FIG. 26, the operation unit 136 has the water content calculation unit 137 as the first calculation unit, the mobility calculation unit 133 as the second calculation unit, and an amount-of-movement calculation unit 134 as the third calculation unit.

Figure 30:
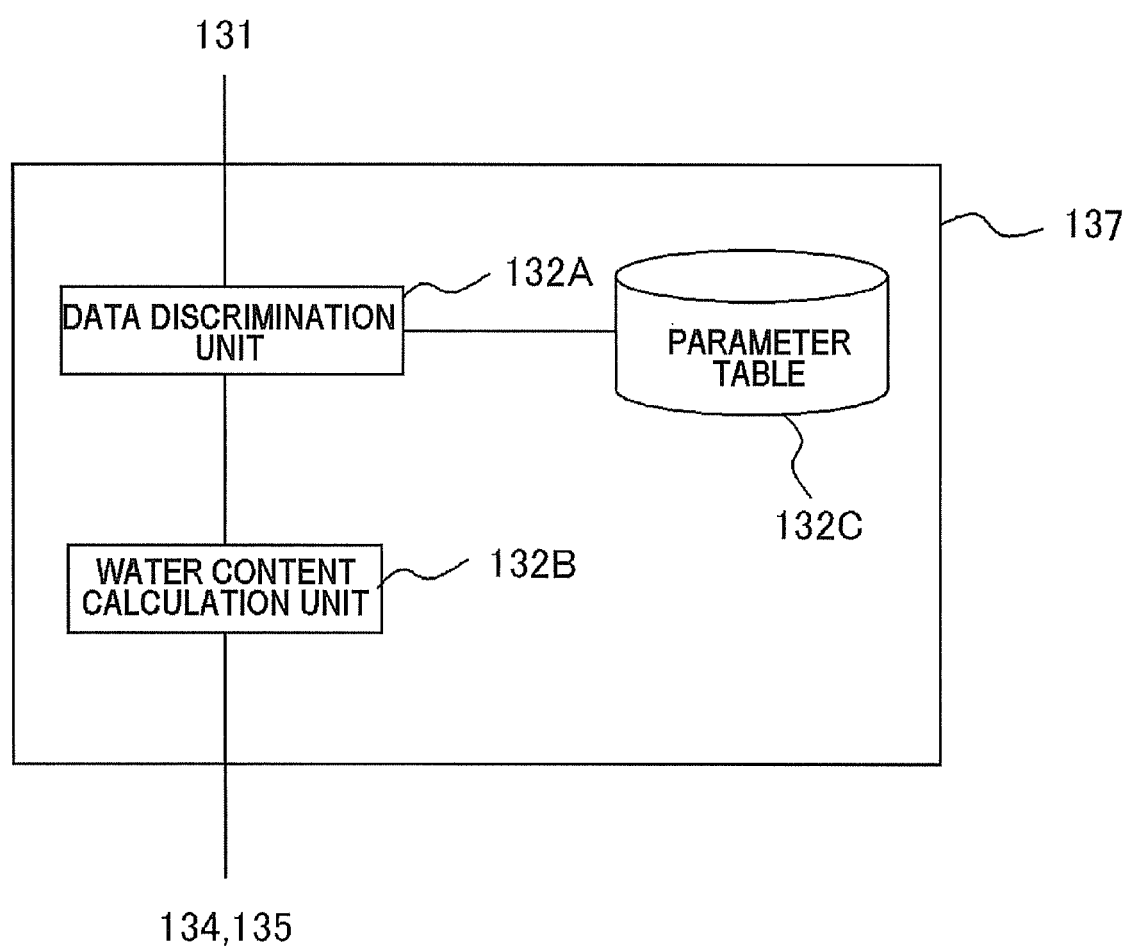
FIG. 30 is a block diagram showing a configuration of a water content calculation unit of the measuring instrument of the fifth embodiment.

First, the water content calculation unit 137 will be explained referring to FIG. 30.

The water content calculation unit 137 calculates the water content at a specific position of the sample 115, based on intensity of the NMR signals obtained by applying the oscillating magnetic field for excitation to the sample 115.

The water content calculation unit 137 has a data discrimination unit 132A, a water content calculation unit 132B, and parameter table 132C for data discrimination.

The data discrimination unit 132A discriminates NMR signals used for calculating the $T_2$ relaxation time constant, referring to the parameter table 132C.

First, the NMR signals accepted by the data acceptance unit 131 are discriminated into the NMR signals having intensity of a predetermined level or higher, and the NMR signals having intensity lower than the predetermined level. Only the NMR signals having intensity of a predetermined level or higher are selected, intensity of these NMR signals are converted to logarithmic values, and linearly approximated by the least squared method. Thereafter, whether difference between the approximation line and the logarithmic values of the NMR signals having intensity of a predetermined level or higher falls in a predetermined range or not is discriminated.

If the difference between the approximation line and the logarithmic values of the NMR signals having intensity of a predetermined level or higher falls in a predetermined range, the NMR signals having intensity of a predetermined level or higher are sent to the water content calculation unit 132B, thereby the $T_2$ relaxation time constant and the water content are calculated.

Because the logarithmic values of intensity of the NMR signals decrease in an exponential manner, logarithmic values of intensity of the NMR signals acquired after the elapse of a certain length of time are stabilized nearly at a constant level. The data discrimination unit 132A discriminates only the NMR signals having the logarithmic values being not stabilized yet at constant, rather than discriminating the NMR signals having the logarithmic values already stabilized at constant, transmits them to the water content calculation unit 132B, to thereby calculates the $T_2$ relaxation time constant and the water content.

Figure 31:
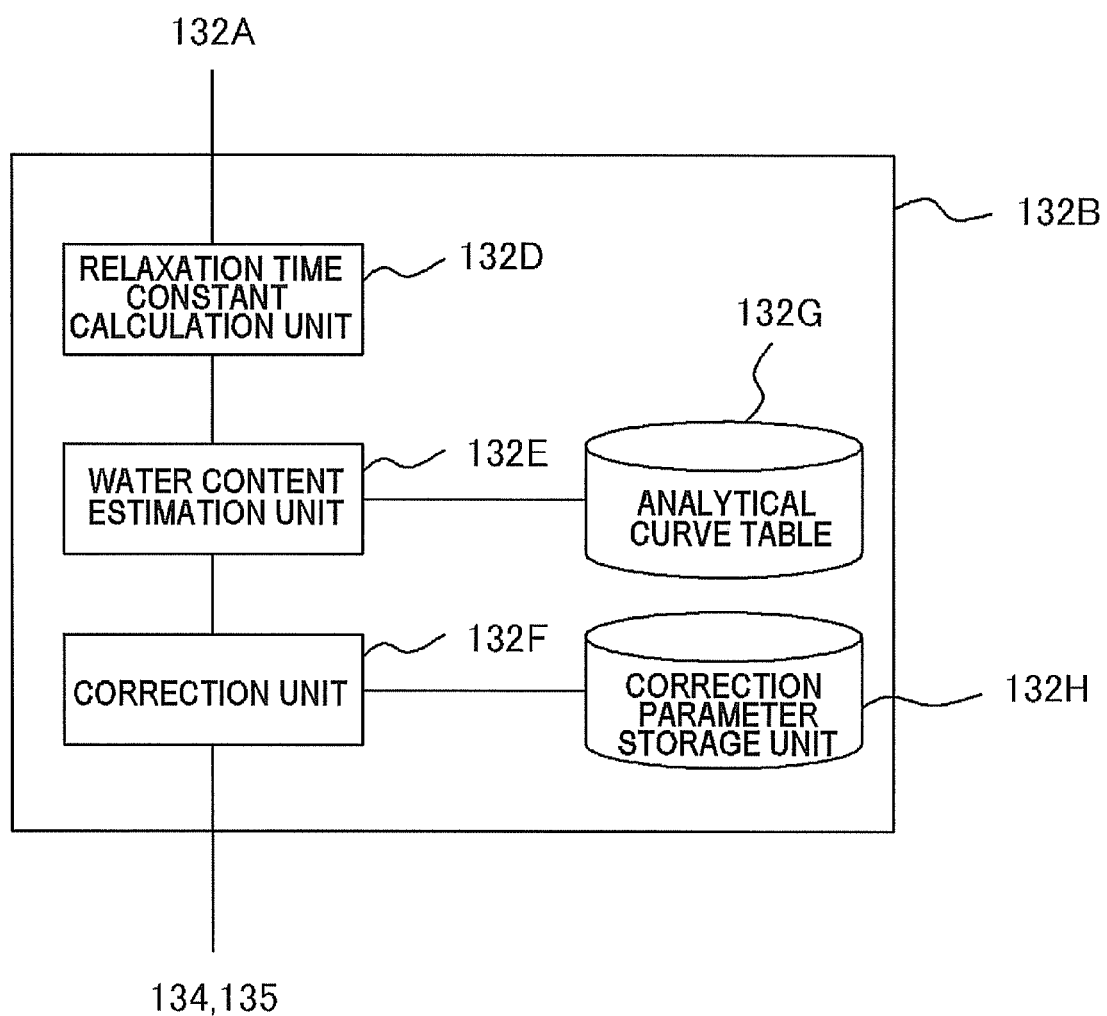
FIG. 31 is a block diagram showing a configuration of a water content calculation unit of the measuring instrument of the fifth embodiment.

As shown in FIG. 31, the water content calculation unit 132B has a relaxation time constant calculation unit 132D calculating the $T_2$ relaxation time constant, a water content estimation unit 132E calculating the water content based on the $T_2$ relaxation time constant, a correction unit 132F, an analytical curve table 132G, and a correction parameter storage unit 132H.

Once the $T_2$ relaxation time constant was calculated by the relaxation time constant calculation unit 132D, the data is sent to the water content estimation unit 132E. The water content estimation unit 132E accesses the analytical curve table 132G, and acquires an analytical curve data corresponded to the sample 115. The analytical curve table 132G has, stored therein, analytical curve data expressing correlations between the water content in the sample and the $T_2$ relaxation time constant, for every type of samples 115.

The water content estimation unit 132E calculates an estimated value of the water content of the sample 115, using thus-acquired analytical curve data and thus-calculated $T_2$ relaxation time constant.

The estimated value of water content calculated by the water content estimation unit 132E is sent to the correction unit 132F. The correction unit 132F corrects the estimated value of water content as being adapted to the size of the small-sized RF coil 114, to thereby calculate the water content.

The relaxation time constant calculation unit 132D calculates the $T_2$ relaxation time constant based on the NMR signals detected by the small-sized RF coil 114, wherein in this embodiment, the measured values may differ from those obtained by using large solenoid coils, because of smallness of the small-sized RF coil 114 applying the oscillating magnetic field for excitation.

In this case, the values of water content may be corrected by the correction unit 132F, as occasion demands. The correction parameter storage unit 132H has, stored therein, correction parameters and methods of correction as being adapted to the size of the small-sized RF coil 114 (adding a predetermined constant as being adapted to the size of the small-sized RF coil 114, or multiplying a predetermined constant, for example), and the correction unit 132F proceeds correction by acquiring the information from the correction parameter storage unit 132H.

Figure 58:
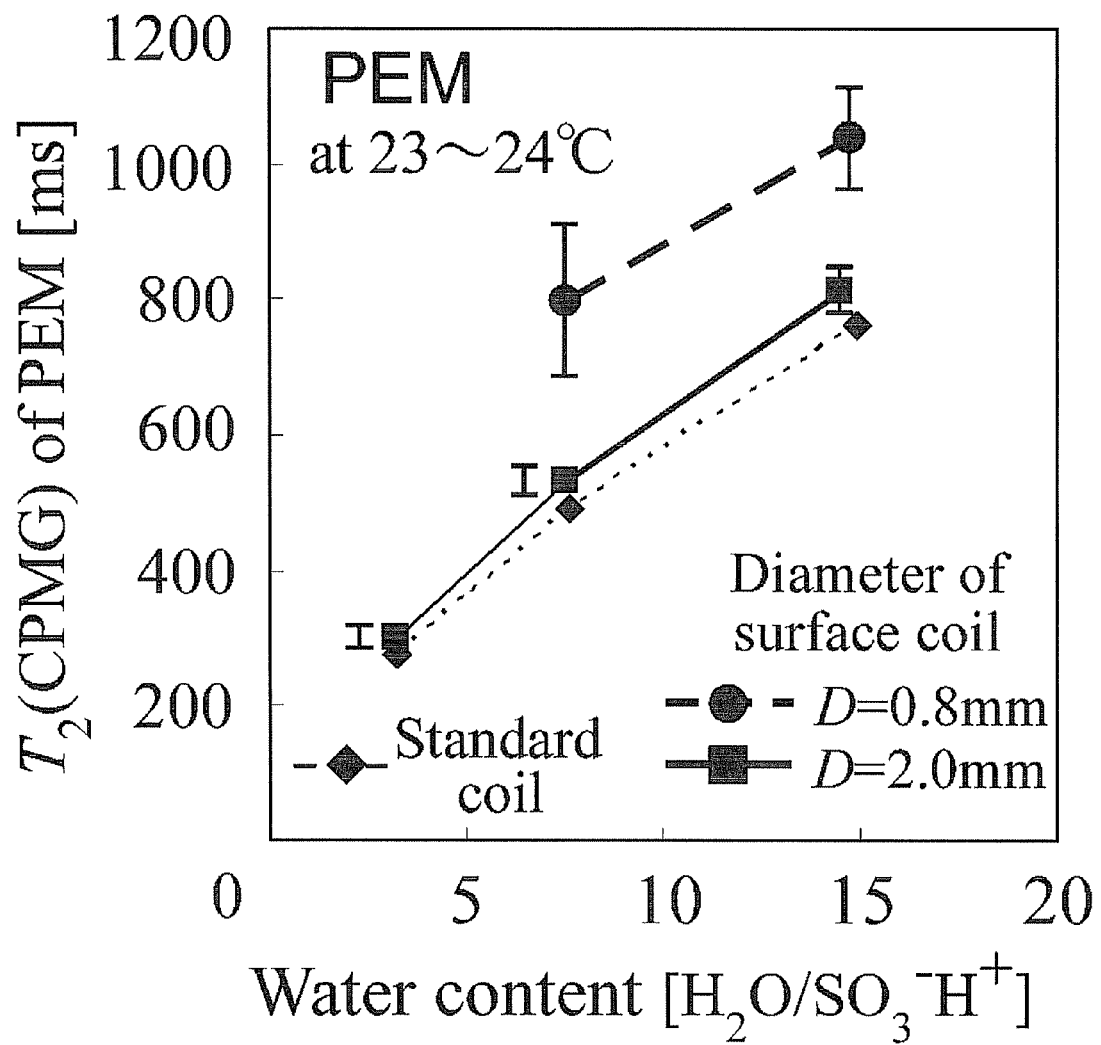
FIG. 58 is a drawing showing results of Example 5.

As previously described in the first embodiment, when the magnetic resonance signals are acquired using the small-sized RF coil, probability of measurement may degrade and variations in the measurement may increase, supposedly because of interference between the magnetic resonance signals and the echo signals to be measured. Accordingly, results of measurement of the $T_2$ (CPMG) relaxation time may increase or decrease as shown in FIG. 58, supposedly depending on the size or geometry of the small-sized RF coil, which is more specifically the outer diameter of the small-sized RF coil, or ratio of the outer and inner diameters.

As the method of preventing interference of unnecessary magnetic resonance signals, one effective method is such as intentionally degrading uniformity in the static magnetic field by constantly applying an extremely weak gradient magnetic field so as to shorten the $T_2^*$ relaxation time constant of FID signals, thereby eliminating influences of the unnecessary magnetic resonance signals before the echo signals to be measured are produced.

This idea is absolutely against a concept of "ensuring spatial uniformity of the static magnetic field at a highest-possible level" required for general NMR measurement. This is ascribable to that, for the case where the small-sized RF coil is used, it is good enough that the static magnetic field is uniform only in the region observable by the small-sized RF coil, and that uniformity in the static magnetic field relatively increases as the small-sized RF coil becomes smaller and smaller. For this reason, the $T_2^*$ relaxation time constant of the FID signals becomes too long, and the method of measurement may be strongly affected by the unnecessary magnetic resonance signals. It may, therefore, be more preferable to intentionally degrade uniformity in the magnetic field, in the region out of the measurable range by the small-sized RF coil, so as to suppress contamination by the unnecessary magnetic resonance signals.

The water content calculated as described in the above is presented by the output unit 135 to the user. Modes of presentation are available in various ways of embodiment, including presentation on a display, output to a printer, and output to a file, without limitations.

Figure 32:
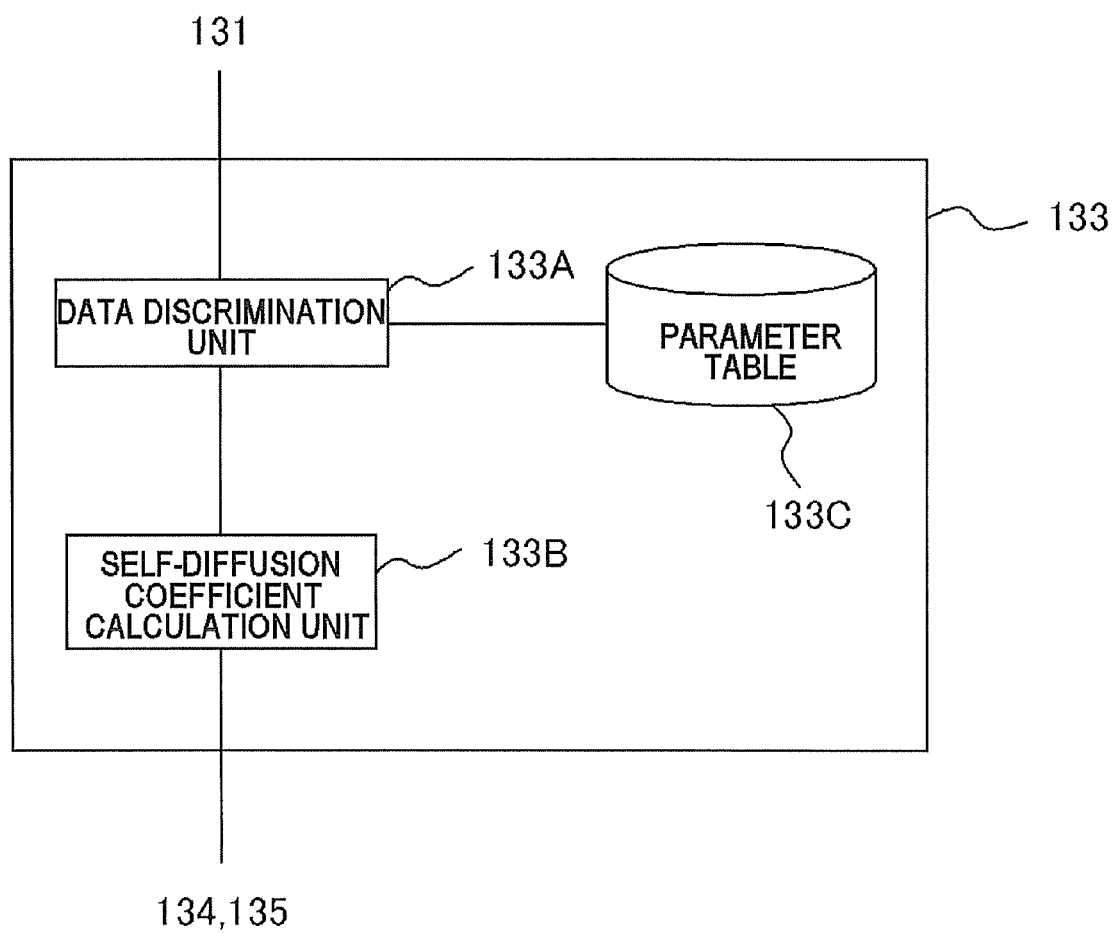
FIG. 32 is a block diagram showing a configuration of a mobility calculation unit of the measuring instrument of the fifth embodiment.

Next, the mobility calculation unit 133 will be explained referring to FIG. 32 and FIG. 33.

Mobility is a physical value expressing readiness of moving of a protic solvent in a sample, as described in the above, typically exemplified by self-diffusion coefficient, mobility and so forth, wherein in this embodiment, the self-diffusion coefficient is calculated as the readiness of moving.

The mobility calculation unit 133 calculates the self-diffusion coefficient of water molecules at the specific position of the sample 115, based on the NMR signal obtained by applying the oscillating magnetic field for excitation, and the NMR signals obtained by applying different gradient magnetic fields, with respect to the sample 115.

The mobility calculation unit 133 has a data discrimination unit 133A, a self-diffusion coefficient calculation unit 133B, and a parameter table 133C for data discrimination.

The data discrimination unit 133A discriminates the NMR signals, referring to the parameter table 133C for data discrimination. The method of discriminating the NMR signals is same as that executed by the data discrimination unit 132A of the water content calculation unit 137.

Figure 33:
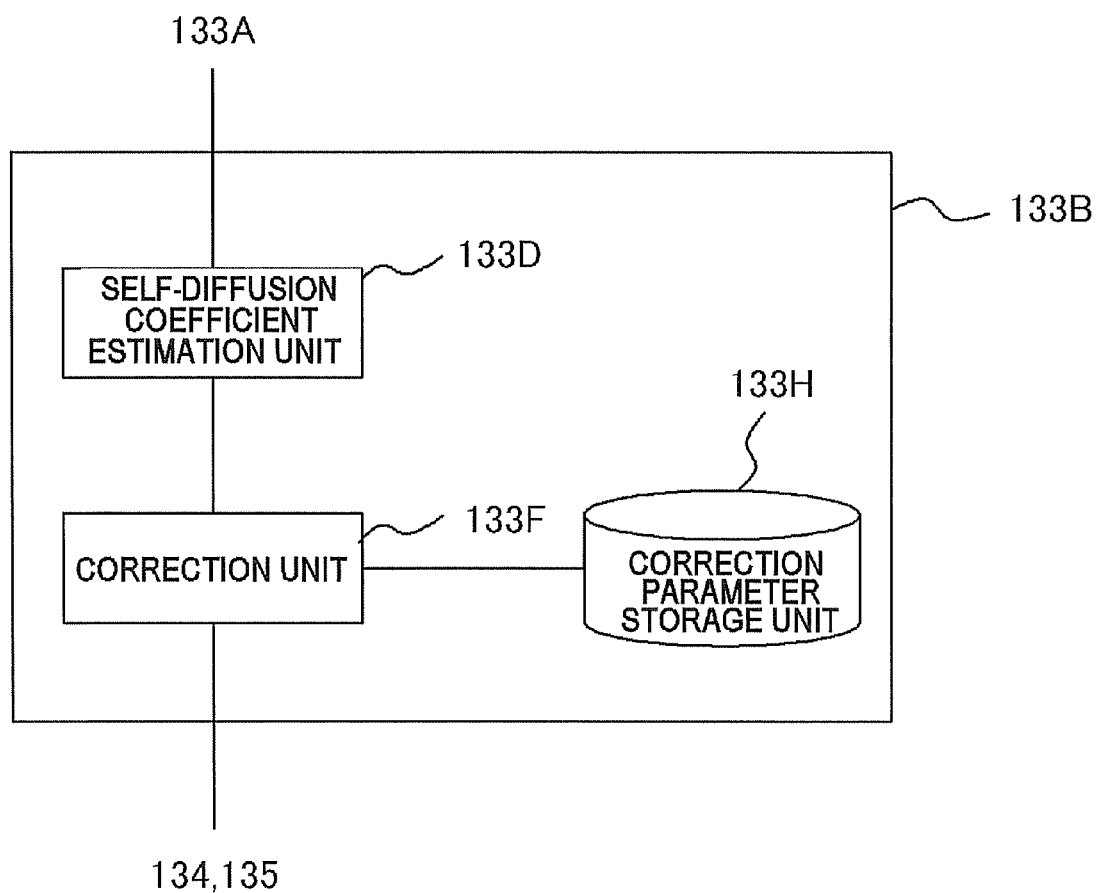
FIG. 33 is a block diagram showing a configuration of a self-diffusion coefficient calculation unit of the measuring instrument of the fifth embodiment.

The self-diffusion coefficient calculation unit 133B has, as shown in FIG. 33, a self-diffusion coefficient estimation unit 133D calculating the self-diffusion coefficient, a correction unit 133F, and a correction parameter storage unit 133H.

The self-diffusion coefficient estimation unit 133D calculates an estimated value of the self-diffusion coefficient, using the equation (II) described in the above, based on the acquired NMR signals.

The correction unit 133F corrects the estimated value of the self-diffusion coefficient calculated by the self-diffusion coefficient estimation unit 133D, in a manner adapted to the size of the small-sized RF coil 114. The correction parameter storage unit 133H has, stored therein, correction parameters or correction equations relevant to correction executed by the correction unit 133F (adding a predetermined constant as being adapted to the size of the small-sized RF coil 114, or multiplying a predetermined constant, for example).

The self-diffusion coefficient estimation unit 133D calculates the estimated value of the self-diffusion coefficient of water based on the NMR signals detected by the small-sized RF coil 114, wherein also in the calculation of the self-diffusion coefficient, the measured values may differ from those obtained by using large solenoid coils, because of smallness of the small-sized RF coil 114 applying the oscillating magnetic field for excitation.

In this case, the values of self-diffusion coefficient may be corrected by the correction unit 133F, as occasion demands. The correction parameter storage unit 133H has, stored therein, correction parameters and methods of correction as being adapted to the size of the small-sized RF coil 114, and the correction unit 133F proceeds correction by acquiring the information from the correction parameter storage unit 133H.

Figure 34:
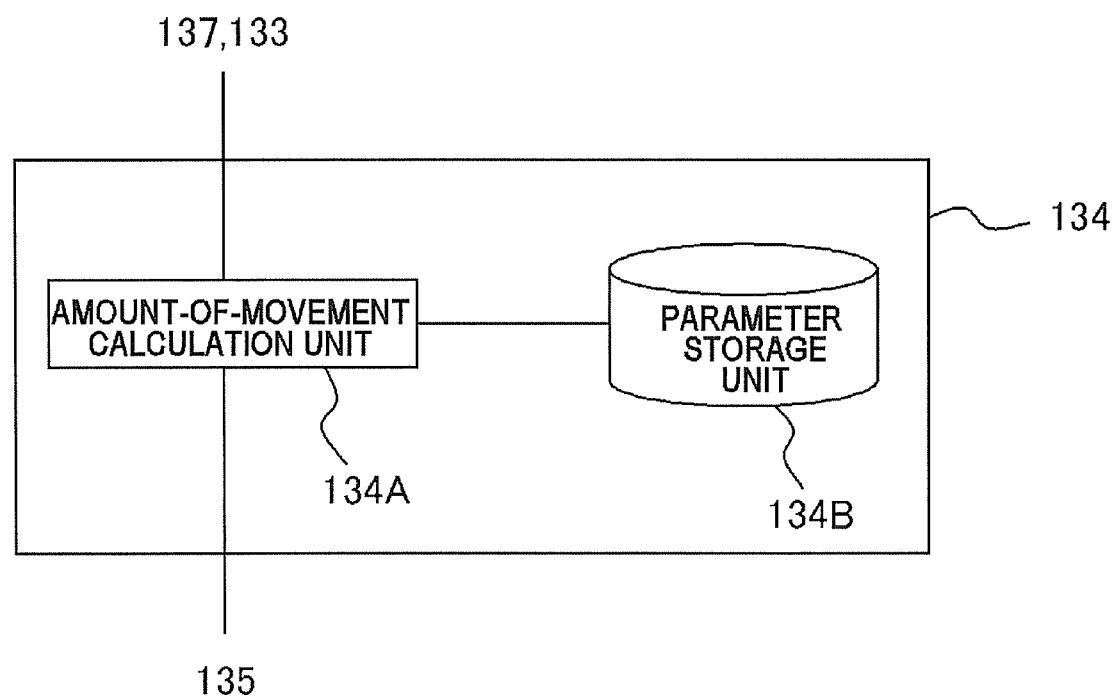
FIG. 34 is a block diagram showing a configuration of an amount-of-movement calculation unit of the measuring instrument of the fifth embodiment.

Next, the amount-of-movement calculation unit 134 will be explained referring to FIG. 34. The amount-of-movement calculation unit 134 calculates the amount of movement of water molecules, based on the water content calculated by the water content calculation unit 137, and the self-diffusion coefficient calculated by the mobility calculation unit 133.

The amount-of-movement calculation unit 134 has a parameter storage unit 134B having, stored therein, parameters used for calculating the amount of movement of water molecules, and an amount-of-movement calculation unit 134A calculating the amount of movement of water molecules by reading an equation for estimation out from the parameter storage unit 134B storing thereof.

The parameter storage unit 134B has, stored therein, the equation for estimation for calculating the amount of movement of water molecules, based on the self-diffusion coefficient and the water content, for every type of samples 115.

Based on the equation for estimation, the amount of movement may be calculated by amount-of-movement calculation unit 134A.

Next, the operations and effects of this embodiment will be explained.

In the measurement mode for measuring the water content, a target region to be measured is limited by using the small-sized RF coil 114 smaller in size than the sample 115, to thereby measure the water content at the specific position. Also in the measurement mode for measuring the self-diffusion coefficient, a target region to be measured is limited using the G coil 152A, the G coil 152B and the small-sized RF coil 114, to thereby measure the self-diffusion coefficient at the specific position where the water content was measured.

By obtaining the water content and the self-diffusion coefficient at the specific position of the sample 115, it becomes possible to exactly understand whether the fluctuation in the ion conductivity in the sample 115 is ascribable to the water content, or to the self-diffusion coefficient, or to both of the self-diffusion coefficient and the water content.

As a consequence, by monitoring the water content and the self-diffusion coefficient, the ion conductivity of the sample 115 may be kept constantly at a high level.

The water content and the self-diffusion coefficient can be measured at the same position of the sample 115, so that the amount of movement of local water molecules at the specific position of the sample 115 can exactly be understood, based on the water content and the self-diffusion coefficient.

In addition, measurement additionally made on a plurality of positions of the sample 115 using the measuring instrument 1 of the present invention helps understanding of distribution of the amount of movement of water molecules in the sample 115.

With the measuring instrument 1, measurement of the water content takes 1 second or around, and measurement of the self-diffusion coefficient takes 5 seconds or around. Assuming now the sample 115 as a solid polymer electrolyte film, changes in phenomena of the solid polymer electrolyte film are expressed over a duration of time several times or more as long as the measurement time required for the measuring instrument 1, that is, the measurement time is shorter than the time over which the changes in phenomena are expressed in the solid polymer electrolyte film, so that both of the water content and the self-diffusion coefficient can be understood before phenomena will change in the sample 115. It can, therefore, be said that the state of sample 115 when the water content is measured and the state of the sample 115 when the self-diffusion coefficient is measured are almost equal, so that ion conductivity of the sample 115 may exactly be understood, based on the water content and the self-diffusion coefficient.

The sensitivity range of the small-sized RF coil 114 is approximately as large as the inner diameter thereof. Application of the gradient magnetic field within this range allows measurement of the self-diffusion coefficient, so that it is good enough that the G coil 152A and the G coil 152B have a size only as large as capable of applying the gradient magnetic field within such range. Accordingly, also the G coil 152A and the G coil 152B can be downsized.

In addition, the water content calculation unit 137 of the measuring instrument 1 discriminates the NMR signals received by the data acceptance unit 131, and selects the NMR signals used for calculating the water content. Also the mobility calculation unit 133 discriminates the NMR signals received by the data acceptance unit 131, and selects the NMR signal used for calculating the self-diffusion coefficient. Because the NMR signals used for calculating the water content and the self-diffusion coefficient are discriminated in this way, exact water content and self-diffusion coefficient may be determined. Based on such exact water content and self-diffusion coefficient, the amount of movement of water molecules may exactly be calculated.

The small-sized RF coil 114 can be minimized in diameter to as small as several tens of micrometers, so that electric disturbance possibly exerted to the sample 115 side caused by provision of the small-sized RF coil 114 may be suppressed to a minimum level.

Sixth Embodiment

Figure 35:
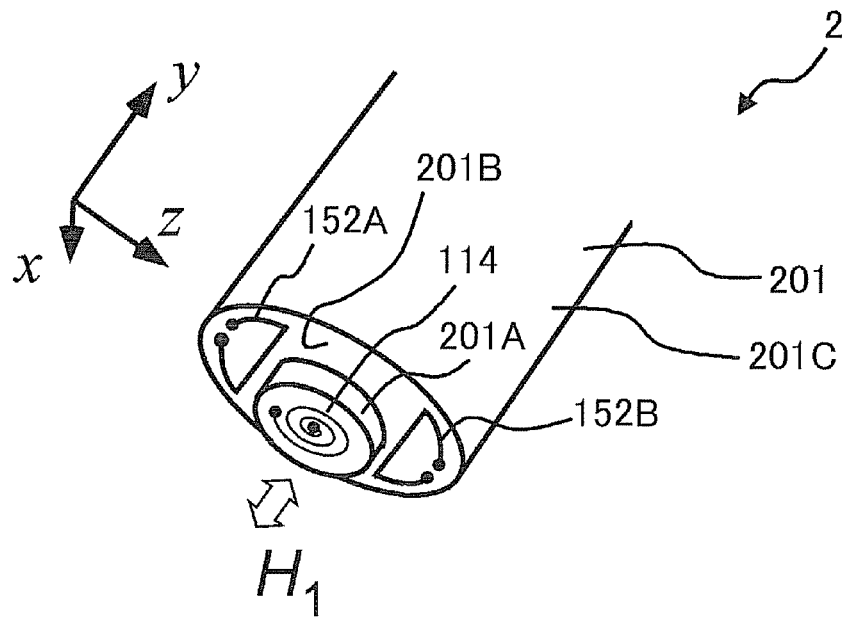
FIG. 35 is a schematic drawing showing an essential portion of the measuring instrument according to a sixth embodiment.
Figure 36:
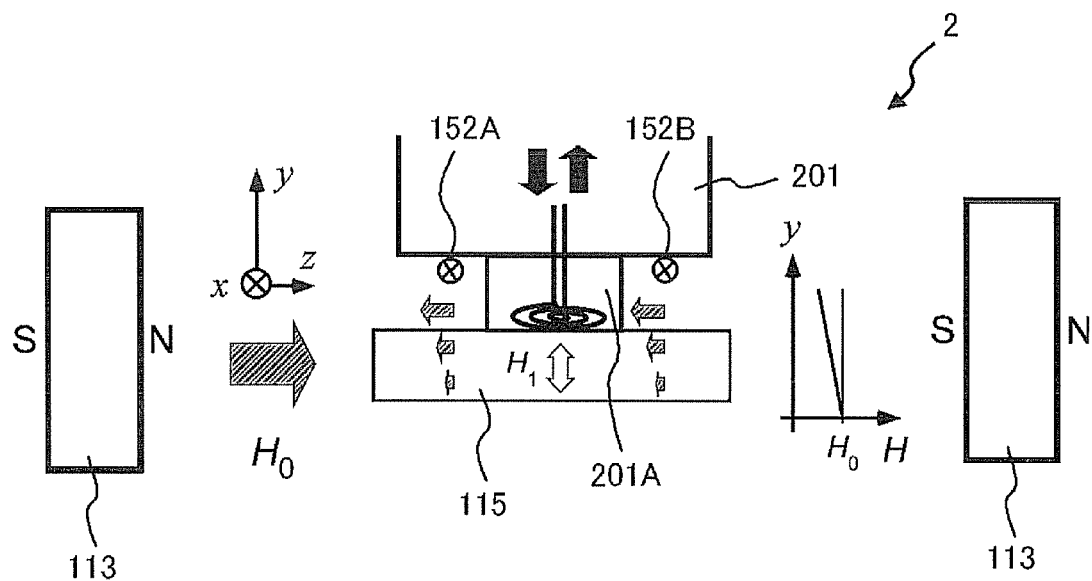
FIG. 36 is a schematic drawing showing an essential portion of the measuring instrument according to the sixth embodiment.

A measuring instrument 2 of this embodiment will be explained referring to FIGS. 35, 36.

In the measuring instrument 2 of this embodiment, the G coil 152A, the small-sized RF coil 114, and the G coil 152B are attached to the support 201. The other configurations are similar to those in the fifth embodiment.

The support 201 has a stick form, and has a cylindrical form in this embodiment. The support 201 has, on the end face 201B at the end portion 201C thereof, the G coil 152A, the small-sized RF coil 114, and the G coil 152B are attached. The G coil 152A and the G coil 152B are disposed while placing the small-sized RF coil 114 in between, and the small-sized RF coil 114 is projected towards the sample 115 side, out from the G coil 152A and the G coil 152B.

For more details, at the center of the end face 201B of the end portion 201C of the support 201, a columnar projection 201A projected towards the sample 115 side is provided, and on the end face of the projection 201A, a small-sized RF coil 114 is attached. The center of the plane of the small-sized RF coil 114 and the center axis of the support 201 almost coincide with each other.

On both side of the projection 201A as keeping it in between, the G coil 152A and the G coil 152B are respectively attached.

By disposing the G coil 152A and the G coil 152B on the upper side of the small-sized RF coil 114, it becomes possible to stably form the gradient magnetic field having a gradient in the direction of the y-axis, on the center axis of the small-sized RF coil 114.

By making the small-sized RF coil 114 project towards the sample 115 side out from the 152A and the coil 152B, only the small-sized RF coil 114 can be brought into contact with the sample 115 when the water content of the sample 115 is measured.

Lead wires (not shown) connected to the small-sized RF coil 114, lead wires (not shown) connected to the G coil 152A, and lead wires (not shown) connected to the G coil 152B are housed inside the support 201.

This embodiment exhibits effects below, in addition to those similar to as in the fifth embodiment.

The sensitivity range of the small-sized RF coil 114 is approximately as large as the inner diameter thereof. Application of the gradient magnetic field within this range will be sufficient for measurement of the mobility. It is, therefore, good enough that the G coils have a size only as large as capable of applying the gradient magnetic field within such range, so that the G coil 152A and the G coil 152B can be downsized. By downsizing also the G coil 152A and the G coil 152B, it becomes possible to integrate the small-sized RF coil 114, the G coil 152A, and the G coil 152B as being attached to the support, as shown in this embodiment. Accordingly, the G coil 152A, the G coil 152B, and the small-sized RF coil 114 become more readily be disposed with respect to the sample 115, and thereby the measuring instrument 2 will become more convenient to use.

The support 201 has a stick form, and thereby allows the user to carry out the measurement simply by holding the support 201 and to bring the end portion 201C thereof into contact with the sample 115, so that the operability of the measuring instrument 2 may be improved.

The lead wires connected to the small-sized RF coil 114 and the lead wires connected to the G coil 152A and the G coil 152B are disposed inside the support 201, so that the lead wires may be protected from physical external force. The lead wires may be protected also from electric disturbances such as noise.

By virtue of fixation by attachment of the small-sized RF coil 114, the ions of the coils 114, 152A, 152B, allowing the user to readily use the measuring instrument 2.

It is particularly difficult to oppose the G coil 152A and the G coil 152B, and thereby placing the small-sized RF coil 114 on a plane different from that for the G coil 152A and the G coil 152B, the following effects may be obtained:

(i) Uniform gradient magnetic field may be produced.

The small-sized RF coil 114, the G coil 152A and the G coil 152B are not in geometrically-ideal conditions in terms of diameter of wire, irregularity of winding and so forth. For this reason, placement of the small-sized RF coil 114, the G coil 152A and the G coil 152B on the same plane may inevitably cause a certain degree of non-uniformity in the gradient magnetic field. Placement of the small-sized RF coil 114 on the different plane from that for the G coil 152A and the G coil 152B may effectively reduce the non-uniformity in the gradient magnetic field ascribable to the non-ideal conditions of geometry described in the above.

(ii) Wire diameter of the G coil 152A and the G coil 152B may be increased.

Increase in the wire diameter generally tends to lower the uniformity in the gradient magnetic field, but adoption of the above-described configuration may solve this problem, allowing increase in the wire diameter. Increase in the wire diameter, capable of suppressing generation of Joule heat even under supply of large current, is effective for the case where larger gradient magnetic field is desired. If generation of Joule heat is suppressed, stability of application of the static magnetic field and the gradient magnetic field is improved, making the measurement convenient.

(iii) Too close placement of the G coil 152A and the G coil 152B with respect to the small-sized RF coil 114 may weaken the NMR signals received by the small-sized RF coil 114, due to shield effects of copper wires per se of the G coil 152A and the G coil 152B. This problem can be solved by placing the small-sized RF coil 114 on a plane different from that for the G coil 152A and the G coil 152B, as in this embodiment, so as to keep the small-sized RF coil 114 distant from the G coil 152A and the G coil 152B.

Seventh Embodiment

A measuring instrument 3 of this embodiment will be explained referring to FIGS. 37 to 39.

Figure 37:
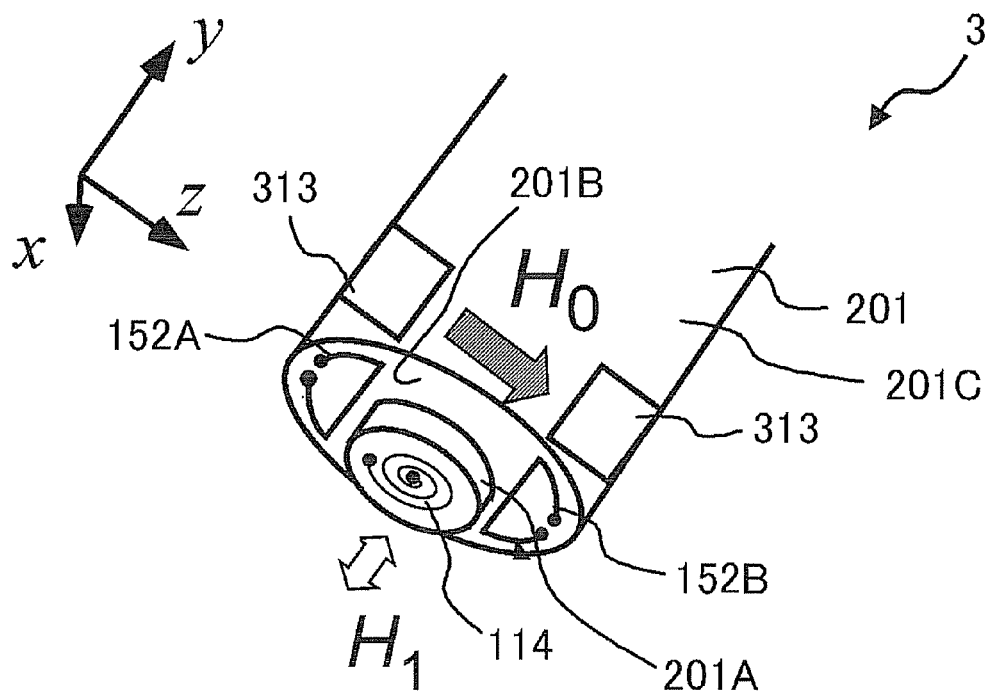
FIG. 37 is a schematic drawing showing an essential portion of the measuring instrument according to a seventh embodiment.
Figure 38:
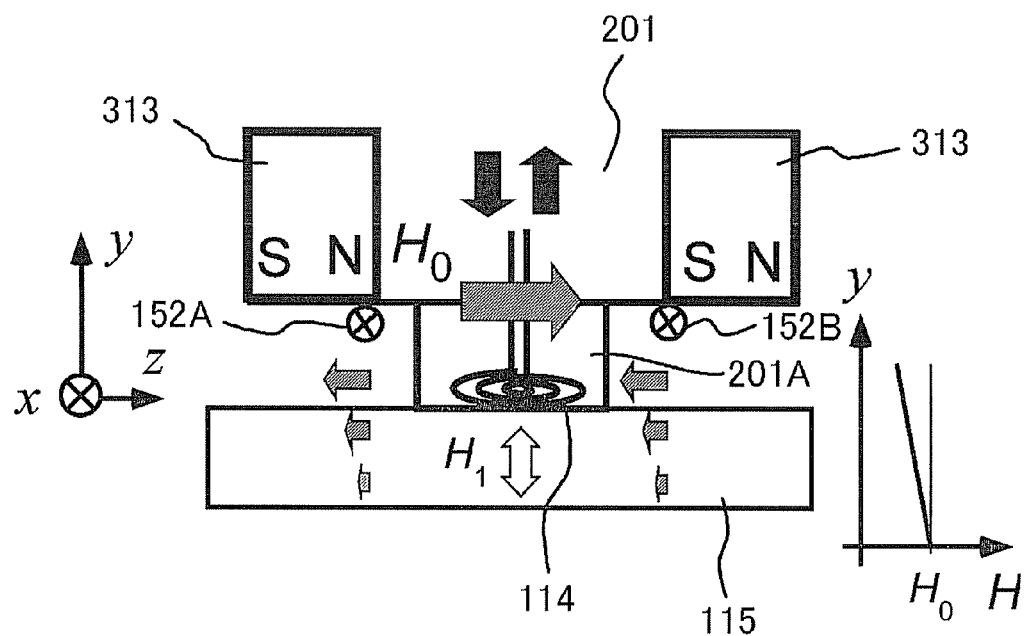
FIG. 38 is a schematic drawing showing an essential portion of the measuring instrument according to the seventh embodiment.

In the measuring instrument 3 of this embodiment, as shown in FIGS. 37, 38, support 201 has also a magnet 313 attached thereto, in addition to the small-sized RF coil 114, the G coil 152A, and the G coil 152B. Other configuration are similar to those in the sixth embodiment.

A pair of magnets 313 are smaller than the magnet 113 used in the measuring instruments 1, 2 in the fifth embodiment and the sixth embodiment. The measuring instruments 1, 2 of the individual embodiment described in the above were configured so that the magnets 113 apply the static magnetic field over the entire region of the sample 115, whereas in this embodiment, the magnets 313 are used to apply the static magnetic field at the specific position of the sample 115.

In this embodiment, a pair of magnets 313 are disposed inside the support 201, and fixed to the inner wall of the support 201. The pair of magnets 313 are disposed so as to place the small-sized RF coil 114 in between when viewed in the direction of the y-axis.

The static magnetic field $H_0$ produced by the pair of magnets 313 aligns normal to the center axis of the support 201. Because the static magnetic field $H_0$ aligns normal to the oscillating magnetic field for excitation $H_1$ produced by the small-sized RF coil 114, the NMR signals can be received by the small-sized RF coil 114.

The G coil 152A and the G coil 152B are disposed more closer to the sample 115 as compared with pair of magnets 313.

Figure 39:
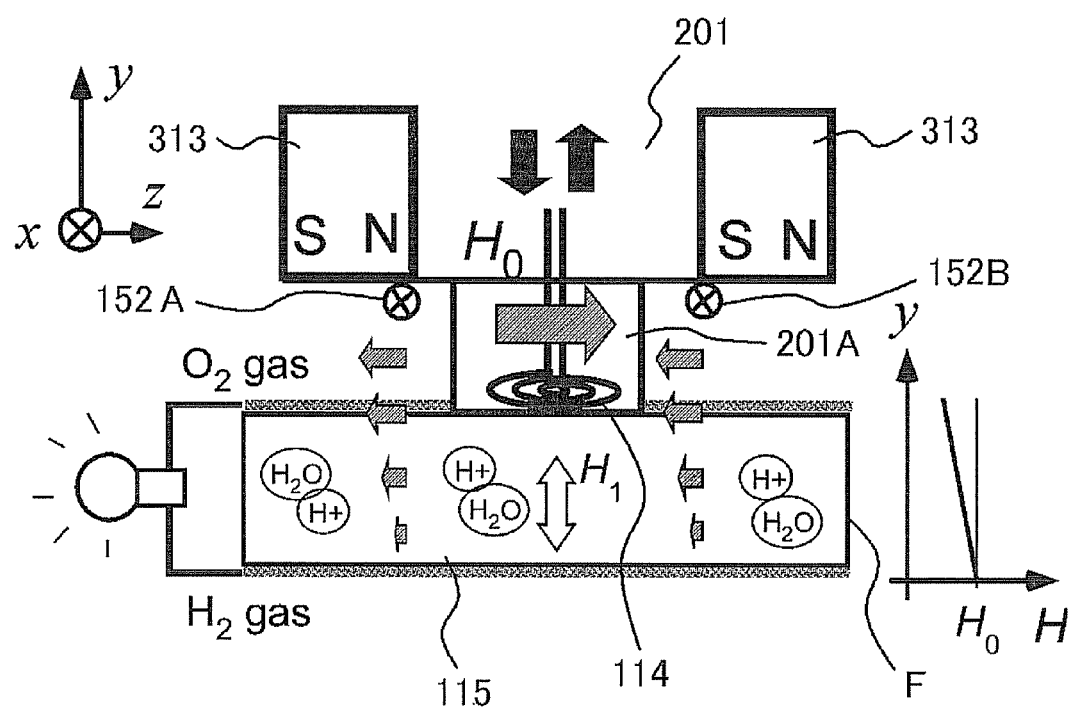
FIG. 39 is a schematic drawing showing an essential portion of the measuring instrument according to the seventh embodiment.

Using thus-configured measuring instrument 3, having the G coil 152A, the G coil 152B, the small-sized RF coil 114, and the magnets 313 attached to the support 201, the coils 114, 152A, 152B and the magnets 313 can readily be installed in a cell of a fuel cell F as shown in FIG. 39. As a consequence, mobility of water molecules through a solid polymer electrolyte film for fuel cells, as the sample 115 of the fuel cell F, can be measured while continuing power generation by the fuel cell F.

In addition, the gradient magnetic field is applied in the thickness-wise direction of the solid polymer electrolyte film for the fuel cell. Migration of water molecules in the thickness-wise direction is of particular importance in the solid polymer electrolyte film of fuel cells. By applying the gradient magnetic field while continuing power generation by the fuel cell, the mobility of water molecules in the thickness-wise direction of the solid polymer electrolyte film for fuel cells can be measured.

Figure 40:
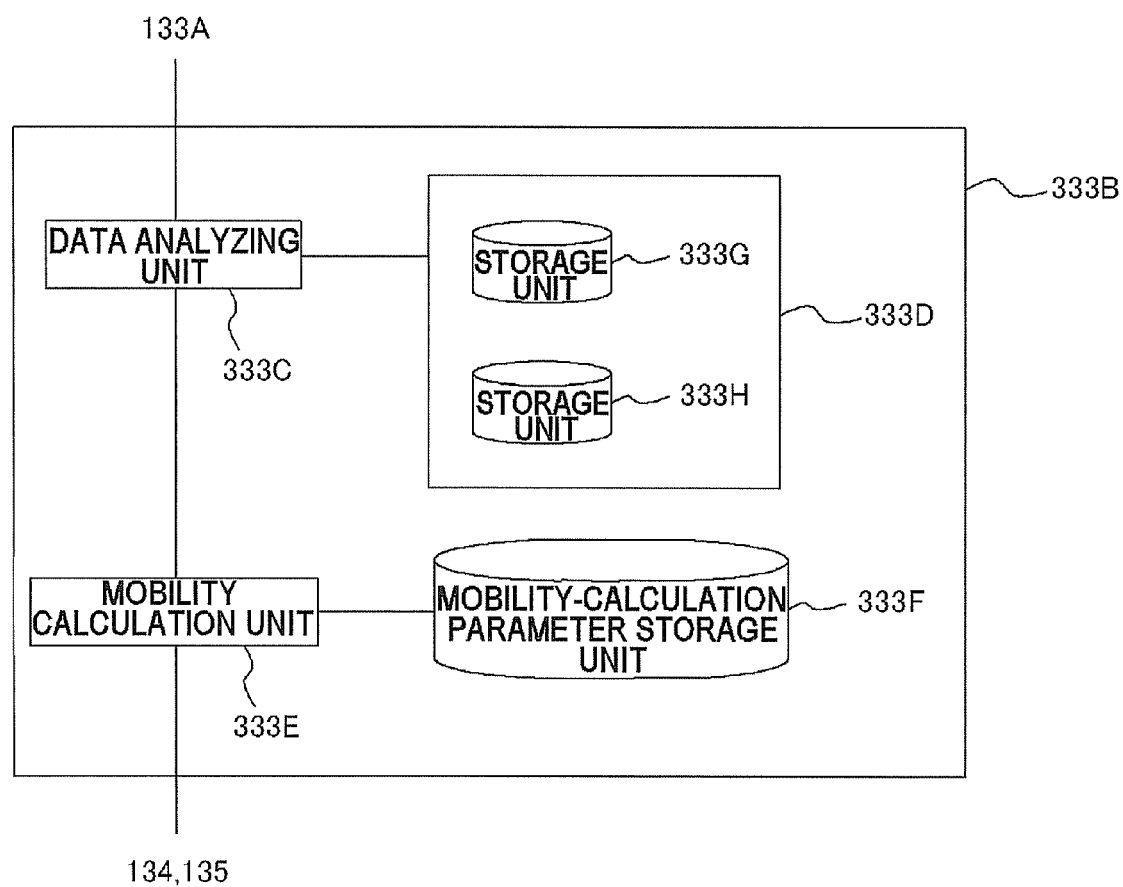
FIG. 40 is a block diagram showing a mobility calculation unit of the measuring instrument according to the seventh embodiment.

For understanding of the mobility in the sample 115, it is convenient to replace the configuration of the self-diffusion coefficient calculation unit 133B of the measuring instrument 1 shown in the fifth embodiment with a mobility calculation unit 333B shown in FIG. 40.

The mobility calculation unit 333B of this embodiment has a data analyzing unit 333C, a data storage unit 333D, a mobility calculation unit 333E, and a mobility-calculation parameter storage unit 333F.

A principle of calculating the mobility will now be explained.

Assuming now that there are two systems, consisting of (i) a system showing a phenomenon such that water molecules steadily moving therein in one direction, and (ii) a system showing no phenomenon like this. More specifically, (i) corresponds to the solid polymer electrolyte film during power generation by fuel cells, wherein hydrogen ions and electro-osmotic water move from the hydrogen electrode to the oxygen electrode. On the other hand, (ii) corresponds to the solid polymer electrolyte film of (i) when power generation is interrupted. They are different only in that the power generation is proceeded or interrupted.

First, with respect to (ii), difference between intensity of the NMR signals (amount of decrease in the NMR signals) obtained in the absence of the gradient magnetic field, and those obtained under application of the gradient magnetic field based on the PGSE method is detected.

Decrease in the intensity of the NMR signals herein depends on Brownian motion induced by thermal vibration.

On the other hand, also under the state of (i), difference between intensity of the NMR signals (amount of decrease in the NMR signals) obtained in the absence of the gradient magnetic field, and those obtained under application of the gradient magnetic field based on the PGSE method is detected.

Decrease in the NMR signals herein is ascribable to the total of "Brownian motion induced by thermal vibration" and "time-averaged unidirectional motion". During the power generation, hydrogen ions and electro-osmotic water always move from the hydrogen electrode to the oxygen electrode in an averaged manner, so that the "time-averaged unidirectional motion" never falls to zero.

Therefore, by calculating difference between the amount of decrease in intensity of the NMR signals in the state of (i) and the amount of decrease in intensity of the NMR signals in the state of (ii), "a degree of time-averaged unidirectional motion" can be calculated, and the mobility may be calculated based on the obtained value.

The data analyzing unit 333C of the mobility calculation unit 333B calculates the amount of decrease in the signals in the state of (i), based on the NMR signals received via the data discrimination unit 133A, and store them in the storage unit 333G of the data storage unit 333D.

On the other hand, the data analyzing unit 333C of the mobility calculation unit 333B calculates the amount of decrease in the signals in the state of (ii), based on the NMR signals received via the data discrimination unit 133A, and store them in the storage unit 333H of the data storage unit 333D.

The data analyzing unit 333C then calculates difference between the amount of decrease in the NMR signals in the state of (i) and the amount of decrease in the NMR signals in the state of (ii).

The mobility calculation unit 333E acquires the difference between the amount of decrease in the NMR signals in the state of (i) and the amount of decrease in the NMR signals in the state of (ii), and calculates the mobility, based on an equation for conversion stored in the mobility-calculation parameter storage unit 333F.

The data analyzing unit 333C, configured herein as calculating the amount of decrease in the signals in the state of (i), may be configured as calibrating the self-diffusion coefficient in the state of (i). In other words, the data analyzing unit 333C may be configured as a self-diffusion coefficient calculation unit. The self-diffusion coefficient in the state of (i) is stored in the storage unit 333G (self-diffusion coefficient storage unit) of the data storage unit 333D.

The data analyzing unit 333C calculates the self-diffusion coefficient in the state of (ii), and stores it in the storage unit 333H (self-diffusion coefficient storage unit) of the data storage unit 333D.

The data analyzing unit 333C then calculates difference between the self-diffusion coefficient in the state of (i), and the self-diffusion coefficient in the state of (ii). The mobility calculation unit 333E acquires the difference between the self-diffusion coefficient in the state of (i) and the self-diffusion coefficient in the state of (ii), and calculates the mobility based on an equation for conversion stored in the mobility-calculation parameter storage unit 333F.

The equation for conversion used for calculating the mobility based on the difference between the self-diffusion coefficient in the state of (i) and the self-diffusion coefficient in the state of (ii) can be derived as follows.

First, dry nitrogen is allowed to flow on one surface of a polymer electrolyte film, and nitrogen having a known concentration of water vapor is allowed to flow on the other surface. If a sufficiently steady state is established, the water vapor migrates through the film into the dry air. As a consequence, the dry air flows away while containing a certain amount of water vapor. A mean value (mv) of the amount of water readily passed through the film can be measured by measuring the water vapor concentration using a hygrometer. The film can be assumed as being uniform and having no distribution in the water migration, the mean value may be identical with a local value. The water content m is further calculated by the CPMG method. The "mobility v" may be calculated in this way.

Next, the difference between the self-diffusion coefficient in the polymer electrolyte film in the state of (i), and the self-diffusion coefficient in the state of (ii) is calculated. The difference between the self-diffusion coefficient in the state of (i) and the self-diffusion coefficient in the state of (ii) is then compared with the "mobility v". The equation for conversion can be prepared by carrying out the measurement under various conditions while varying difference in the water vapor concentration and state of dryness of the film.

This method of deriving the equation for conversion is merely one example, allowing any other methods of deriving the equation of conversion.

It is also allowable to prepare an equation for conversion for each type of the samples 115, and store them in the mobility-calculation parameter storage unit 333F.

According to this embodiment, in addition to the effects similar to those in the fifth embodiment and the sixth embodiment, the effects below will be obtained.

The measuring instrument 3, having small-sized magnets 313 for applying the static magnetic field $H_0$ is attached to the support 201, so that any large magnet 113 is no more necessary, successfully downsizing the measuring instrument 3.

Moreover, integration of the magnets with the small-sized RF coil 114, the G coil 152A, and the G coil 152B as shown in this embodiment, these coils 114, 152A, 15213 and the magnets 313 may readily be installed in the fuel cell F as shown in FIG. 39. Accordingly, it becomes possible to readily understand the water content and mobility of water molecules of the solid polymer electrolyte film for fuel cells, and the amount of movement of water molecules, during power generation by the fuel cell F.

As described previously, power generation efficiency of fuel cells strongly depends on the ion conductivity of the solid polymer electrolyte film, so that this configuration helps understanding of fluctuation in the ion conductivity, and further in the power generation of fuel cells, by understanding the water content, mobility of water molecules and the amount of movement of water molecules in the solid polymer electrolyte film.

By measuring the water content, the mobility of water molecules and the amount of movement of water molecules at a plurality of positions of the solid polymer electrolyte film using the measuring instrument 3 of this embodiment, during power generation by the fuel cell, distributions of the water content, mobility and amount of movement in the solid polymer electrolyte film during power generation may be understood. Based on thus-understood distributions of water content and so forth, it also becomes possible, during power generation, to control supply of water to the solid polymer electrolyte film of fuel cells, and to prevent fluctuation in the amount of power generation.

In this embodiment, the small-sized RF coil 114 is attached to the projection 201A of the support 201, as being projected to the sample 115 side out from the G coils 152A, 15213. Therefore, only the small-sized RF coil 114 may be brought into contact with the sample 115. For the case where the sample 115 is a solid polymer electrolyte film for fuel cells, this configuration can minimize the area which may interfere supply of gas to the solid polymer electrolyte film during the measurement.

In this embodiment, the small magnets 313 for applying the static magnetic field $H_0$ are attached to the support 201. In order to exactly understand the amount and the self-diffusion coefficient of a protic solvent in a sample, based on the nuclear magnetic resonance method, it is important to match the resonance frequency of magnetization of a target nucleus to be measured with RF pulse frequency.

For the case where the position of the magnet is not adjustable with respect to the sample 115, it is necessary to sweep the basic frequency of the RF oscillator in accordance with the resonance frequency of the target nucleus to be measured, so as to adjust impedance of the small-sized RF coil.

On the contrary, in this embodiment, the sample 115 and the magnets 313 are readily adjustable in the distance therebetween, since the magnets 313 are attached to the support 201, and thereby intensity of the static magnetic field applied to the sample 115 may readily be adjustable. As the intensity of the static magnetic field varies, also the resonance frequency of nuclear magnetization varies. Therefore, in this embodiment, a position where the resonance frequency of nuclear magnetization will coincide with a resonance frequency coresponded to the frequency of RF pulses irradiated from the small-sized RF coil 114 can be found out, by adjusting the position of the support relative to the sample 115.

As a consequence, it is no more necessary to sweep the basic frequency of the RF oscillator, nor to adjust the impedance of the small-sized RF coil, and thereby the content, the self-diffusion coefficient or the like of a protic solvent in a sample may be understood in an exact and simple manner.

Eighth Embodiment

Figure 41:
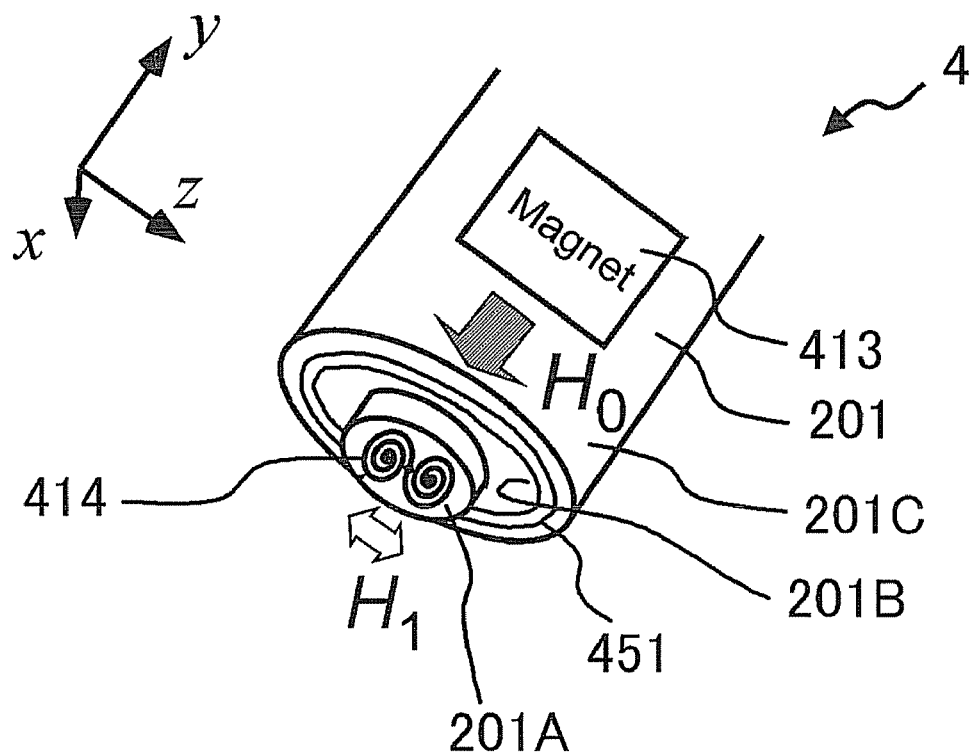
FIG. 41 is a schematic drawing showing an essential portion of the measuring instrument according to an eighth embodiment.
Figure 42:
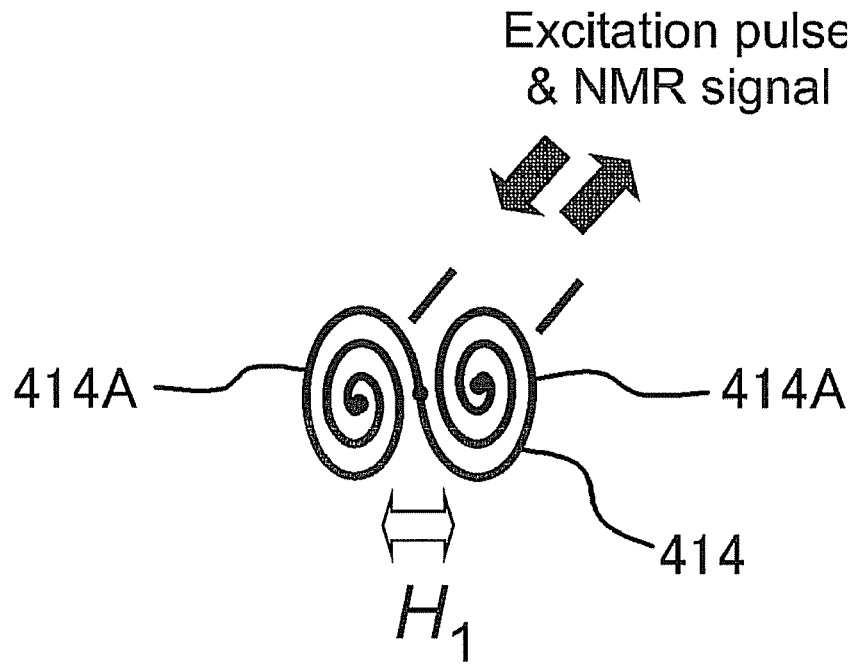
FIG. 42 is a schematic drawing showing the small-sized RF coil according to the eighth embodiment.
Figure 43:
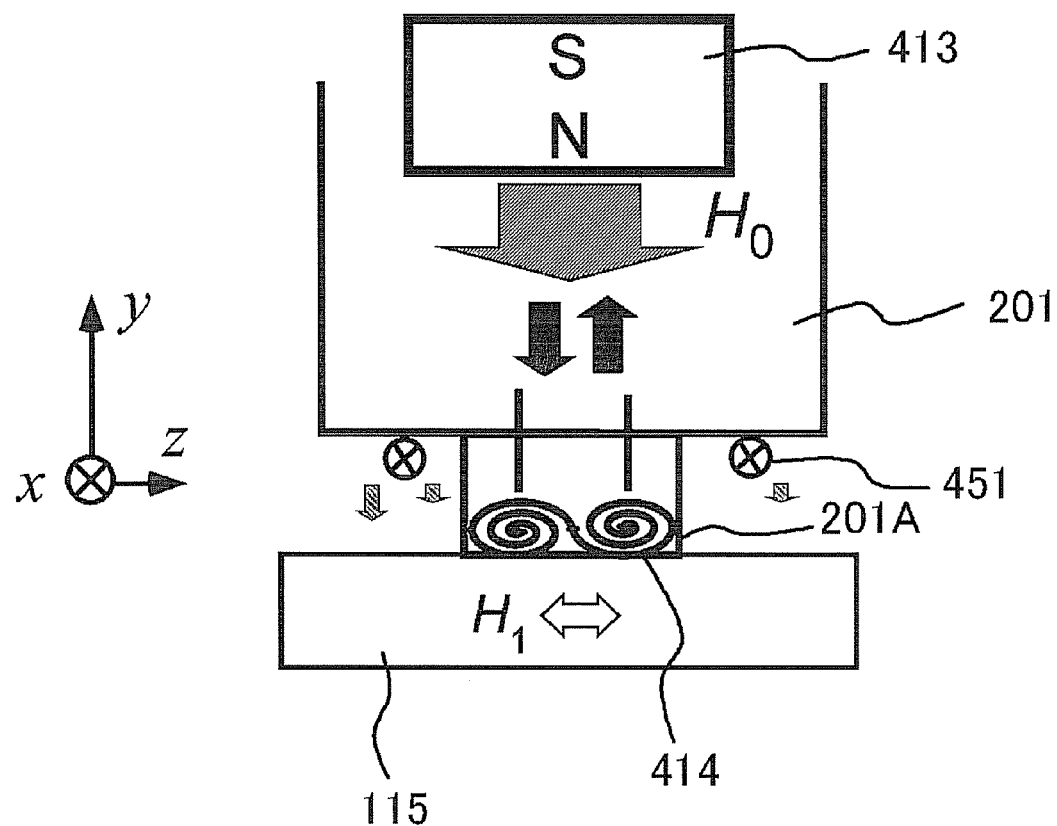
FIG. 43 is a schematic drawing showing an essential portion of the measuring instrument according to the eighth embodiment.

An eighth embodiment will be explained referring to FIG. 41 to FIG. 43.

In the seventh embodiment, the static magnetic field $H_0$ was generated normal to the center axis of the support 201, whereas a measuring instrument 4 of this embodiment disposes a magnet 312 so that the static magnetic field $H_0$ aligns with the center axis of the support 201. In this case, the oscillating magnetic field for excitation $H_1$ is necessarily applied normal to the center axis of the support 201, so that so-called "figure-8" or "butterfly" small-sized RF coil 414 having two spiral coil portions 414A linked with each other, as shown in FIG. 42, is used. As shown in FIGS. 41, 43, the direction of the static magnetic field $H_0$ and the direction of the oscillating magnetic field for excitation $H_1$ generated by the small-sized RF coil 414 are normal to each other, so as to receive the NMR signals.

In this embodiment, a spiral coil is used as a G coil 451. The G coil 451 is disposed so as to surround the small-sized RF coil 414.

Ninth Embodiment

Figure 44:
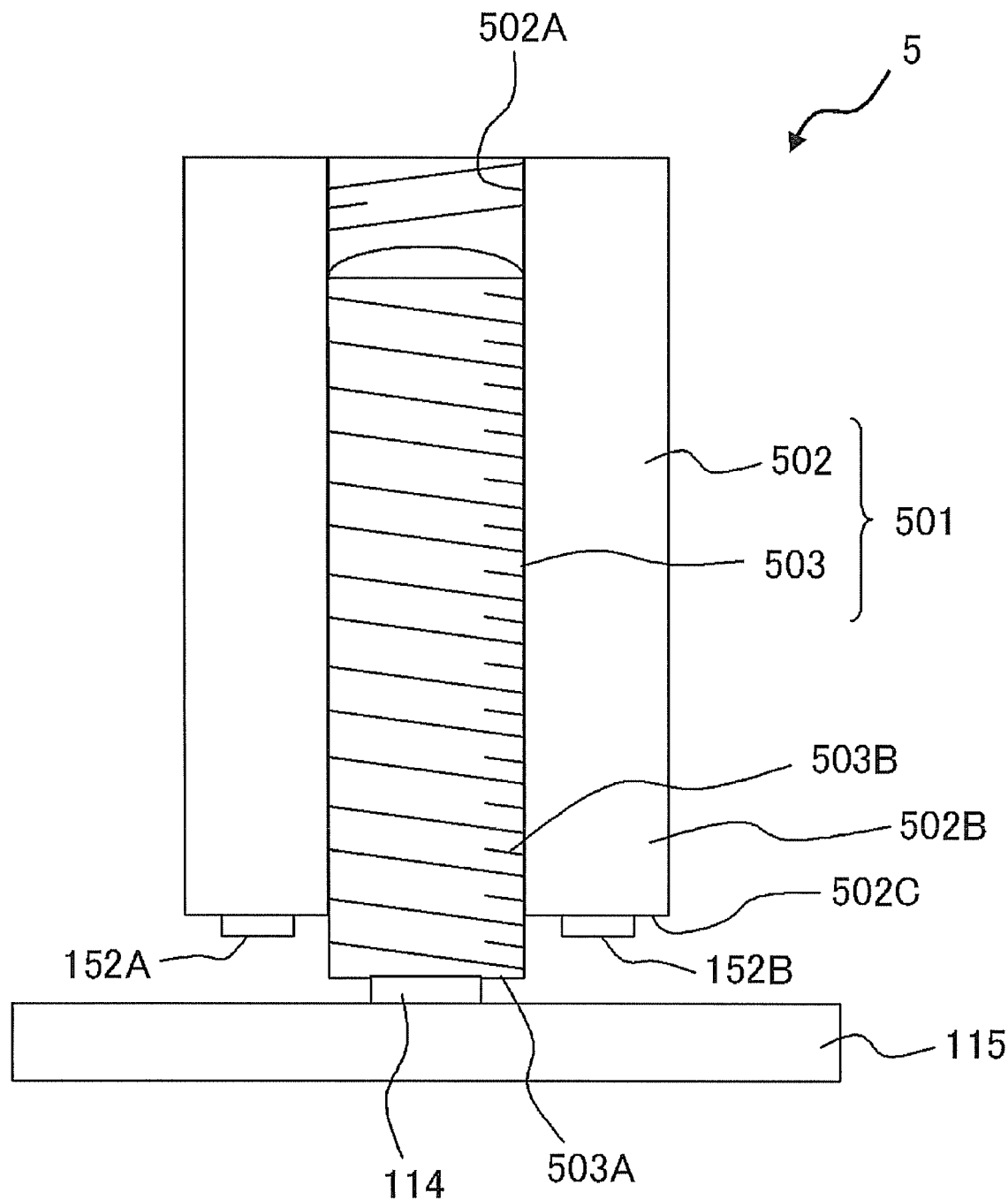
FIG. 44 is a schematic drawing showing an essential portion of the measuring instrument according to a ninth embodiment.

This embodiment will be explained referring to FIG. 44.

In the previous fifth to eighth embodiments, relative position of the G coil(s) and the small-sized RF coil were fixed, whereas in a measuring instrument 5 of this embodiment, relative position of the G coil and the small-sized RF coil, and further relative position of the magnet 313 and the small-sized RF coil are adjustable. Except that the relative position of the G coil and the small-sized RF coil, and the relative position of the magnet 313 and the small-sized RF coil are adjustable, this embodiment is configured similarly to the third embodiment.

The measuring instrument 5 has a support 501, where the support 501 has a near-columnar main unit 502 having a through-hole 501A formed along the center axis thereof, and a rod-like moving component 503 movable back and forth in the main unit 502.

At around the center of both end faces of the main unit 502 along the longitudinal direction thereof, openings of the through-hole are formed. The inner face of the through-hole 502A has a female thread cut thereon. On the end face 502C of the end portion 502B of the main unit 502, the G coil 152A and the G coil 152B are disposed while placing the opening of the through-hole 502A in between.

Although not shown, the main unit 502 further has a pair of magnets 313, similar to those in the third embodiment, fixed on the inner wall thereof.

The moving component 503 is near-cylindrical, and has end faces disposed normal to the longitudinal direction thereof, wherein on one end face 503A on the end portion 503B, the small-sized RF coil 114 is attached. The moving component 503 has a thread cut on the outer circumference thereof, thereby the moving component 503 can engage with the female thread on the inner surface of the through-hole 502A of the main unit 502. Therefore, relative position of the G coils 152A, 152B and the small-sized RF coil 114, and further relative position of the magnet 313 and the small-sized RF coil, are adjustable by rotating the moving component 503. In addition, also positions of the small-sized RF coil 114 and the sample 115, and further positions of the G coils 152A, 152B and the sample 115 are adjustable. For example in the measuring instrument 5, when the small-sized RF coil 114 is brought into contact with the surface of the sample 115 so as to measure the water content and so forth, the positions of the G coils 152A, 152B fixed on the end face 502C of the main unit 502 and the sample 115 are adjustable, by rotating the moving component 503, to thereby adjust the range of projection of the small-sized RF coil 114 out from the end portion 502B of the main unit 502.

As a consequence, this configuration provides an adjusting mechanism based on the combination of the moving component 503 and the main unit 502, which is capable of adjusting positions of the G coils 152A, 152B and the sample 115, and the relative position of the magnet 313 and the small-sized RF coil.

For the case where the water content or the like is measured without bringing the small-sized RF coil 114 into contact with the sample 115, it is also allowable to adjust the distance between the small-sized RF coil 114 and the sample 115 by rotating the moving component 503, to thereby adjust the range of projection of the small-sized RF coil 114 from the main unit 502.

This embodiment not only expresses the effects same as those in the fifth embodiment to the eighth embodiment, but also expresses the effects below.

Because the small-sized RF coil 114 can be projected out from the end face 502C of the main unit by rotating the moving component 503, the small-sized RF coil 114 may exactly be brought into contact with the sample while being adjusted in the range of projection thereof.

Adjustment of the range of projection of the small-sized RF coil 114 out from the end face 502C of the main unit 502, by rotating the moving component 503, causes positional changes of the G coils 152A, 152B with respect to the sample 115. Accordingly, intensity of the gradient magnetic field applied to the sample may be varied.

Intensity of the static magnetic field applied by the magnet 113 fixed on the inner wall of the main unit 502 attenuates as the distance from the magnet 313 increases. When intensity of the static magnetic field is desired to vary, it is convenient to drive the moving component 503 to thereby move the small-sized RF coil 114 to a position where a desired intensity of static magnetic field is obtained. This configuration can get rid of an adjusting function of resonance frequency using an LC circuit which has been necessary for general small-sized RF coil 114, and instead allows detection of the NMR signals using a simple-structured, fixed-resonance-frequency LC circuit composed of fixed capacitors. Therefore, the function of adjusting the LC circuit may be omissible, by searching a point of static magnetic field which coincides with the resonance frequency of the small-sized RF coil 114.

Tenth Embodiment

Figure 45:
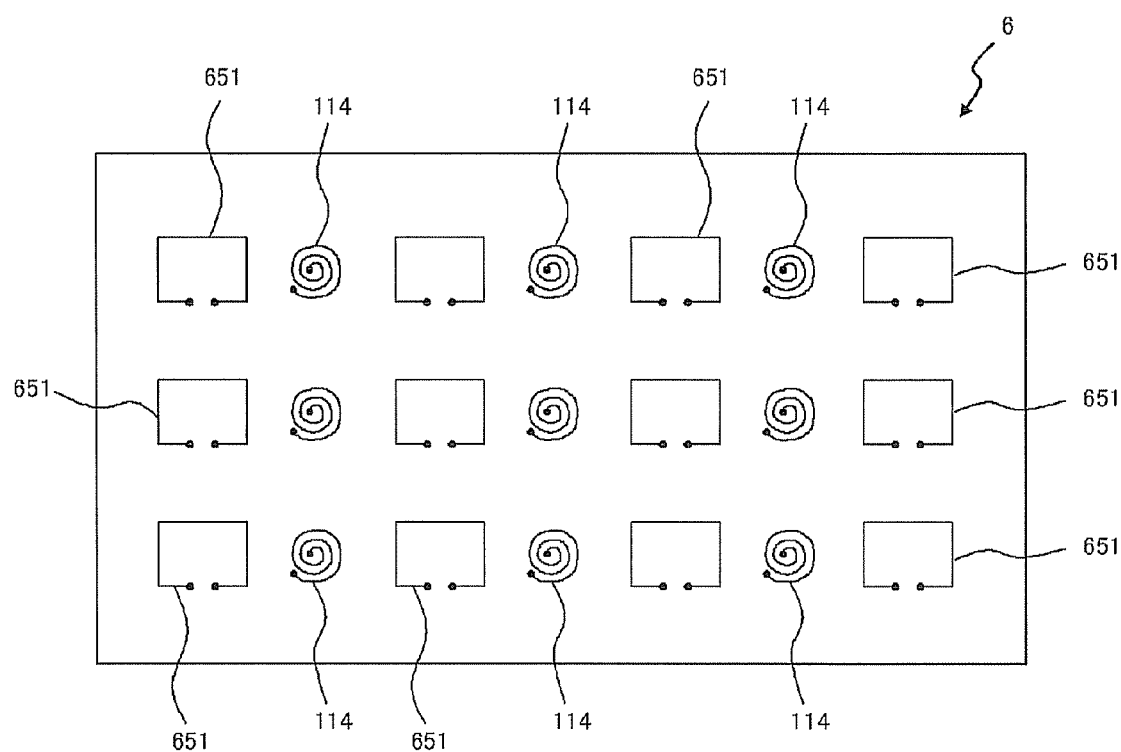
FIG. 45 is a drawing showing an arrangement of the G coil and the small-sized RF coil in the measuring instrument of a tenth embodiment.
Figure 46:
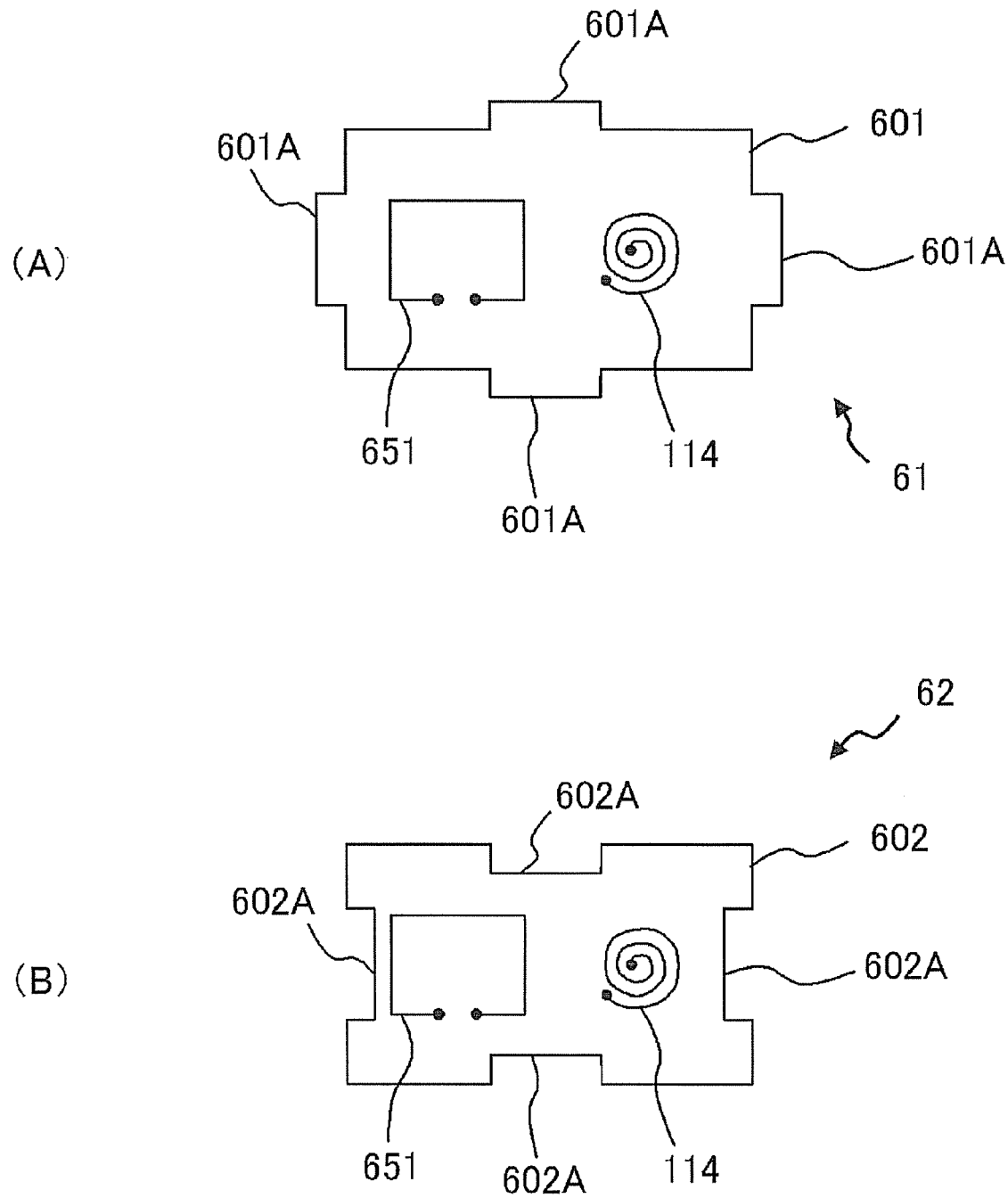
FIGS. 46(A) and (B) are plan views of a unit according to the tenth embodiment.

This embodiment will be explained referring to FIGS. 45, 46.

In the previous fifth to ninth embodiments, the measuring instruments 1 to 5 were configured as having a single small-sized RF coil 114, whereas a measuring instrument 6 of this embodiment has a plurality of small-sized RF coils 114 and a plurality of G coils 651. In this embodiment, a gradient magnetic field application unit is configured as having a plurality of G coils 651. Other configurations are same as those in the fifth embodiment.

The G coils 651 used in this embodiment are planar coils having a plane geometry of square frame.

Thus-formed G coils 651 and the small-sized RF coils 114 are arrayed on the same plane. More specifically, the G coils 651 and the small-sized RF coils 114 are alternately arranged, wherein each small-sized RF coil 114 is arranged as being kept between a pair of G coils 651.

In order to arrange the G coils 651 and the small-sized RF coils 114 in array, supports 601, 602 having plane geometries shown in FIGS. 46(A), (B) may be used. The support 601 is a planar substrate, having projections 601A (coupling tabs) as being swelled out from the individual edges of the planar rectangular geometry thereof. On the surface of thus-configured support 601, a single G coil 651 and a single small-sized RF coil 114 are attached, composing a single unit 61.

Also the support 602 is composed of a planar substrate, having notches 602A formed by inwardly notching a part of each edge of the substrate having a planar rectangular geometry. The notch 602A has a geometry allowing the projection 601A engaged therein. Also on the surface of the support 602, a single G coil 651 and a single small-sized RF coil 114 are attached, composing a single unit 62.

By engaging the projection 601A of the support 601 with the notch 602A of the support 602, the G coils 651 and the small-sized RF coils 114 may be arranged in array.

The geometry of the projections 601A (coupling tabs), given as a planar rectangular geometry in this embodiment, may also be such as being outwardly widened in width. This geometry allows stable engagement between the projections 601A and the notches 602A.

This embodiment not only expresses the effects same as those in the fifth embodiment, but also expresses the effects below.

By alternately disposing the small-sized RF coils 114 and the G coils 651 as in this embodiment, the G coils 651 placed between pairs of small-sized RF coils 114 can apply the gradient magnetic field to pairs of small-sized RF coil 114.

Because a single G coil 651 may be used for applying the gradient magnetic field to a single pair of small-sized RF coils 114, the space may more effectively be saved as compared with the second embodiment where a plurality of sets, each having a pair of G coils and a small-sized RF coil kept therebetween, are arranged.

The arrangement of the plurality of small-sized RF coils 114 and G coils 651 in array allows understanding of the water content and the self-diffusion coefficient of water at a plurality of specific positions of the sample 115 at the same time, and thereby distributions of the water content, self-diffusion coefficient and so forth of the sample 115 may be detected.

Because the G coils 651 are disposed in adjacent to the individual small-sized RF coils 114, the G coils 651 can now apply stronger gradient magnetic field to the specific positions of the sample 115, as compared with the case where a plurality of small-sized RF coil are disposed between a pair of G coils, without needing large electric power.

In this embodiment, the small-sized RF coils 114 and the G coils 651 are supported on the planar supports 601, 602, so that the water content or the like of the sample 115 may be measured simply by setting the supports 601, 602 as being placed on the sample 115.

Because the projections 601A of the support 601 may be engaged with the notches 602A of the support 602, the G coils 651 and the small-sized RF coils 114 may readily be arrayed.

In this embodiment, the G coils 651 are disposed in adjacent to the individual small-sized RF coils 114. For the case where a plurality of small-sized RF coils 114 are used, a possible method herein may be such as using a single pair of large G coils so as to keep a plurality of small-sized RF coil 114 in between, to thereby apply the gradient magnetic field.

In this case, the gradient magnetic field grows larger at positions more distant from the center. In measurement based on the PGSE method using large G coils, in other words, when distributions of a pair of positive/negative magnetic fields having a constant gradient are formed by supplying a pair of positive/negative pulses to the gradient magnetic field coil, it is necessary to produce the magnetic fields having large gradient magnetic field values directly inverted between positive and negative. It is, however, more difficult to ensure symmetry of the positive and negative values, at positions where these values become larger (positions more distant from the center), wherein the degradation in symmetry of the gradient magnetic field values may degrade accuracy of the measurement.

In contrast, by disposing the G coils 651 adjacent to the individual small-sized RF coils 114 as in this embodiment, the gradient magnetic field values will not grow larger since the configuration uses only a portion of the magnetic field gradient, at around the center between a pair of G coils 651, thereby the degradation in symmetry of the gradient magnetic fields may be reduced. As a consequence, accuracy in the measurement of the water content, the self-diffusion coefficient and so forth may be improved.

The embodiments of the present invention have been described in the above referring to the drawings, wherein these embodiments are merely examples of the present invention, allowing adoption of various configurations other than those described in the above.

For example, the sample 115, exemplified in the foregoing embodiments as a solid polymer electrolyte film used for fuel cells, is not limited thereto, and may be fruits, vegetables and so forth. Based on the self-diffusion coefficient and water content of fruits and vegetables, the sugar contents thereof may be calculated. It becomes also possible to understand process of growth of fruits, vegetables and so forth, based on their self-diffusion coefficient and water content.

It is also allowable to detect state of fermentation, by understanding the self-diffusion coefficient and water content of cheese and so forth.

The measuring instrument of the present invention may be applicable also to inspection of foods, because it allows understanding of conditions of samples without destroying the samples.

The measuring instruments disclosed in the foregoing individual embodiments may be applied to medical purposes. Cancer or the like may be detected by bringing the small-sized RF coil to a diseased site, and thereby understanding the self-diffusion coefficient and the water content.

Although the self-diffusion coefficient of water molecules contained in the solid matrix, and the water content were measured in the foregoing individual embodiments, the present invention is widely applicable to measurement of mobility of protic solvent and the content of protic solvent.

Although the oscillating magnetic field for excitation in the foregoing individual embodiments was applied in a form of pulse sequence of excitation-use high-frequency pulse, any other modes of embodiment may be adoptable so far as they allows acquisition of the NMR signals. The NMR signals are specifically free induction decay signals induced by the oscillating magnetic field for excitation; and
echo signals such as spin-echo signal, gradient echo signal and so forth.

Although the measuring instruments in the foregoing individual embodiments were configured as having the switching unit 161 at a branching portion where the small-sized RF coil 114, the RF excitation pulse generating unit (or RF signal generating unit) and the NMR signal detecting unit are connected, the switching unit 161 may be omissible. Omission of the switching unit may simplify the configuration of the instrument.

The measuring instruments 1 to 6 in the fifth embodiment to the tenth embodiment, configured as allowing the measurement mode selecting unit to select either of two measurement modes, that are the measurement mode allowing measurement of water content, and the measurement mode allowing measurement of mobility of water molecules, may be configured also as selecting three or more measurement modes.

Although in the fifth embodiment to the tenth embodiment, the NMR signals were discriminated based on intensity of the received signals by the data discrimination unit 132A and the data discrimination unit 133A, method of discriminating the NMR signal are not limited thereto. For example, it is also allowable to calculate a time-differential value of deviation of intensity of received plurality of NMR signals, and to discriminate the NMR signals based on the time-differential value.

In the foregoing individual embodiments, the water content calculation unit 137 was configured as having the correction unit 132F correcting the estimated value of water content in a manner adaptive to the size of the small-sized RF coil 114, and also the mobility calculation unit 133 was configured as having the correction unit 133F correcting the estimated value of self-diffusion coefficient in a manner adaptive to the size of the small-sized RF coil 114, whereas another possible configuration is such that only either one of the water content calculation unit and the mobility calculation unit has the correction unit.

Still another possible configuration is such that both of the water content calculation unit and the mobility calculation unit do not have the correction unit.

Geometry of the stick-like supports 201, 501, which was columnar in the foregoing sixth embodiment to the ninth embodiment, is not limited thereto. For example, the support may have a geometry kinked as figure L.

Arrangement of the G coils 152A, 152B, 451 and the small-sized RF coils 114, 414, disposed on different planes in the sixth embodiment to the eighth embodiment, is not limited thereto, allowing arrangement of the G coils and the small-sized RF coils disposed on the same plane. For example, the G coils and the small-sized RF coils may be fixed on the end face of the columnar support. Arrangement of the small-sized RF coils and the G coils on the same plane allows formation of the small-sized RF coils and the G coils in the same process step.

Although in the ninth embodiment, the threads were cut on the inner surface of the through-hole 502A of the main unit 502 and on the outer surface of the moving component 503, so as to allow adjustment of the relative position of the G coils 152A, 152B and the small-sized RF coil 114 by rotating the moving component 503, wherein the moving component may be driven by a piezoelectric element. Drive of the moving component using the piezoelectric element allows fine adjustment of the relative position between the small-sized RF coil and the G coils.

Although units each having a single G coil 651 and a single small-sized RF coil 114 were arranged in the tenth embodiment, units each having two or more G coils and small-sized RF coils alternately disposed therein may be arranged.

Although the small-sized RF coils 114 and the G coils 651 were alternately disposed in the tenth embodiment, the arrangement is not limited thereto, instead allowing an arrangement such that a plurality of small-sized RF coils are disposed between a pair of G coils. This way of arrangement may reduce the number of use of G coils, and may thereby reduce the cost for the measuring instrument.

In the tenth embodiment, the measuring instrument may be configured so that the relative position between the small-sized RF coil 114 and the G coils 651 may be adjustable.

The sixth embodiment to the ninth embodiment, having been exemplified as other modes of embodiment of the measuring instrument shown in the fifth embodiment, are not limited thereto, and may be adoptable to the measuring instruments of the first embodiment, the second embodiment and the third embodiment. More specifically, on the end face of the stick-like support, the G coils 151, 153 (155, 157) and the small-sized RF coil 114 may be fixed. Further the magnet 313 may be attached to this support.

The tenth embodiment, having been exemplified as other modes of embodiment of the measuring instrument shown in the fifth embodiment, are not limited thereto, and may be adoptable to the measuring instruments of the first embodiment, the second embodiment and the third embodiment. More specifically, the measuring instruments of the first embodiment, the second embodiment and the third embodiment are configured as having a plurality of small-sized RF coils and G coils, wherein the G coils and the small-sized RF coils may alternately be disposed. In the tenth embodiment, the G coils and the small-sized RF coils may alternately be disposed, further by forming a unit composed of a small-sized RF coil and a G coil, and by disposing a plurality of units.

The measuring instruments in the foregoing individual embodiments, configured as having the sample stage 116, are not limited thereto, allowing omission of the sample stage 116. If the sample 115 is a constituent of a certain product, mobility of protic solvent or the like of the constituent can locally be calculated, by disposing the small-sized RF coil 114 in the product.

In the foregoing individual embodiments, the (a) 90° pulse and the (b) 180° pulse may have the same phase, or different phases. For the case of difference, they may shift by 90° from each other as described previously.

The foregoing individual embodiments explained the cases where the gradient magnetic field was applied to the sample 115 using a pair of, or more G coils, wherein the mode of inclination of the magnetic field is not specifically limited, typically allowing that a single G coil is disposed at a predetermined position with respect to the sample 115, so as to form the gradient magnetic field. More specifically, a single annular G coil applying the gradient magnetic field in the z-direction may be provided.

Although mobility of protic solvent in the sample 115 was not measured in the foregoing first to the sixth embodiment, and the eighth embodiment to the tenth embodiment, the mobility of protic solvent may be measured. Measurement of the mobility may be proceeded based on the principle described in the seventh embodiment. That is, also in the first embodiment to the sixth embodiment, and the eighth embodiment to the tenth embodiment, the measuring instruments may be configured as having the mobility calculation unit 333B shown in FIG. 40 so as to allow calculation of mobility.

More specifically, in the measuring instruments of the first embodiment to the fourth embodiment, it is convenient to configure the operation unit 130 as having a self-diffusion coefficient calculation unit (corresponded to the data analyzing unit 333C in FIG. 40) calculating the self-diffusion coefficient obtained under a phenomenon showing a protic solvent in a sample steadily moving in one direction, and the self-diffusion coefficient obtained under a phenomenon showing a protic solvent in a sample not steadily moving in one direction, a self-diffusion coefficient storage unit (corresponded to the storage unit 333G, and the storage unit 333H in FIG. 40) storing the self-diffusion coefficients calculated by the self-diffusion coefficient calculation unit, and a mobility calculation unit 333E calculating the mobility, based on difference between the self-diffusion coefficients stored in the self-diffusion coefficient storage unit.

EXAMPLES

Example 1

In this example, the self-diffusion coefficient was measured based on the PGSE method, using the instrument (FIG. 19) described in the second embodiment.

The small-sized RF coil 114 shown in FIG. 19 was manufactured by winding a 50-μm-diameter copper wire by 3.5 turns, with an outer diameter of 2.0 mm. In this Example, two coils were used, each of which placed on the same sample. In the explanation below, one channel connected to one of two small-sized RF coils 114 will be referred to as a first channel, and the other as a second channel.

A dilute aqueous copper sulfate solution was used as the sample. A through-hole (15 mm×15 mm) was formed at the center of a 0.5-mm-thick acryl plate (18 mm×18 mm), and 0.12-mm-thick cover glasses (18 mm×18 mm) were placed on both sides thereof, to thereby fabricate a sample container having a gap of 0.5 mm. The aqueous copper sulfate solution was confined in the container.

Two coils were attached on one cover glass of the container, as being approximately 5 mm apart from each other, and were pressed by an acryl plate for fixation. An LC oscillation circuit which oscillates at the a resonance frequency (43.5 MHz) was connected to each coil.

The sample and an oscillation circuit containing two sets of coil are fixed in a coil holder, and placed at the center portion of the magnet. The coil holder is internally lined with a 0.05-mm-thick copper foil, so as to prevent external noise from entering the oscillation circuit, containing two sets of coil, placed at the center portion.

The coil holder is placed in the magnet (a permanent magnet of 1 Tesla, having a 45-mm air gap), wherein signal lines of the individual channels are connected to a "send/receive change-over switch" (switching unit 161) and an "amplifier". Two sets of these components were used as being adapted to the number of channels.

The G coil was composed of the G coil 151 and the G coil 153 as shown in FIG. 19, wherein the coils were disposed at positions where the small-sized RF coil 114 is kept therebetween in the in-plane direction of a plane containing the small-sized RF coil 114. Application time d and intervals A of the pulse gradient magnetic field are as below:

d=5 ms

Δ=23 ms

The gradient G was measured by varying intensity in 8 steps. Values of the G are 175.2, 4052.2, 5606.0, 6867.8, 7929.2, 8864.7, 9709.1, and 10490.3 (all in gauss/m).

In this Example, a plurality of A/D conversion boards were provided as the A/D converter 118 to the instrument shown in FIG. 19, and the NMR signals were isolated by measuring the first channel and the second channel with a time lag. The first channel and the second channel were confirmed to have almost equivalent signal intensities (heights)

Figures 47, 48:
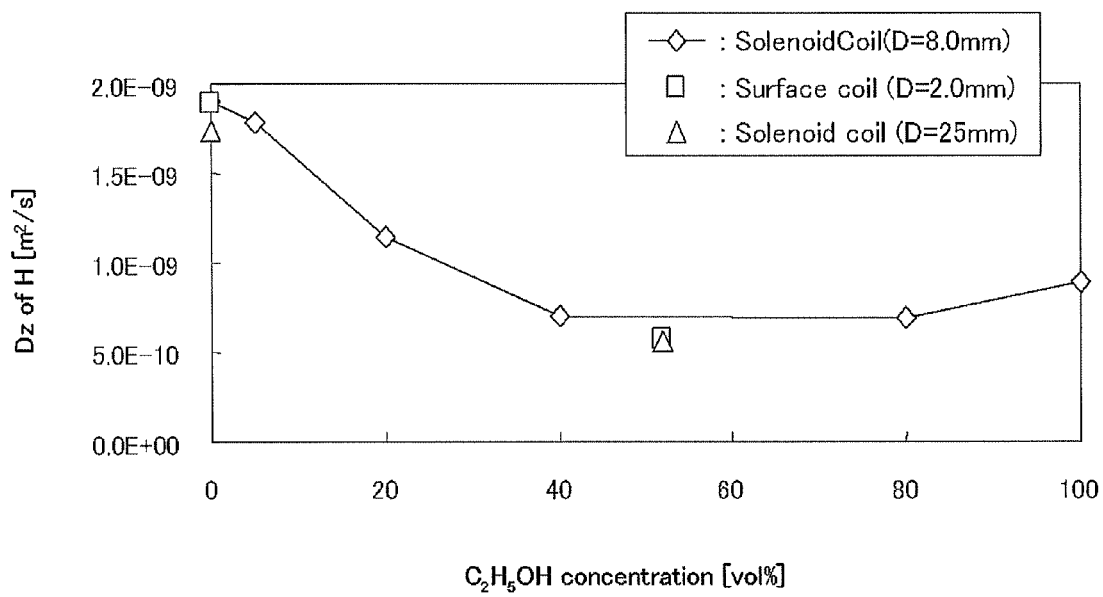
FIG. 47 is a drawing showing results of measurement of self-diffusion coefficient in Example 1.
FIG. 48 is a drawing showing results of measurement of self-diffusion coefficient in Example 2.

Results of measurement of the self-diffusion coefficient obtained by using the above-described instrument are shown in FIG. 47. Case 1 is an exemplary measurement under current supply only to one of two small-sized RF coils, and Case 2 is an exemplary measurement under current supply to both coils.

In this Example, the same aqueous copper sulfate solution confined in a single container was measured using two small-sized RF coils through 2 channels. Therefore, the self-diffusion coefficients measured through 2 channels should have an identical value. All of the measured values shown in FIG. 47 appeared to have equivalent values within ranges of variation, proving that the local mobility was exactly measured.

Example 2

In this Example, the self-diffusion coefficient was measured using an instrument similar to that explained in Example 1.

Using aqueous ethanol solutions (ethanol concentrations of 0% and 52 vol %) as standard samples, the self-diffusion coefficients were measured, and compared with the results obtained by using a large solenoid coil. The self-diffusion coefficients D of the aqueous ethanol solutions were measured using a pair of solenoid coils or planar coils, as the coils applying the oscillating magnetic field for excitation, and also acquiring the magnetic resonance signals corresponded to the gradient magnetic field and the oscillating magnetic field. The solenoid coils herein were used such as those having a diameter of 8 mm and 25 mm. The planar coils herein were used such as having a diameter of 2 mm. Application time d and intervals Δ of the pulse gradient magnetic field are as below:

d=5 ms

Δ=23 ms

The gradient G was measured by varying intensity in 8 steps. Values of the G are 175.2, 4052.2, 5606.0, 6867.8, 7929.2, 8864.7, 9709.1, and 10490.3 (all in gauss/m).

FIG. 48 is a drawing showing results of the measurement. The aqueous ethanol solution is characterized in that "the self-diffusion coefficient of $^1H$, which is a target nucleus, largely varies" depending on the ethanol concentration. Because the target nucleus $^1H$ resides both in $H_2O$ and $C_2H_5OH$, what is measured herein is an "overall self-diffusion coefficient" contributed by both nuclei. Referring to FIG. 48, results of measurement using the small-sized surface coil were found to agree with those obtained by a large solenoid coil. It was also found that the self-diffusion coefficients, almost as large as those obtained by a large solenoid coil, were obtained without correcting the calculated values.

Example 3

In this Example, the self-diffusion coefficient of water molecules in the polymer film depending on the water content was measured using an instrument similar to that explained in Example 1. As the polymer film, Naphion film (from Asahi Glass Co., Ltd.), having a thickness of 500 μm and a size of 16 mm×16 mm was used.

The small-sized RF coil has an outer diameter of 2.0 mm, which is smaller than the sample.

Application time d and intervals A of the pulse gradient magnetic field are as below:

d=5 ms

Δ=23 ms

The gradient G was measured by varying intensity in 8 steps. Values of the G are 175.2, 4052.2, 5606.0, 6867.8, 7929.2, 8864.7, 9709.1, and 10490.3 (all in gauss/m).

Figure 49:
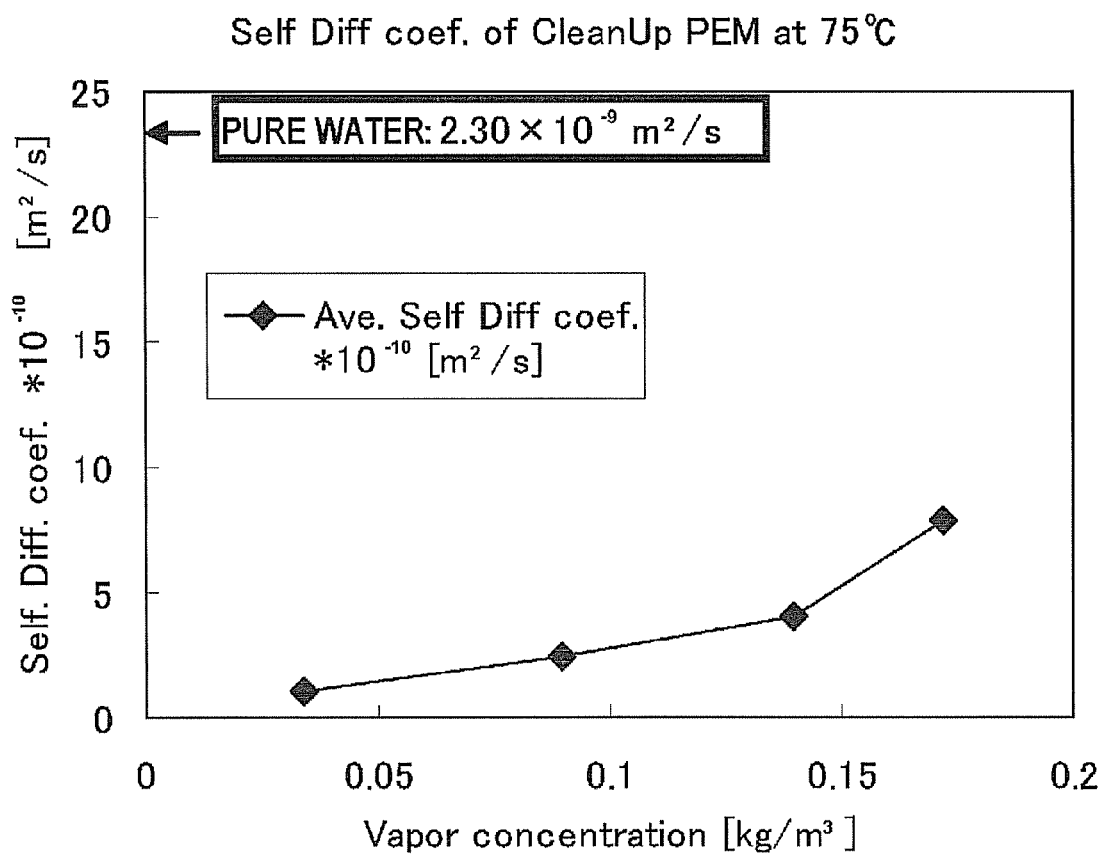
FIG. 49 is a drawing showing results of measurement of self-diffusion coefficient in Example 3.

The self-diffusion coefficient of water molecules was measured by the PGSE method, while varying the water content of the polymer film. Results are shown in FIG. 49. FIG. 49 is a drawing showing dependence of the volume of supply of water vapor to the polymer film (correspondent to the water content of the film), on the self-diffusion coefficient of water molecules in the film. Water vapor concentration on the abscissa indicates water vapor concentration at around the polymer film, and the film has a water content in equilibrium with the water vapor concentration. In short, the abscissa may be assumed as indicating the water content of the polymer film. The ordinate indicates the self-diffusion coefficient of water molecules in the polymer film. From FIG. 49, it is found that the self-diffusion coefficient of water molecules in the film (readiness of movement of water) increases as the water content (amount of moisture) of the film increases.

Example 4

In this Example, using the measuring instrument used in the fifth embodiment, the $T_2$ relaxation time constant (CPMG), and the self-diffusion coefficient of a solid polymer film containing methanol were measured.
[Sample]
In this Example, two types of polymer films differed in the methanol content were measured.
a polymer film having a methanol content of 30 mg
a polymer film having a methanol content of 115 mg
The polymer film used herein was a polymer film (trade name: Flemion, from Asahi Glass Co., Ltd.) having a thickness in dry state of 500 μm, and a size in dry state of 11 mm×11 mm.

Method of preparing the samples will be described below.

[Method of Preparing 115-mg-Methanol-Containing Polymer Film]

A polymer film thoroughly dried using a drier was obtained. Dry weight of the polymer film was measured (measured 90 mg herein).

Next the polymer film was immersed in methanol, and allowed to stand for one month or longer.

The polymer film immersed in methanol was weighed, then from the measured weight, the dry mass of the polymer film was subtracted to thereby determine the methanol content of the polymer film. The methanol content herein was found to be 115 mg.

The polymer film having a methanol content of 115 mg was found to be swelled, 0.6 mm in thickness, and ca. 16 mm×ca. 16 mm in two-dimensional size.

[Method of Preparing 30-mg-Methanol-Containing Polymer Film]

A polymer film thoroughly dried using a drier was obtained. Dry weight of the polymer film was measured (measured 90 mg herein).

On the other hand, the polymer film immersed in methanol was properly dried using a drier so as to adjust the methanol content of the polymer film.

Thereafter polymer was weighed, then from the measured weight, the dry mass of the polymer film was subtracted to thereby determine the methanol content of the polymer film. The methanol content herein was found to be 30 mg.

The polymer film having a methanol content of 30 mg was found to be 0.5 mm in thickness, and ca. 11 mm×ca. 11 mm in two-dimensional size.

[Configuration of Instrument]

The measuring instrument described in the fifth embodiment was used.

The small-sized surface coil (small-sized RF coil) of the measuring instrument used herein was 2.0 mm in diameter, and 3.5 in the number of turn.

[Method of Measurement]

Intensity of every even-numbered echo signal was acquired by the CPMG method, and $T_2$ relaxation time constant (CPMG) was calculated based on attenuation of the intensity.

Next, based on the PGSE method, the self-diffusion coefficient of methanol molecules was calculated based on attenuation of intensity of echo signals.

In the measurement, the polymer film was held between two cover glasses (0.12 mm thick), and the circumference thereof was sealed using a polyimide film. This configuration successfully prevents methanol from vaporizing from the polymer film.

When methanol content of the polymer film is measured, the small-sized coil was brought into contact with the cover glass.

Figure 50:
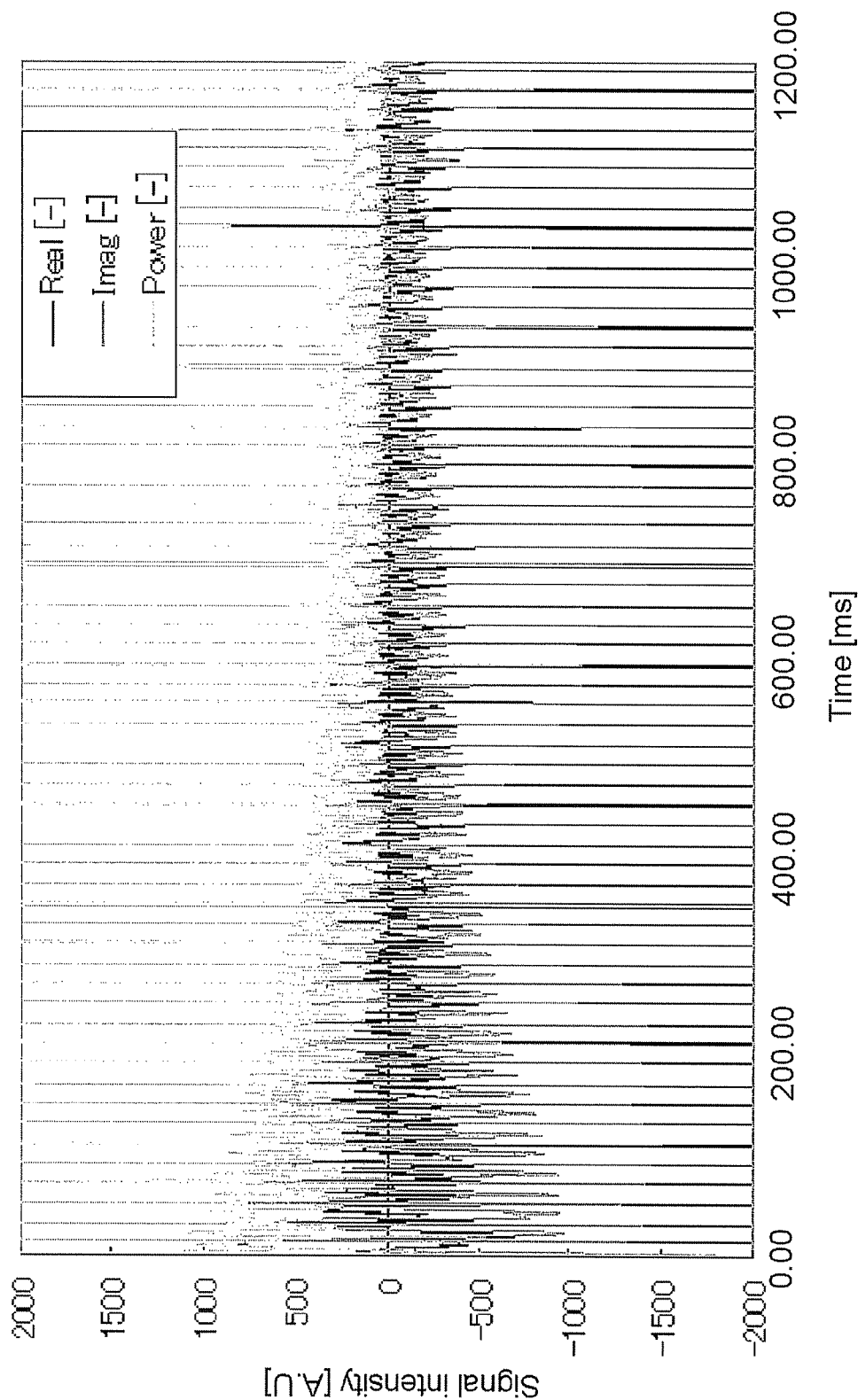
FIG. 50 is a drawing showing an echo signal obtained, by the CPMG method, from a solid polymer film with a methanol content of 30 mg in Example 4.

An exemplary echo signal acquired from the polymer film having a methanol content of 30 mg by the CPMG method was shown in FIG. 50.

The $T_2$ relaxation time constant (CPMG) was then calculated from the attenuation curve of echo signal shown in FIG. 50.

Acquisition of the echo signal herein was repeated 5 times, and calculation of the $T_2$ relaxation time constant (CPMG) was repeated 5 times. The average value of the $T_2$ relaxation time constant (CPMG) was found to be 428.5 ms, with a standard deviation of 88.3 ms.

Figure 51:
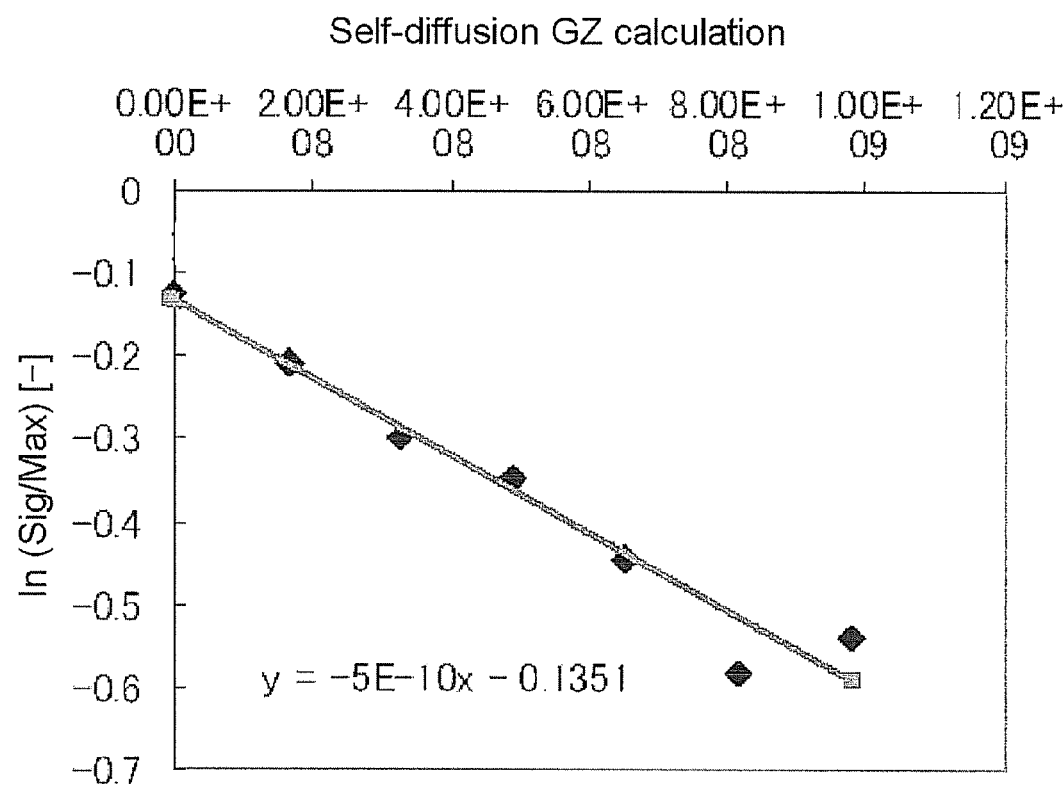
FIG. 51 is a drawing showing a graph obtained from the solid polymer film with a methanol content of 30 mg in Example 4.

A graph obtained from the solid polymer film having a methanol content of 30 mg was shown in FIG. 51. The self-diffusion coefficient of methanol molecules was calculated three times, and the average value was found to be $4.14 \times 10^{-10}$ m$^2$/s, with a standard deviation of $0.44 \times 10^{-10}$ m$^2$/s.

Next, the $T_2$ relaxation time constant (CPMG) of the polymer film having a methanol content of 115 mg was measured.

Figure 52:
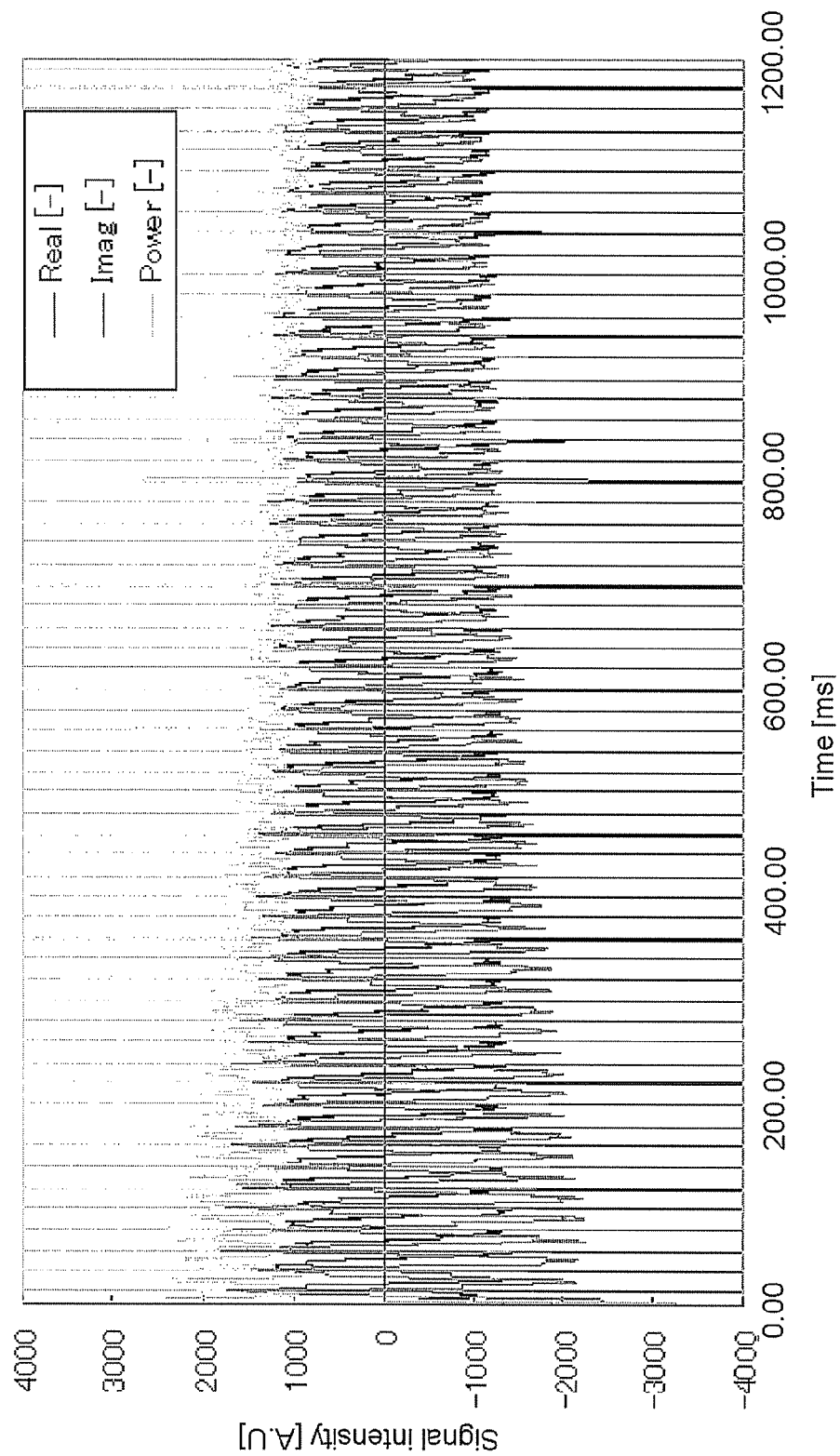
FIG. 52 is a drawing showing an echo signal obtained, by the CPMG method, from a solid polymer film with a methanol content of 115 mg in Example 4.

FIG. 52 shows an exemplary echo signal acquired from the polymer film having a methanol content of 115 mg.

Next, the $T_2$ relaxation time constant (CPMG) was calculated from the attenuation curve of the echo signal shown in FIG. 52.

In this Example, the acquisition of the $T_2$ relaxation time constant (CPMG) from the polymer film having a methanol content of 115 mg was repeated 6 times. The average value of the $T_2$ relaxation time constant (CPMG) was found to be 1715.9 ms, with a standard deviation of 359.1 ms.

Figure 53:
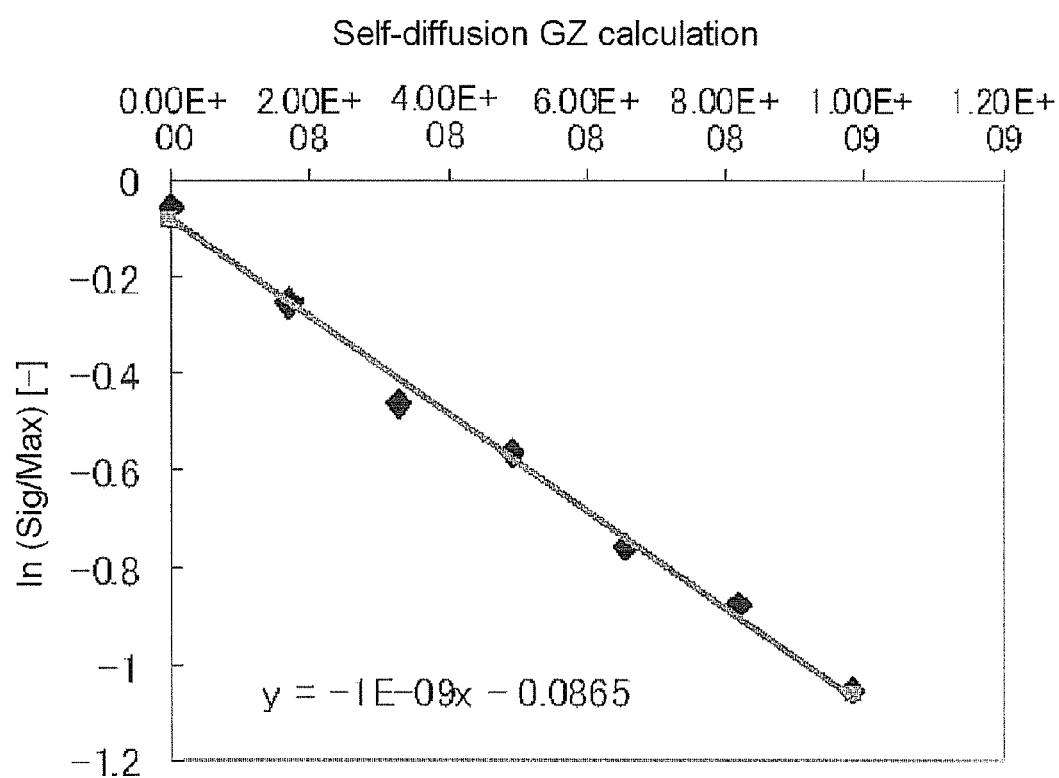
FIG. 53 is a drawing showing a graph obtained from the solid polymer film with a methanol content of 115 mg in Example 4.

A graph obtained from the solid polymer film having a methanol content of 115 mg was shown in FIG. 53. The self-diffusion coefficient of methanol molecules was calculated three times, and the average value was found to be $10.83 \times 10^{-10}$ m$^2$/s, with a standard deviation of $1.23 \times 10^{-10}$ m$^2$/s.

Figure 54:
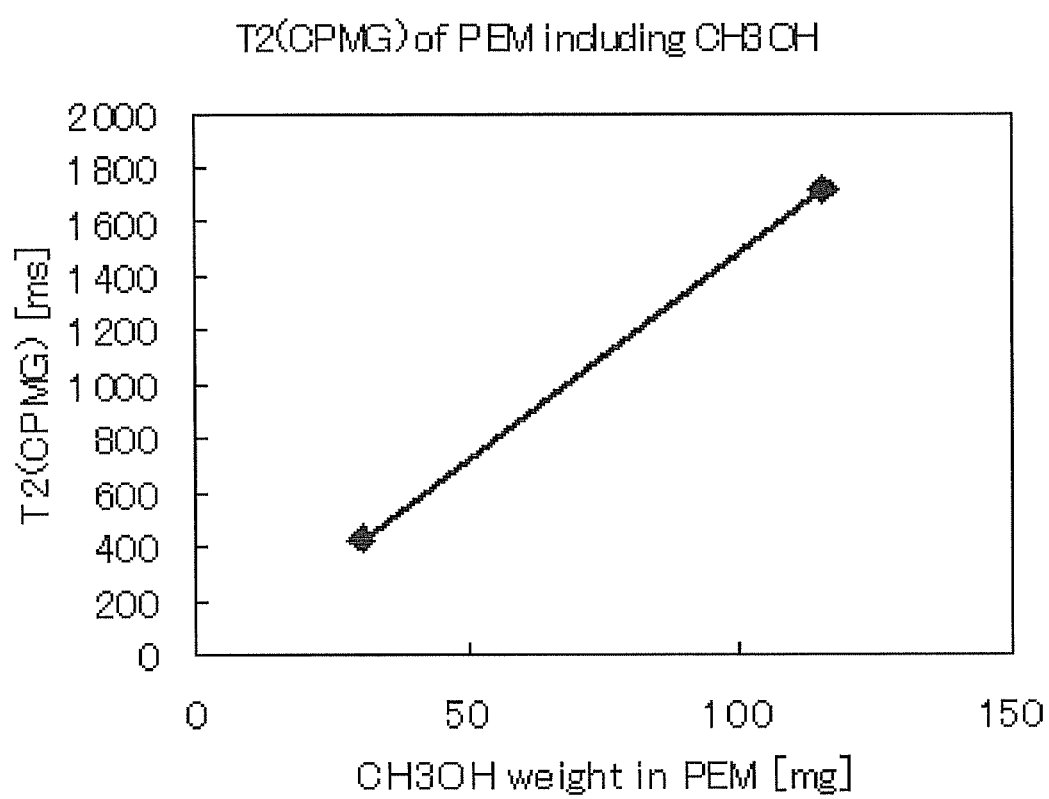
FIG. 54 is a drawing showing relations between the methanol content of the polymer film and $T_2$ relaxation time constant.

FIG. 54 shows relations between the methanol content of the polymer film and the $T_2$ relaxation time constant.

Figure 55:
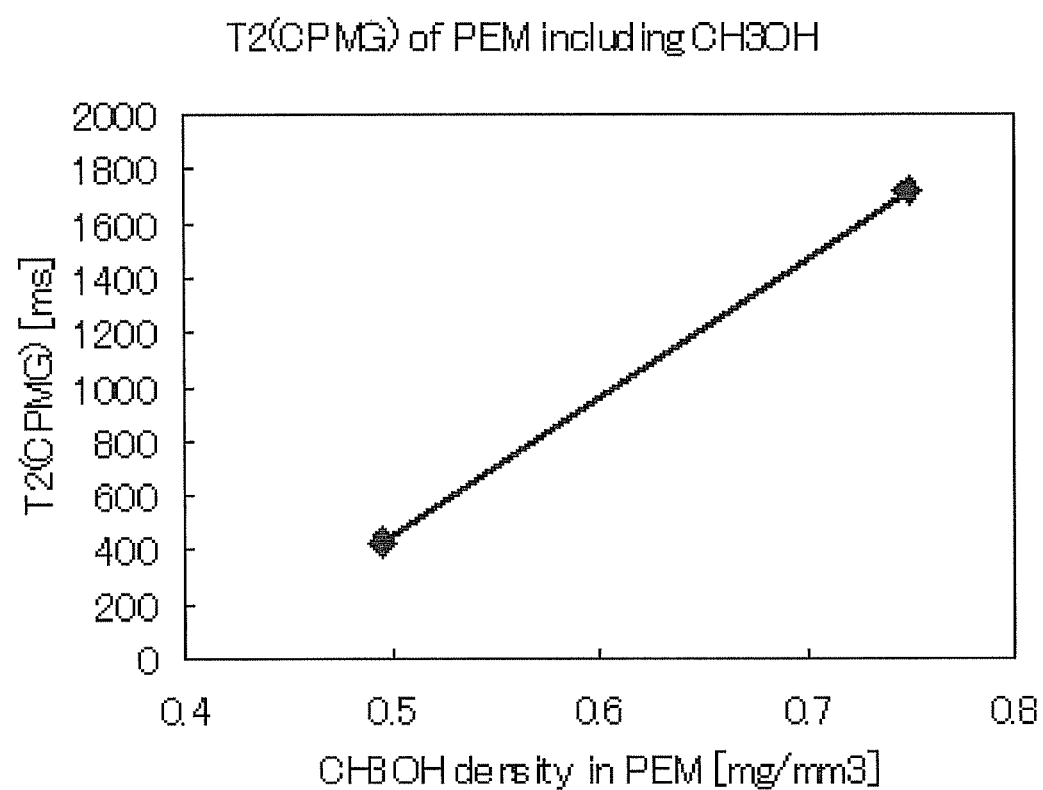
FIG. 55 is a drawing showing relations between the methanol content per unit volume ($mg/mm^3$) and $T_2$ relaxation time constant.

Taking swelling of the polymer film due to methanol contained therein into consideration, FIG. 55 shows relations between the methanol content per unit volume (mg/mm$^3$) and the $T_2$ relaxation time constant.

The $T_2$ relaxation time constant (CPMG) becomes longer as the methanol content increases, showing a clear difference in the $T_2$ relaxation time constant (CPMG) between the higher-methanol-content region and the lower-methanol-content region.

From the results, it is confirmed that the methanol content can be calculated by measuring the $T_2$ relaxation time constant based on the CPMG method.

Figure 56:
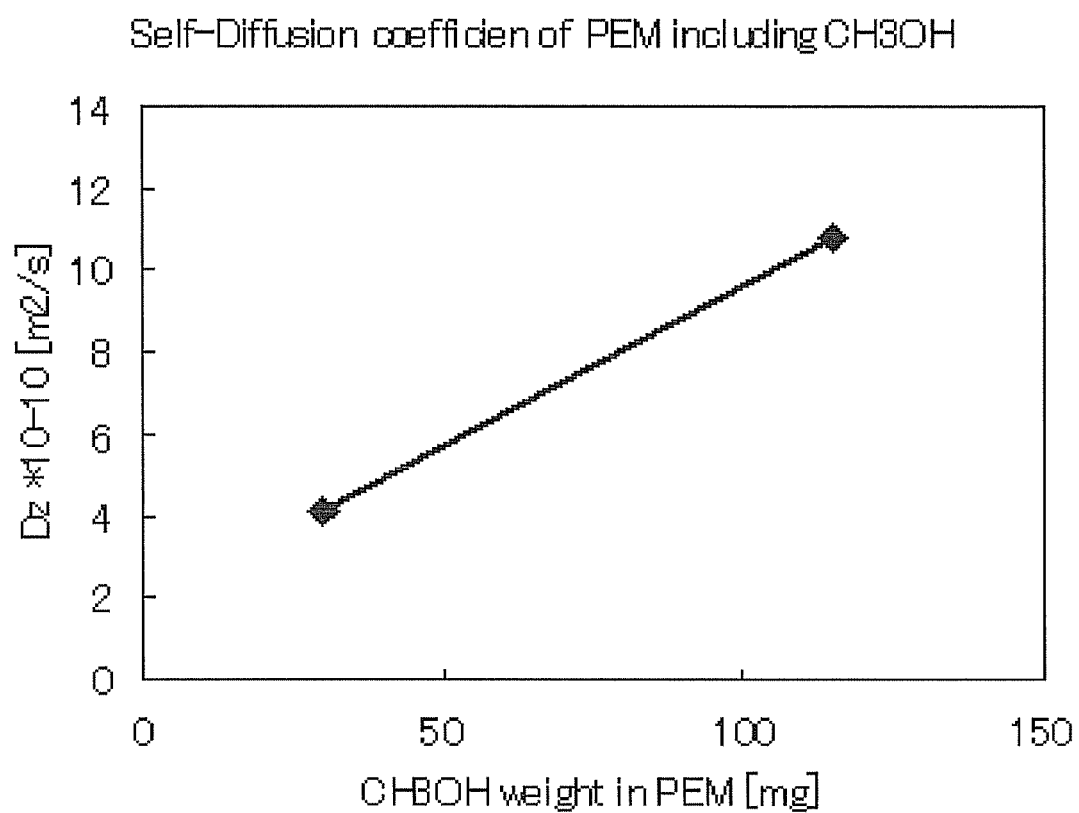
FIG. 56 is a drawing showing relations between the methanol content of the polymer film and self-diffusion coefficient.

FIG. 56 shows relations between the methanol content of the polymer film and the self-diffusion coefficient.

Figure 57:
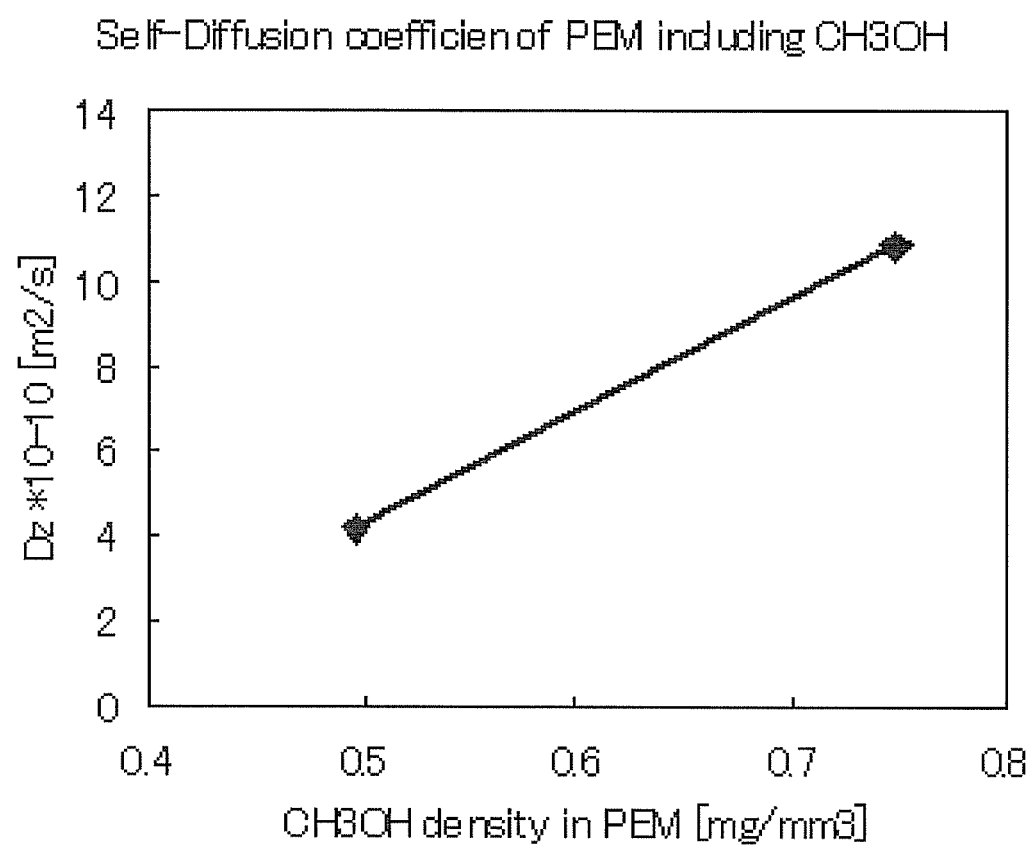
FIG. 57 is a drawing showing relations between the methanol content per unit volume ($mg/mm^3$) and self-diffusion coefficient.

Taking swelling of the polymer film due to methanol contained therein into consideration, FIG. 57 shows relations between the methanol content per unit volume (mg/mm$^3$) and the self-diffusion coefficient.

The self-diffusion coefficient becomes larger as the methanol content increases, showing a clear difference in the self-diffusion coefficient between the higher-methanol-content region and the lower-methanol-content region.

Example 5

In this Example, ratio of the inner diameter and the outer diameter of the small-sized RF coil was investigated.

Using the measuring instrument used in the fifth embodiment, the $T_2$ relaxation time constant from the polymer film was measured based on the CPMG method.

[Configuration of Instrument]

The small-sized RF coils used herein were two types of coils shown below.

3.5-turn coil, 0.8 mm in outer diameter (ratio of inner/outer diameter of 0.4)

3.5-turn coil, 2.0 mm in outer diameter (ratio of inner/outer diameter of 0.65)

Each small-sized RF coil is configured by winding a 50-μm-diameter lead wire with a polyurethane sheath in 3.5 turns in a spiral manner, as being held between 30-μm-thick adhesive polyimide films, so as to keep the geometry.

The polymer film was standardized, and was then properly dried. Thereafter, the polymer film was held between two cover glasses (18 mm×18 mm×0.12 mm thick), and the circumference thereof was sealed with a polyimide film so as to avoid dryness. The small-sized surface coil was placed at the center of the polyimide film, while keeping a distance between the coil and the aqueous solution of 0.15 mm including the 30-μm-thick polyimide film.

Temperature of the polymer film during the measurement was 23 to 24° C.

The water content of the polymer film was calculated on the basis of the mass of a thoroughly dried polymer film, from the amount of increase in weight by water mass.

Results are shown in FIG. 58. In FIG. 58, rhombic plots represent results of measurement obtained using a standard solenoid coil (standard coil) of 25 mm in diameter and 38 mm in length, which is sufficiently larger than the polymer film, and having an excellent uniformity in irradiation of RF magnetic field.

The small-sized RF coil having an outer diameter of 2.0 mm gave almost same $T_2$(CPMG) with that given by the standard coil, wherein the coefficient of variation given by the small-sized RF coil having a diameter of 2.0 mm was found to be 0.04 to 0.06.

In contrast, the small-sized RF coil having an outer diameter of 0.8 mm showed $T_2$(CPMG) largely increased from that shown by the standard coil. In addition, measurement of the a polymer film having a water content of 3.2 of $H_2O/SO_3H^+$ using the small-sized RF coil having an outer diameter of 0.8 mm failed in obtaining a significant level of echo signal relative to noise, so that $T_2$(CPMG) could not be calculated.

Considering the above, it may be concluded that the ratio of the inner/outer diameter of the small-sized RF coil is preferably 0.65 or larger.

Example 6

The principle of measurement of the mobility has been described in the seventh embodiment. In this referential example, a trial was made on understanding the mobility, based on difference between the (i) self-diffusion coefficient obtained in a system showing a phenomenon such that water molecules steadily moving therein in one direction (referred herein to as apparent self-diffusion coefficient) and the (ii) self-diffusion coefficient obtained in a system showing no phenomenon such that water molecules steadily moving therein in one direction.

System (i) corresponds to the case where a DC voltage is applied between the hydrogen electrode and the oxygen electrode, and the polymer electrolyte film was operated in the water electrolysis mode. In this mode, current which flows between both electrodes and the amount of hydrogen ion which moves together with electro-osmotic water between the electrodes are in a proportional relation. Because the amount of movement can experimentally be controlled by controlling the amount of current, the system is suitable for an experiment correlating the apparent self-diffusion coefficient with the mobility.

Even when the system is operated in a reverse manner, or allowed to operate as a fuel cell generating power while being supplied with hydrogen and oxygen, hydrogen ion and electro-osmotic water move from the hydrogen electrode to the oxygen electrode, wherein the amount of movement correspond to the current generation. It can therefore be understood that controlling the amount of movement of hydrogen and electro-osmotic water in the water electrolysis by the amount of current, and correlating their amount of movement and generated current during power generation, are equivalent from the viewpoint of relation between the amount of current and the amount of movement.

Therefore in this experiment, the relation between the apparent self-diffusion coefficient and the mobility will be evaluated in an experimental system controlling the amount of movement of hydrogen ion together with electro-osmotic water, by controlling current in the water electrolysis operation.

More specifically, for the case of (i), intensity of the NMR signals obtained without applying the gradient magnetic field, and intensity of the NMR signals obtained under the gradient magnetic field applied by the PGSE method are detected. Measurement is then made while varying the magnitude of the gradient magnetic field G, relation between $\ln(S/S_0)$ and $-\gamma^2D\Delta^2dG^2$ is plotted, and the self-diffusion coefficient D is determined based on the slope of the plot. The self-diffusion coefficient (apparent self-diffusion coefficient) obtained in the system (i) depends on Brownian motion induced by thermal vibration and movement of water molecules and protons in one direction.

Also for the case of (ii), intensity of the NMR signals obtained without applying the gradient magnetic field, and intensity of the NMR signals obtained under the gradient magnetic field applied by the PGSE method are detected. Measurement is then made while varying the magnitude of the gradient magnetic field G, relation between $\ln(S/S_0)$ and $-\gamma^2D\Delta^2dG^2$ is plotted, and the self-diffusion coefficient D is determined based on the slope of the plot.

Difference between the self-diffusion coefficient in system (ii) and the self-diffusion coefficient in system (i) is considered as being correspondent to the mobility.

On a solid polymer electrolyte film 81 (trade name: Flemion, from Asahi Glass Co., Ltd.), an electrode 82 composed of Pt and Ir was formed on the anode side thereof, and an electrode 83 composed of Pt was formed on the cathode side thereof, by electroless plating, to thereby fabricate an MEA (membrane electrode assembly) 80 (see FIG. 59). The solid polymer electrolyte film 81 is 17 mm×15 mm square, and 500 μm thick. The solid polymer electrolyte film 81 was preliminarily subjected to standardization treatment. More specifically, the solid polymer electrolyte film was immersed into a 3% hydrogen peroxide solution, an ion-exchanged water, an 1 N hydrochloric acid, and an ion-exchanged water in this order, stirred for 1 hour in each solution. Solution temperature was set to 80° C. for all solutions.

For the provision of applying voltage and thereby allowing current to flow between both electrode surfaces of the MEA 80, the MEA 80 was held between two cells each attached with a 10-μm-thick platinum electrode, making the MEA cell suppliable with current. The cell is composed of a polymer material and is an insulator.

Figure 59:
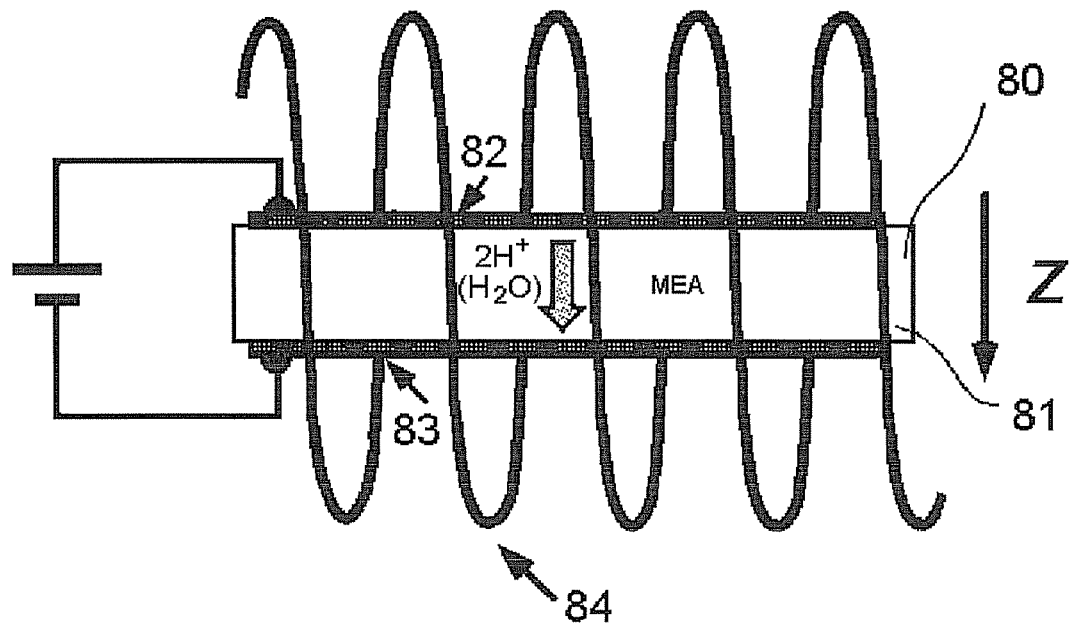
FIG. 59 is a drawing showing a solid polymer electrolyte film and a solenoid coil in Example 6.

A measuring instrument configured almost similarly to as in the first embodiment was used for the measurement of the self-diffusion coefficient, and for the measurement of the apparent self-diffusion coefficient. The measuring instrument used herein was such as replacing the small-sized RF coil of the measuring instrument of the first embodiment with a solenoid coil. At the time of measurement, the MEA cell is placed in the solenoid coil 84 as shown in FIG. 59. The magnet used herein as the static magnetic field application unit of the measuring instrument was a modified Halbach-type magnetic circuit with a magnetic field strength of 1.0 Tesla and an air gap of 45 mm, manufactured by NEOMAX Company.

The gradient magnetic field in the PGSE method was applied in the z-direction. The z-direction is a direction in which hydrogen ion and water molecules are allowed to move in the MEA. The application time d was adjusted to 5 ms, and intervals Δ of application of two gradient magnetic field pulses was adjusted to 23 ms. Intensity Gz of the gradient magnetic field was calibrated by preliminarily measuring the self-diffusion coefficient of distilled water.

Repeating time TR of the 90° pulse for excitation was adjusted to 5 s, echo time TE was adjusted to 30 ms, the number of times of dummy was set to 4, and the number of times of signal integration was set to one. Measurement time required for acquiring the NMR signals under the gradient magnetic field varied in the intensity in 8 steps, was 60 seconds. The $T_1$ relaxation time of the solid polymer electrolyte film 81 was found to be approximately 1100 ms. TR was set to a level approximately 5 times as long as $T_1$.

(I) In re Self-Diffusion Coefficient Obtained under Zero Current Supply to MEA, and Apparent Self-Diffusion Coefficient Obtained under 0.28-A Current Supply The echo signals were obtained by sequentially applying the gradient magnetic field 8 times under varied intensity, and the self-diffusion coefficient was calculated based on 8 values of intensity of the echo signals.

Figure 60:
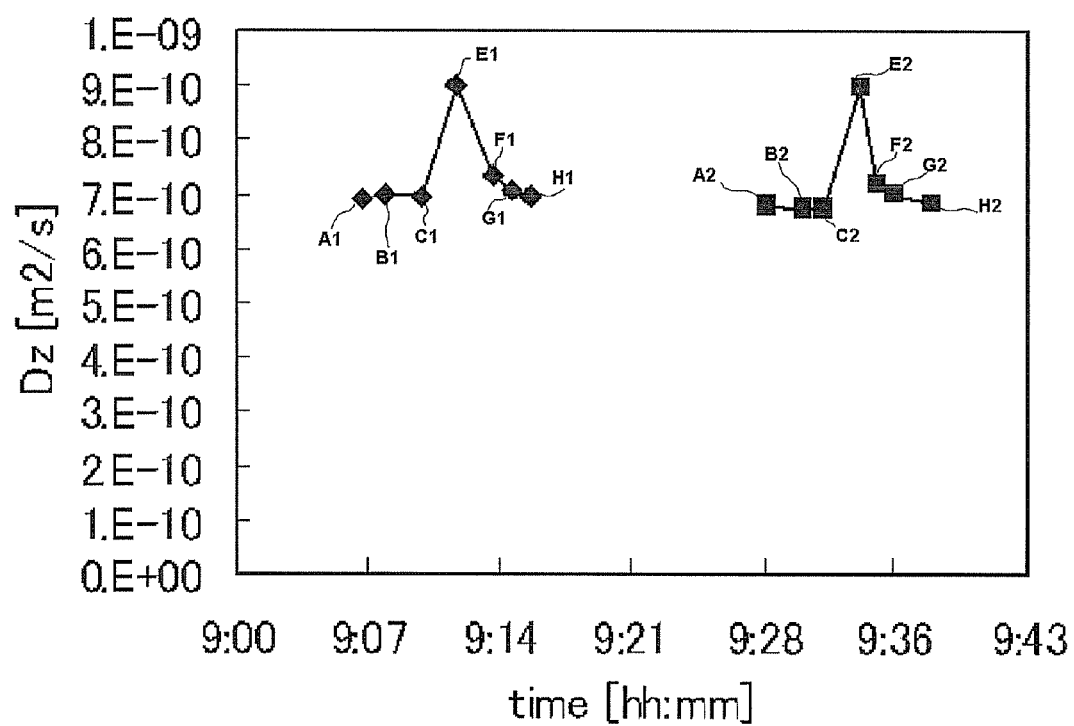
FIG. 60 is a drawing showing results of measurement of self-diffusion coefficient obtained when the solenoid coil was used in Example 6.

(A) First, the self-diffusion coefficients of the MEA were measured without supplying current. Three plots A1 to C1 in FIG. 60 correspond to the self-diffusion coefficients Dz [$m^2$/s] obtained under zero current.

(B) Next, a 0.28-A current was supplied to the MEA only for 60 seconds, so as to measure the "apparent self-diffusion coefficient" in this period. Plot E1 represents the result.

(C) Next, the self-diffusion coefficients of the MEA under zero current were measured. Plots F1 to H1 represent the results.

(D) Next, the operations (A) to (C) were repeated, to thereby measure the self-diffusion coefficients of the MEA. Plots A2 to C2, and plots F2 to H2 represent the self-diffusion coefficient under zero current, and plot E2 represents the self-diffusion coefficient of the MEA under 0.28-A current supply.

Figure 61:
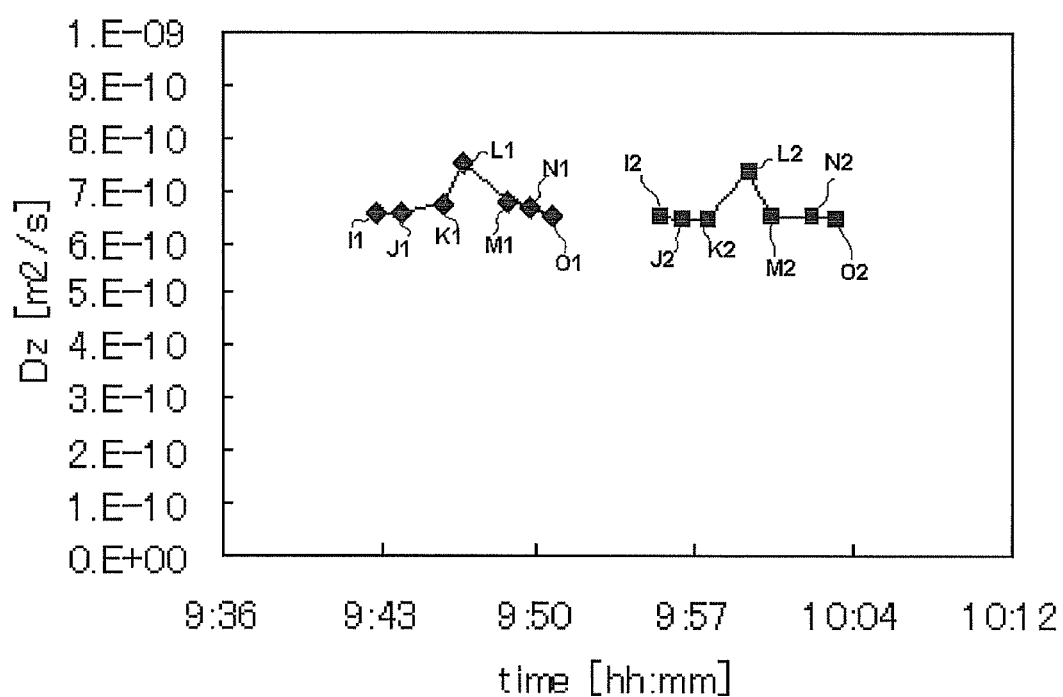
FIG. 61 is a drawing showing results of measurement of self-diffusion coefficient obtained when the solenoid coil was used in Example 6.

(II) In Re Self-Diffusion Coefficient Obtained Under Zero Current Supply to MEA, and Apparent Self-Diffusion Coefficient Obtained Under 0.15-A Current Supply The self-diffusion coefficient obtained under no current supplied to the MEA, and the apparent self-diffusion coefficient obtained under 0.15-A current supply were measured, by the procedures similar to those described for (I). The measurement for (II) was carried out after completion of the measurement for (I). Plots I1 to K1, plots M1 to O1, plots I2 to K2, and plots M2 to O2 in FIG. 61 represent the self-diffusion coefficients of MEA under zero current, and plots L1, L2 in FIG. 61 represent the self-diffusion coefficients of MEA under 0.15-A current supply.

(III) Changes in $T_2$(CPMG) Between (I) and (II) Studied by CPMG Measurement

Figure 62:
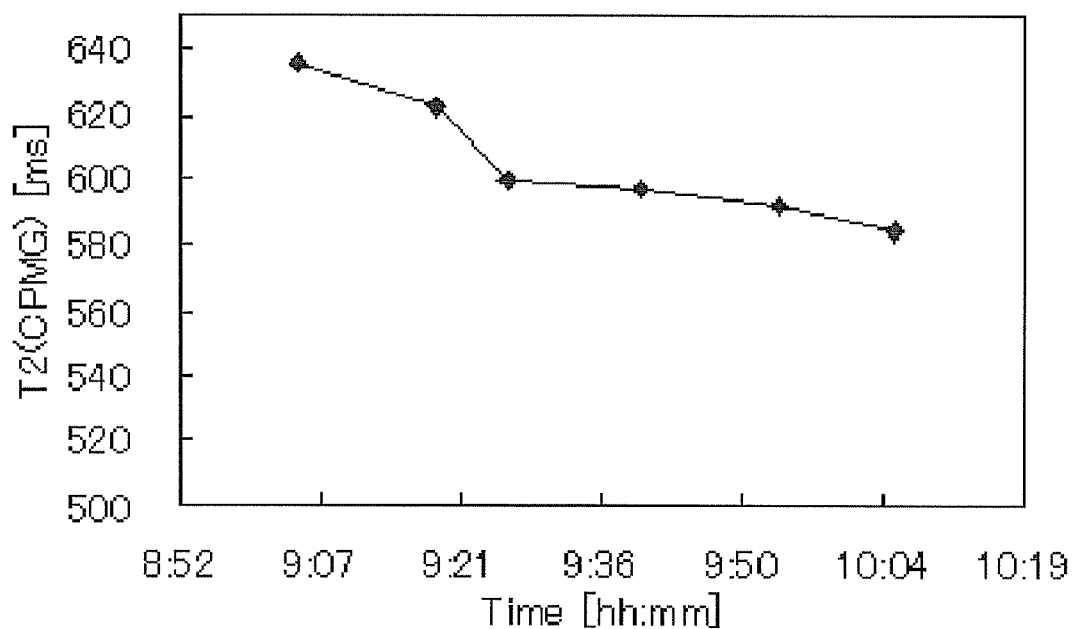
FIG. 62 is a drawing showing results of measurement of $T_2$(CPMG) relaxation time constant obtained when the solenoid coil was used in Example 6.

It is predicted that the water content of the solid polymer electrolyte film 81 may decrease by current supply to the MEA. The $T_2$ (CPMG) relaxation time constant was then calculated based on the CPMG measurement. Because $T_2$(CPMG) increases or decreases depending on (almost proportional to) the water content of the solid polymer electrolyte film 81, changes in the water content can be known by measuring increase or decrease of $T_2$(CPMG). The results are shown in FIG. 62. It is known from the results that $T_2$(CPMG) decreases with progress of water electrolysis, but not to a significant degree. The amount of consumption of water in the solid polymer electrolyte film 81 due to water electrolysis under current supply is 1.67 mg, when calculated based on the amount of charge equivalent to 0.30 A×60 seconds. This amount of water is only as much as 4% or around of 39 mg or around retainable by the polymer electrolyte film 81 in the moistened state thereof.

[Results]

The self-diffusion coefficient was found to be approximately $6.8 \times 10^{-10}$ $m^2$/s when the MEA was not supplied with current (0 A) between both electrodes thereof, the apparent self-diffusion coefficient was found to be approximately $9.0 \times 10^{-10}$ $m^2$/s under 0.28-A current supply, and the apparent self-diffusion coefficient was found to be approximately $7.4 \times 10^{-10}$ $m^2$/s under 0.15-A current supply. From these results, it may be understood that the "apparent self-diffusion coefficient" grows larger depending on energy of current, and that the mobility of hydrogen ions and electro-osmotic water molecules moving through the solid polymer electrolyte film 81 may be understood by the PGSE method.

Next, using the measuring instrument, adopting the small-sized RF coil, configured as described in the first embodiment, the self-diffusion coefficient and the apparent self-diffusion coefficient were measured.

The small-sized RF coil 114 used herein was a planar coil having a 50-μm-diameter lead wire with a polyurethane sheath, wound 3 turns in spiral, having an outer diameter of 1.4. The coil was held between 30-μm-thick adhesive polyimide films 114A, so as to keep the coil geometry (see FIG. 63, wherein only the adhesive polyimide film 114A placed on the bottom surface of the small-sized RF coil 114 is shown in the drawing).

Figure 63:
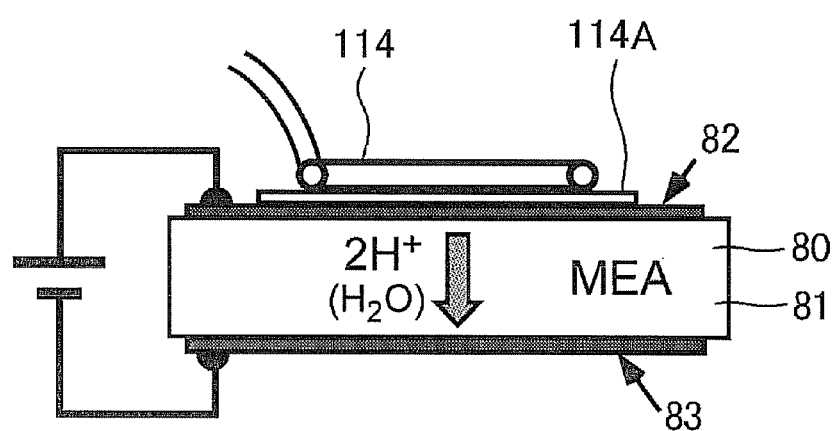
FIG. 63 is a drawing showing the solid polymer electrolyte film and the small-sized RF coil in Example 6.

For the measurement, the small-sized RF coil 114 was disposed with respect to the MEA cell, as shown in FIG. 63. Other experimental conditions are similar to those in the above-described experiment using the solenoid coil.

(III) In Re Self-Diffusion Coefficient Obtained Under Zero Current Supply to MEA, and Apparent Self-Diffusion Coefficient Obtained Under 0.10-A Current Supply The self-diffusion coefficient obtained under no current supplied to the MEA, and the apparent self-diffusion coefficient obtained under 0.10-A current supply were measured, by the procedures similar to those described for (I) where the solenoid coil was used.

Figure 64:
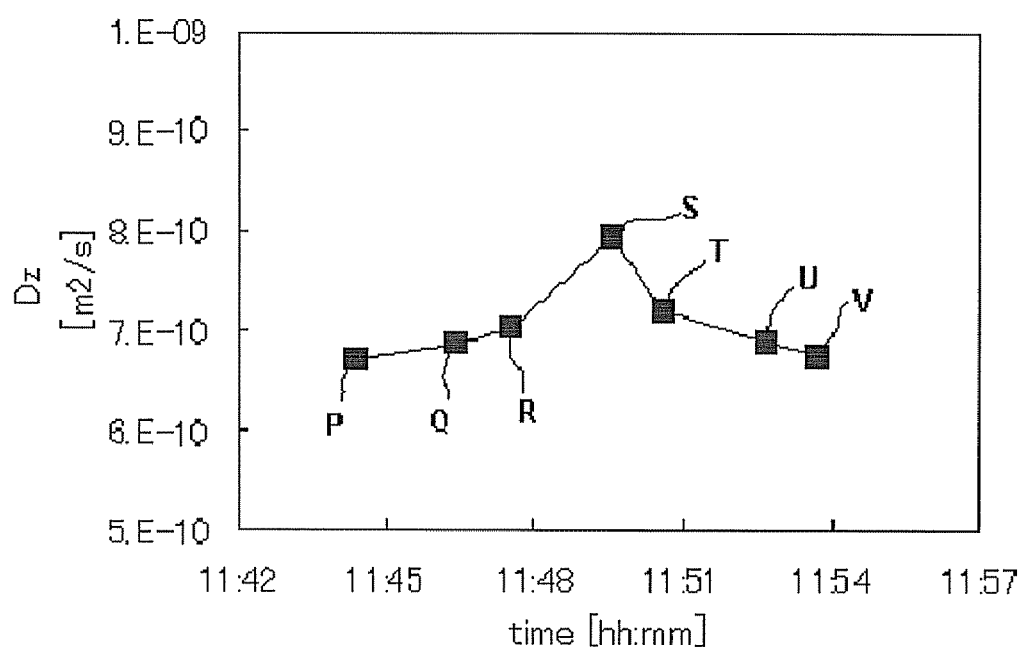
FIG. 64 is a drawing showing results of measurement of self-diffusion coefficient obtained when the small-sized RF coil was used in Example 6.

Results are shown in FIG. 64.

Plots P to R, and plots T to V in FIG. 64 represent the self-diffusion coefficients of MEA under zero current, and plot S in FIG. 64 represents the self-diffusion coefficients of MEA under 0.10-A current supply.

The MEA cell in the progress of water hydrolysis is not supplied with water. In this case, the water in the solid polymer electrolyte film 81 supposedly decreases with time on the anode side thereof, due to electrolysis and electroosmotic flow. The amount of consumption of water in the solid polymer electrolyte film 81 due to water electrolysis under current supply is 0.56 mg, when calculated based on the amount of charge equivalent to 0.10 A×60 seconds. This amount of water is only as much as 1% or around of 39 mg or around retainable by the polymer electrolyte film 81 in the moistened state thereof (as-set state in the pre-experimental cell). Decrease in the water content to as much as this level will not lower the self-diffusion coefficient. This has been proven from the fact that the self-diffusion coefficient obtained after the current supply is almost equivalent to the value obtained before the current supply.

[Results]

The self-diffusion coefficient was found to be approximately $6.8 \times 10^{-10}$ $m^2$/s when the MEA was not supplied with current (0 A) between both electrodes thereof, and the apparent self-diffusion coefficient was found to be approximately $8.0 \times 10^{-10}$ $m^2$/s under 0.10-A current supply. From comparison with the experimental result obtained by using solenoid coil at 0.15 A, it is confirmed that the value of self-diffusion coefficient under zero current and increased value thereof obtained under current supply are almost on the same level.

It may therefore be concluded that the mobility of hydrogen ions and elctro-osomic water molecules moving through the solid polymer electrolyte film 81 can be measured using the small-sized RF coil during current supply to the MEA.

The invention claimed is:

1. An instrument of locally measuring mobility of a protic solvent in a sample, based on the field-gradient magnetic resonance method, comprising:
   a static magnetic field application unit applying a static magnetic field to said sample;
   a gradient magnetic field application unit applying a gradient magnetic field to said sample;
   a small-sized RF coil smaller in size than said sample, applying an oscillating magnetic field for excitation to said sample, and acquiring a magnetic resonance signal corresponded to said oscillating magnetic field for excitation and said gradient magnetic field;
   a control unit applying said gradient magnetic field and said oscillating magnetic field for excitation according to a predetermined pulse sequence; and
   an operation unit calculating said mobility at a specific position in said sample, based on information of said magnetic resonance signals obtained corresponding to different gradient magnetic fields.

2. The mobility measuring instrument as claimed in claim 1,
   wherein said magnetic resonance signal is an NMR signal.

3. The mobility measuring instrument as claimed in claim 2,
   wherein said sample contains a matrix composed of a solid or a gel; and
   said operation unit calculates said mobility of said protic solvent in said matrix.

4. The mobility measuring instrument as claimed in claim 2,
   wherein said gradient magnetic field application unit includes a pair of gradient magnetic field coils disposed while placing said small-sized RF coil in between.

5. The mobility measuring instrument as claimed in claim 4,
   wherein said pair of gradient magnetic field coils are planar coils provided in the same plane with said small-sized RF coil.

6. The mobility measuring instrument as claimed in claim 4,
   wherein said pair of gradient magnetic field coils have a near-semicircular planar geometry, and are opposingly disposed so as to face the individual chords of semicircle towards said small-sized RF coil.

7. The mobility measuring instrument as claimed in claim 2, configured:
   as having a plurality of said small-sized RF coils, said plurality of small-sized RF coils applying said oscillating magnetic field for excitation to a plurality of positions of said sample, and acquiring NMR signals corresponded to said oscillating magnetic field for excitation and said gradient magnetic field, and
   as allowing said operation unit to calculate said mobility at said plurality of position of said sample.

8. The mobility measuring instrument as claimed in claim 2,
   wherein said operation unit further comprises:
   a calculation unit obtaining a calculated value of mobility from intensity of said NMR signals acquired corresponding to different gradient magnetic fields; and
   a correction unit calculating said mobility, by correcting said calculated value of mobility in a manner adaptive to the size of said small-sized RF coil.

9. The mobility measuring instrument as claimed in claim 8, further comprising:
   a storage unit having, stored therein, correction parameters or correction equations used for correcting said calculated value of mobility obtained by said calculation unit in a manner adapted to the size of said small-sized RF coil, and
   said correction unit reads the correction parameters or correction equations out from said storage unit, to thereby calculate said mobility.

10. The mobility measuring instrument as claimed in claim 1, further comprising a support supporting said small-sized RF coil and said gradient magnetic field application unit.

11. The mobility measuring instrument as claimed in claim 10,
    wherein said static magnetic field application unit is attached to said support.

12. The mobility measuring instrument as claimed in claim 10,
    wherein said support has a stick-like form, having said small-sized RF coil and said gradient magnetic field application unit attached to the end portion thereof.

13. The mobility measuring instrument as claimed in claim 10,
    wherein said small-sized RF coil is projected towards said sample side, out from said gradient magnetic field application unit.

14. The mobility measuring instrument as claimed in claim 10, configured as being adjustable in the relative position of said gradient magnetic field application with respect to said small-sized RF coil.

15. The mobility measuring instrument as claimed in claim 14, further comprising a support having said small-sized RF coil and said gradient magnetic field application unit attached thereto,
    said support comprising a main unit having said gradient magnetic field application unit attached to the end portion thereof, and a moving component movable back and forth in a hole formed in said end portion of said main unit,
    said moving component having, on the end portion thereof located on said sample side, said small-sized RF coil.

16. The mobility measuring instrument as claimed in claim 1, having a plurality of said small-sized RF coils,
    said gradient magnetic field application unit having a plurality of gradient magnetic field coils, and
    said gradient magnetic field coils and said small-sized RF coils are alternately disposed.

17. The mobility measuring instrument as claimed in claim 16, further comprising a unit having at least one of said small-sized RF coils and one of said gradient magnetic field coils,
    a plurality of said units are disposed to thereby alternately dispose said gradient magnetic field coils and said small-sized RF coils.

18. The mobility measuring instrument as claimed in claim 2,
    wherein said small-sized RF coil applies said oscillating magnetic field for excitation according to a pulse sequence composed of:
    (a) a 90° pulse; and
    (b) a 180° pulse applied time $\tau$ after the pulse of (a).

19. The mobility measuring instrument as claimed in claim 18,
wherein said pulse sequence contains a 180° pulse applied time τ earlier than said 90° pulse.

20. The mobility measuring instrument as claimed in claim 2, further comprising:
an RF signal generating unit generating said oscillating magnetic field for excitation around said small-sized RF coil;
an NMR signal detecting unit detecting the NMR signal acquired by said small-sized RF coil, and sending said NMR signal to said operation unit; and
a switching circuit provided at a branching portion where said small-sized RF coil, said RF signal generating unit and said NMR signal detecting unit are connected, allowing switching between the state having said small-sized RF coil and said RF signal generating unit connected with each other, and the state having said small-sized RF coil and said NMR signal detecting unit connected with each other.

21. The mobility measuring instrument as claimed in claim 1,
wherein said small-sized RF coil is a planar coil, and having inner diameter/outer diameter of said small-sized RF coil of 0.65 or larger, and 1 or smaller.

22. The mobility measuring instrument as claimed in claim 1,
wherein said operation unit further comprises:
a self-diffusion coefficient calculation unit calculating a self-diffusion coefficient of the protic solvent in said sample under steady movement in one direction, and a self-diffusion coefficient of the protic solvent in said sample not under steady movement in one direction;
a self-diffusion coefficient storage unit storing the self-diffusion coefficients calculated by said self-diffusion coefficient calculation unit; and
a mobility calculation unit calculating the mobility based on difference between the self-diffusion coefficients stored in said self-diffusion coefficient storage unit.

23. A method of locally measuring mobility at a specific position of a sample based on the field-gradient magnetic resonance method, comprising:
a first step applying an oscillating magnetic field for excitation to said sample according to a predetermined pulse sequence;
a second step acquiring a magnetic resonance signal corresponded to the pulse sequence in said first step;
a third step applying an oscillating magnetic field for excitation and gradient magnetic field to said sample according to a predetermined pulse sequence;
a fourth step acquiring a magnetic resonance signal corresponded to the pulse sequence in said third step; and
a fifth step calculating mobility at a specific position of said sample, based on information on the magnetic resonance signal obtained in said second step, and information on said magnetic resonance signal obtained in said fourth step,
wherein, in said first step and said third step, a local magnetic field is applied to a specific position of said sample, using a small-sized RF coil smaller in size than said sample, and
in said second step and said fourth step, said magnetic resonance signal is acquired from the specific position of said sample, using the small-sized RF coil smaller than said sample.

24. The method of measuring mobility as claimed in claim 23,
wherein said magnetic resonance signal is an NMR signal.

25. The method of measuring mobility as claimed in claim 24,
wherein, in said first step, the gradient magnetic field is applied to said sample according to a predetermined pulse sequence, and
in said third step, said gradient magnetic field differed in the energy from that in said first step is applied according to a predetermined pulse sequence.

26. The method of measuring mobility as claimed in claim 24,
wherein said small-sized RF coil applies said oscillating magnetic field for excitation according to a pulse sequence composed of:
(a) a 90° pulse; and
(b) a 180° pulse applied time τ after the pulse of (a).

27. The method of measuring mobility as claimed in claim 26,
wherein said pulse sequence in said first step and said third step contains a 180° pulse applied time τ earlier than said 90° pulse.

28. An instrument of measuring behavior of a protic solvent at a specific position of a sample based on the magnetic resonance method, comprising:
a static magnetic field application unit applying a static magnetic field to said sample;
a gradient magnetic field application unit applying a gradient magnetic field to said sample;
a small-sized RF coil smaller in size than said sample, applying an oscillating magnetic field for excitation to said sample, and acquiring a magnetic resonance signal generated at the specific position of said sample;
a measurement mode selecting unit selecting any one of a plurality of measurement modes including a first measurement mode allowing measurement of the amount of protic solvent at the specific position of said sample, and a second measurement mode allowing measurement of mobility of protic solvent at the specific position of said sample;
a control unit controlling operation of said small-sized RF coil and said gradient magnetic field application unit, according to the measurement mode selected by said measurement mode selecting unit;
a first calculation unit calculating the amount of protic solvent at the specific position of said sample, according to the magnetic resonance signal acquired in said first measurement mode; and
a second calculation unit calculating the mobility of protic solvent at the specific position of said sample, according to the magnetic resonance signal acquired in said second measurement mode;
said control unit being configured:
so as to apply, while being in said first measurement mode, an oscillating magnetic field for excitation through said small-sized RF coil, to the specific position of said sample, and to acquire, through said small-sized RF coil, the magnetic resonance signal generated at said specific position corresponded to said oscillating magnetic field for excitation, and
so as to apply, while being in said second measurement mode, an oscillating magnetic field for excitation through said small-sized RF coil, to the specific position of said sample, and also a gradient magnetic field by said gradient magnetic field application unit, and to acquire, through said small-sized RF coil, the magnetic resonance signal generated corresponding to these magnetic fields.

29. The measuring instrument as claimed in claim 28, further comprising a third calculation unit calculating the amount of movement of the protic solvent, based on the amount of protic solvent calculated by said first calculation unit, and the mobility of protic solvent calculated by said second calculation unit.

30. The measuring instrument as claimed in claim 28, further comprising a support supporting said small-sized RF coil and said gradient magnetic field application unit.

31. The measuring instrument as claimed in claim 30, wherein said static magnetic field application unit is attached to said support.

32. The measuring instrument as claimed in claim 30, wherein said support has a stick-like form, having said small-sized RF coil and said gradient magnetic field application unit attached to the end portion thereof.

33. The measuring instrument as claimed in claim 28, wherein said small-sized RF coil is projected towards said sample side, out from said gradient magnetic field application unit.

34. The measuring instrument as claimed in claim 28, configured as being adjustable in the relative position of said gradient magnetic field application with respect to said small-sized RF coil.

35. The measuring instrument as claimed in claim 34, further comprising a support having said small-sized RF coil and said gradient magnetic field application unit attached thereto,
said support comprising a main unit having said gradient magnetic field application unit attached to the end portion thereof, and a moving component movable back and forth in a hole formed in said end portion of said main unit,
said moving component having, on the end portion thereof located on said sample side, said small-sized RF coil.

36. The measuring instrument as claimed in claim 28, having a plurality of said small-sized RF coils,
said gradient magnetic field application unit having a plurality of gradient magnetic field coils, and
said gradient magnetic field coils and said small-sized RF coils are alternately disposed.

37. The measuring instrument as claimed in claim 36, further comprising a unit having at least one of said small-sized RF coils and one of said gradient magnetic field coils,
a plurality of said units are disposed to thereby alternately dispose said gradient magnetic field coils and said small-sized RF coils.

38. The measuring instrument as claimed in claim 28, wherein said first calculation unit further comprises:
an estimation unit calculating an estimated value of the amount of protic solvent based on intensity of said magnetic resonance signal; and
a correction unit calculating said amount of protic solvent, by correcting said estimated value of the amount of protic solvent in a manner adapted to the size of said small-sized RF coil.

39. The measuring instrument as claimed in claim 38, further comprising:
a storage unit having, stored therein, correction parameters or correction equations used for correcting said estimated value of the amount of protic solvent calculated by said estimation unit, in a manner adapted to the size of said small-sized RF coil, and
said correction unit reads the correction parameters or correction equations out from said storage unit, and corrects said estimated value of the amount of protic solvent, to thereby calculate said amount of protic solvent.

40. The measuring instrument as claimed in claim 28, wherein said second calculation unit further comprises:
an estimation unit calculating an estimated value of mobility, based on the magnetic resonance signal obtained by applying said oscillating magnetic field for excitation and said gradient magnetic field; and
a correction unit calculating said mobility, by correcting said estimated value of mobility in a manner adapted to the size of said small-sized RF coil.

41. The measuring instrument as claimed in claim 40, further comprising:
a storage unit having, stored therein, correction parameters or correction equations used for correcting said estimated value of mobility calculated by said estimation unit, in a manner adapted to the size of said small-sized RF coil, and
said correction unit reads the correction parameters or correction equations out from said storage unit, and corrects said estimated value of mobility, to thereby calculate said mobility.

42. The measuring instrument as claimed in claim 28, further comprising:
an RF excitation pulse generating unit generating an RF excitation pulse raising said oscillating magnetic field for excitation around said small-sized RF coil;
a magnetic resonance signal detecting unit detecting said magnetic resonance signal acquired by said small-sized RF coil, and sending out said magnetic resonance signal to said first calculation unit or said second calculation unit; and
a switching circuit provided at a branching portion where said small-sized RF coil, said RF excitation pulse generating unit and said magnetic resonance signal detecting unit are connected, allowing switching between the state having said small-sized RF coil and said RF excitation pulse generating unit connected with each other, and the state having said small-sized RF coil and said magnetic resonance signal detecting unit connected with each other.

43. The measuring instrument as claimed in claim 28, wherein said small-sized RF coil is a planar coil, and having inner diameter/outer diameter of said small-sized RF coil of 0.65 or larger, and 1 or smaller.

44. The measuring instrument as claimed in claim 28, wherein said second calculation unit further comprises:
a self-diffusion coefficient calculation unit calculating a self-diffusion coefficient of the protic solvent in said sample under steady movement in one direction, and a self-diffusion coefficient of the protic solvent in said sample not under steady movement in one direction;
a self-diffusion coefficient storage unit storing the self-diffusion coefficients calculated by said self-diffusion coefficient calculation unit; and
a mobility calculation unit calculating the mobility based on difference between the self-diffusion coefficients stored in said self-diffusion coefficient storage unit.

45. A method of measuring the amount of protic solvent at a specific position of a sample, and the mobility of protic solvent at said specific position, based on the magnetic resonance method, using a measuring instrument having a static magnetic field application unit applying a static magnetic field to said sample; a gradient magnetic field application unit applying a gradient magnetic field to said sample; and a small-sized RF coil smaller in size than said sample, applying an oscillating magnetic field for excitation to said sample, and acquiring a magnetic resonance signal corresponded to said oscillating magnetic field for excitation and said gradient magnetic field, comprising:

measuring the amount of protic solvent, by selecting a first measurement mode allowing measurement of the amount of protic solvent, and by applying said oscillating magnetic field for excitation; and measuring the mobility of protic solvent, by selecting a second measurement mode allowing measurement of said mobility of protic solvent, and by applying said gradient magnetic field and said oscillating magnetic field for excitation according to a predetermined pulse sequence, said measuring said protic solvent further comprising:

sequentially applying, a plural number of times, an oscillating magnetic field for excitation to a specific position of said sample placed in the static magnetic field, using said small-sized RF coil, and acquiring a plurality of magnetic resonance signals corresponded to said oscillating magnetic field for excitation; and determining said amount of protic solvent at the specific position of said sample, based on intensity of said magnetic resonance signal;

said measuring said mobility further comprising:

a first step applying an oscillating magnetic field for excitation to a specific position of said sample placed in a static magnetic field, using said small-sized RF coil, according to a predetermined pulse sequence;

a second step acquiring the magnetic resonance signal corresponded to said pulse sequence in said first step, using said small-sized RF coil;

a third step applying an oscillating magnetic field for excitation and a gradient magnetic field to the specific position of said sample, according to a predetermined pulse sequence;

a fourth step acquiring the magnetic resonance signal corresponded to the pulse sequence in said third step, using said small-sized RF coil; and a fifth step calculating the mobility of protic solvent at the specific position of said sample, based on the magnetic resonance signal obtained in said second step, and the magnetic resonance signal obtained in said fourth step.

46. The method of measurement as claimed in claim 45, further comprising:

calculating the amount of movement of the protic solvent, based on the amount of protic solvent obtained in said step measuring the amount of protic solvent, and the mobility of protic solvent obtained in said step measuring the mobility of protic solvent.

47. A program executing, by controlling a measuring instrument having a static magnetic field application unit applying a static magnetic field to said sample; a gradient magnetic field application unit applying a gradient magnetic field to said sample; and a small-sized RF coil smaller in size than said sample, applying an oscillating magnetic field for excitation to said sample, and acquiring a magnetic resonance signal corresponded to said oscillating magnetic field for excitation and said gradient magnetic field, measuring the amount of protic solvent, by selecting a first measurement mode allowing measurement of the amount of protic solvent of said sample, and by applying said oscillating magnetic field for excitation; and measuring the mobility of protic solvent, by selecting a second measurement mode allowing measurement of said mobility of protic solvent of said sample, and by applying said gradient magnetic field and said oscillating magnetic field for excitation according to a predetermined pulse sequence, said measuring said protic solvent further comprising:

sequentially applying, a plural number of times, an oscillating magnetic field for excitation to a specific position of said sample placed in the static magnetic field, using said small-sized RF coil, and acquiring a plurality of magnetic resonance signals corresponded to said oscillating magnetic field for excitation; and determining said amount of protic solvent at the specific position of said sample, based on intensity of said magnetic resonance signal;

said measuring said mobility of protic solvent further comprising a first step applying an oscillating magnetic field for excitation to a specific position of said sample placed in a static magnetic field, using said small-sized RF coil, according to a predetermined pulse sequence;

a second step acquiring the magnetic resonance signal corresponded to said pulse sequence in said first step, using said small-sized RF coil;

a third step applying an oscillating magnetic field for excitation and a gradient magnetic field to the specific position of said sample, according to a predetermined pulse sequence;

a fourth step acquiring the magnetic resonance signal corresponded to the pulse sequence in said third step, using said small-sized RF coil; and a fifth step calculating the mobility of protic solvent at the specific position of said sample, based on the magnetic resonance signal obtained in said second step, and the magnetic resonance signal obtained in said fourth step.

48. The program as claimed in claim 47, further comprising:

calculating the amount of movement of the protic solvent, based on the amount of protic solvent obtained in said step measuring the amount of protic solvent, and the mobility of protic solvent obtained in said step measuring the mobility of protic solvent.

49. The mobility measuring instrument as claimed in claim 1, wherein the small-sized RF coil is not larger than a half size of a projected area of the sample.

50. The method of measuring mobility as claimed in claim 23, wherein the small-sized RF coil is not larger than a half size of a projected area of the sample.

* * * * *